US009612246B2

(12) United States Patent
Bruce et al.

(10) Patent No.: US 9,612,246 B2
(45) Date of Patent: Apr. 4, 2017

(54) REAL-TIME ANALYSIS FOR CROSS-LINKED PEPTIDES

(71) Applicant: University of Washington, Seattle, WA (US)

(72) Inventors: James E. Bruce, Kennewick, WA (US); Juan Chavez, Seattle, WA (US); Chad Weisbrod, Seattle, WA (US)

(73) Assignee: University of Washington Though Its Center For Commercialization, Seattle, WA (US)

( * ) Notice: Subject to any disclaimer, the term of this patent is extended or adjusted under 35 U.S.C. 154(b) by 49 days.

(21) Appl. No.: 14/283,902

(22) Filed: May 21, 2014

(65) Prior Publication Data

US 2014/0349871 A1    Nov. 27, 2014

Related U.S. Application Data

(60) Provisional application No. 61/825,901, filed on May 21, 2013.

(51) Int. Cl.

| | |
|---|---|
| *A61K 38/00* | (2006.01) |
| *C07K 2/00* | (2006.01) |
| *C07K 4/00* | (2006.01) |
| *C07K 5/00* | (2006.01) |
| *C07K 14/00* | (2006.01) |
| *C07K 16/00* | (2006.01) |
| *C07K 17/00* | (2006.01) |
| *G01N 33/68* | (2006.01) |
| *G06F 19/26* | (2011.01) |
| *G01N 33/569* | (2006.01) |
| *G01N 33/574* | (2006.01) |
| *C07K 7/06* | (2006.01) |
| *C07K 7/08* | (2006.01) |
| *G06F 19/16* | (2011.01) |

(52) U.S. Cl.
CPC .......... *G01N 33/6848* (2013.01); *C07K 7/06* (2013.01); *C07K 7/08* (2013.01); *G01N 33/56911* (2013.01); *G01N 33/57484* (2013.01); *G06F 19/26* (2013.01); *G01N 2333/212* (2013.01); *G01N 2500/02* (2013.01); *G06F 19/16* (2013.01)

(58) Field of Classification Search
None
See application file for complete search history.

(56) References Cited

U.S. PATENT DOCUMENTS 7,524,925 B2 * 4/2009 Bruce ................ C07D 207/46
530/300

2007/0031815 A1 * 2/2007 Jenkins ............. G01N 33/6872
435/4
2010/0047814 A1 * 2/2010 Bruce .................. C07D 207/46
435/7.1
2013/0144541 A1 * 6/2013 Rychnovsky ...... G01N 33/6848
702/20

OTHER PUBLICATIONS

Matz et al. Electrospray/ion mobility spectrometry/mass spectrometry of proteins. Int. J. Ion Mobility Spectrom, 2001. pp. 77-80.*
Venkaesan et al., "Identification of protein-protein interactions using in vivo cross-linking and mass spectrometry," Proteomics, vol. 4, No. 12, pp. 3845-3854, 2004.
Venkatesan et al., "An empirical framework for binary interactome mapping," Nature Methods, vol. 6, No. 1, pp. 83-90, 2009.
Vidal et al., "Interactome networks and human disease," Cell, vol. 144, No. 6, pp. 986-998, 2011.
Vos et al., "All tangled up: how cells direct, manage and exploit topoisomerase function," Nature Reviews Molecular Cell Biology, vol. 12, No. 12, pp. 827-841, 2011.
Wallin, et al., "Genome-wide analysis of integral membrane proteins from eubacterial, archaean, and eukaryotic organisms," Protein Science, vol. 7, No. 4, pp. 1029-1038, 1998.
Walzthoeni et al., "Mass spectrometry supported determination of protein complex structure," Current Opinion in Structural Biology, vol. 23, No. 2, pp. 252-260, 2013.
Wang et al., "Combinatorial patterns of histone acetylations and methylations in the human genome," Nature Genetics, vol. 40, No. 7, pp. 897-903, 2008.
Wang, et al., "Its the machine that matters: Predicting gene function and phenotype from protein networks," Journal of Proteomics, vol. 73, No. 11, pp. 2277-2289, 2010.
Weisbrod et al., "Performance evaluation of a dual linear ion trap-Fourier transform ion cyclotron resonance mass spectrometer for proteomics research," Journal of Proteomics, vol. 88, pp. 109-119, 2013.
West et al., "Activation of the PI3K/Akt pathway and chemotherapeutic resistance," Drug Resistance Updates, vol. 5, No. 6, pp. 234-248, 2002.
Wilting, et al., "Epigenetic mechanisms in tumorigenesis, tumor cell heterogeneity and drug resistance," Drug Resistance Updates, vo 15, No. 1-2, pp. 21-38, 2012.
Wine et al., "Campylobacter jejuni mediated disruption of polarized epithelia monolayers is cell-type specific, time dependent, and correlates with bacterial invasion," Pediatric Research, vol. 64, No. 6, pp. 599-604, 2008.

(Continued)

*Primary Examiner* — Marcela M Cordero Garcia
(74) *Attorney, Agent, or Firm* — McDonnell Boehnen Hulbert & Berghoff LLP

(57) ABSTRACT

Disclosed herein are methods for large-scale, high-throughput identification of protein-protein interactions and the topologies thereof under physiologically relevant conditions. In one aspect, the disclosure provides methods for identifying one or a plurality of interacting peptides within a biological system comprising obtaining a population of proteins cross-linked with a cleavable protein interaction reporter (PIR) cross-linker, cleaving the PIR crosslinker to produce released peptides and cleaved reporter ions, and analyzing the population of released peptides to identify interacting peptides. Also disclosed are methods for identifying candidate drug compounds, as well as methods of data processing and visualization of protein-protein interactions.

22 Claims, 34 Drawing Sheets

(56) References Cited

OTHER PUBLICATIONS

Woodruff, et al., "Construction and characterization of Pseudomonas aeruginosa protein F-deficient mutants after in vitro and in vivo insertion mutagenesis of the cloned gene," Journal of Bacteriology, vol. 170, No. 6, pp. 2592-2598, 1988.
Xu, "Irinotecan: mechanisms of tumor resistance and novel strategies for modulating its activity," Annals of Oncology, vol. 13, No. 12, pp. 1841-1851, 2002.
Yamel et al., "Interaction of FACT, SSRP1, and the high mobility group (HMG) domain of SSRP1 with DNA damaged by the anticancer drug cisplatin," Journal of Biological Chemistry, vol. 276, No. 28, pp. 25736-25741, 2001.
Yildirim et al., "Drug-target network," Nature Biotechnology, vol. 25, No. 10, pp. 1119-1126, 2007.
Yu et al., "Ligand-independent dimer formation of epidermal growth factor receptor (EGFR) is a step separable from ligand-induced EGFR signaling," Molecular Biology of the Cell, vol. 13, No. 7, pp. 2547-2557, 2002.
Zarantonelli et al., "Transgenic mice expressing human transferrin as a model for meningococcal infection," Infection and Immunity, vol. 75, No. 12, pp. 5609-5614, 2007.
Zhang et al., "Prediction and Analysis of the Protein Interactome in Pseudomonas aeruginosa to Enable Network-Based Drug Target Selection," PLoS One, vol. 7, No. 7, e41202, 2012.
Zhang et al., "PrePPI: a structure-informed database of protein-protein interactions," Nucleic Acids Research, vol. 41, (Database issue), pp. D828-D833, 2013.
Zhang, "I-TASSER server for protein 3D structure prediction," BMC Bioinformatics, vol. 9, No. 40, 2008.
Zybailov et al., "Large Scale Chemical Cross-linking Mass Spectrometry Perspectives," Journal of Proteomics & Bioinformatics, vol. 6, Suppl 2, 001, 2013.
Tang, et al., "Mass Spectrometry Identifiable Cross-Linking Startegy for Studying Portein-Protein Interactions," Anal Chem, 2005, 77:311-318.
Guttman, et al., "Attaching and effacing pathogen-induced tight junction disruption in vivo," Cellular Microbiology, 2006, 8(4): 634-645.
Abergel et al., "Crystallization and preliminary crystallographic study of the peptidoglycan-associated lipoprotein from *Escherichia coli*," Acta Crystallographica Section D, Biological Crystallography, vol. 57, No. 2, pp. 317-319, 2001.
Anderson et al., "Cytokeratin expression results in a drug-resistant phenotype to six different chemotherapeutic agents," Clinical Cancer Research, vol. 2, No. 1, pp. 97-105, 1996.
Andreeva et al., "Data growth and its impact on the SCOP database: New developments," Nucleic Acids Research, vol. 36, Suppl 1, pp. D419-D425, 2008.
Anger et al., "Structures of the human and *Drosophila* 80S ribosome," Nature, vol. 497, No. 7447, pp. 80-85, 2013.
Arkowitz, et al., "SecD and SecF are required for the proton electrochemical gradient stimulation of preprotein translocation," EMBO Journal, vol. 13, No. 4, 954-963, 1994.
Bauman et al., "Expression of cytokeratin confers multiple drug resistance," Proceedings of the National Academy of Sciences USA, vol. 91, No. 12, pp. 5311-5314, 1994.
Beck et al., "The quantitative proteome of a human cell line," Molecular Systems Biology, vol. 7, No. 1, pp. 549, 2011.
Bichat et al., "Cytoskeleton alteration in MCF7R cells, a multidrug resistant human breast cancer cell line," Anticancer Research, vol. 17,1 No. 5A, pp. 3393-3401, 1997.
Bomberger et al., "Long-distance delivery of bacterial virulence factors by Pseudomonas aeruginosa outer membrane vesicles," PLoS Pathogens, vol. 5, No. 4, e1000382, 2009.
Brinkman et al., "The amino terminus of Pseudomonas aeruginosa outer membrane protein OprF forms channels in lipid bilayer membranes: correlation with a three-dimensional model," Journal of Bacteriology, vol. 182, No. 18, pp. 5251-5255, 2000.
C. Holohan et al., "Cancer drug resistance: an evolving paradigm," Nature Reviews Cancer, vol. 13, No. 10, pp. 714-726, 2013.
Carpenter et al., "Overcoming the challenges of membrane protein crystallography," Current Opinion in Structural Biology, vol. 18, No. 5 pp. 581-586, 2008.
Cascales et al., "Pal lipoprotein of *Escherichia coli* plays a major role in outer membrane integrity," Journal of Bacteriology, vol. 184, No. 3, pp. 754-759, 2002.
Cascales, et al., "Deletion analyses of the peptidoglycan-associated lipoprotein Pal reveals three independent binding sequences including a ToIA box," Molecular Microbiology, vol. 51, No. 3, pp. 873-885, 2004.
Caulin et al., "Caspase cleavage of keratin 18 and reorganization of intermediate filaments during epithelial cell apoptosis," Journal of Cell Biology, vol. 138, No. 6, pp. 1379-1394, 1997.
Chavez et al. "Quantitative interactome analysis reveals a chemoresistant edgotype," Nature Communications, vol. 6, No. 7928, pp. 1-12. 2015.
Chavez et al., "Quantitative proteomic and interaction network analysis of cisplatin resistance in HeLa cells," PLoS One, vol. 6, No. 5, e19892, 2011.
Chen et al., "The HDAC inhibitor, MPT0E028, enhances erlotinib-induced cell death in EGFR-TKI-resistant NSCLC cells," Cell Death & Disease, vol. 4, No. e810, 2013.
Chikamori et al., "Phosphorylation of serine 1106 in the catalytic domain of topoisomerase II alpha regulates enzymatic activity and drug sensitivity," Journal of Biological Chemistry, vol. 278, No. 15, pp. 12696-12702, 2003.
Choi et al., "Acinetobacter baumannii invades epithelial cells and outer membrane protein a mediates interactions with epithelial cells," BMC Microbiology, vol. 8, No. 216, 2008.
Choi et al., "Acinetobacter baumannii outer membrane protein a targets the nucleus and induces cytotoxicity," Cellular Microbiology, vol. 10, No. 2, pp. 309-319, 2008.
Choi et al., "Proteomic analysis of outer membrane vesicles derived from Pseudomonas aeruginosa," Proteomics, vol. 11, No. 16, pp. 3424-3429, 2011.
Choi et al., "Structures of two intermediate filament-binding fragments of desmoplakin reveal a unique repeat motif structure," Nature Structural Biology, vol. 9, No. 8, pp. 612-620, 2002.
Chrencik et al., "Mechanisms of camptothecin resistance by human topoisomerase I mutations," Journal of Molecular Biology, vol. 339, No. 4, pp. 773-784, 2004.
Confer, "The OmpA family of proteins: roles in bacterial pathogenesis and immunity," Veterinary Microbiology, vol. 163, No. 3-4, pp. 207-222, 2013.
Cossart, et al., "Bacterial invasion: the paradigms of enteroinvasive pathogens," Science, vol. 304, No. 5668, pp. 242-248, 2004.
Cossart, et al., "Interactions of Listeria monocytogenes with mammalian cells during entry and actin-based movement: bacterial factors, cellular ligands and signaling," EMBO Journal, vol. 17, No. 14, pp. 3797-3806, 1998.
Cress, et al., "Multiple drug resistance and intermediate filaments," Cancer Metastasis Reviews, vol. 15, No. 4, pp. 499-506, 1996.
Cui et al., "Uncovering new signaling proteins and potential drug targets through the interactome analysis of Mycobacterium tuberculosis," BMC Genomics, vol. 10, No. 118, 2009.
Damron et al., "Lipotoxin F of Pseudomonas aeruginosa is an AlgU-dependent and alginate-independent outer membrane protein involved in resistance to oxidative stress and adhesion to A549 human lung epithelia," Microbiology, vol. 155, pp. 1028-1038, 2009.
Davies, et al., "Origins and evolution of antibiotic resistance," Microbiology and Molecular Biology Reviews, vol. 74, No. 3, pp. 417-433, 2010.
de Haas et al., "Clinical evaluation of M30 and M65 ELISA cell death assays as circulating biomarkers in a drug-sensitive tumor, testicular cancer," Neoplasia, vol. 10, No. 10, pp. 1041-1048, 2008.
Delva et al., "The desmosome," Cold Spring Harbor Perspectives in Biology, vol. 1, No. 2, a002543, 2009.
Demogines et al., "Dual host-virus arms races shape an essential housekeeping protein," PLoS Biology, vol. 11, No. 5, e1001571,2013.

(56) References Cited

OTHER PUBLICATIONS

Dong, "Structural basis for gate-DNA recognition and bending by type IIA topoisomerases," Nature, vol. 450, No. 7173, pp. 1201-1205, 2007.
Elde et al., "Protein kinase R reveals an evolutionary model for defeating viral mimicry," Nature, vol. 457, No. 7228, pp. 485-489, 2009.
Elde, et al., "The evolutionary conundrum of pathogen mimicry," Nature Reviews Microbiology, vol. 7, No. 11, pp. 787-797, 2009.
Esteller, "Cancer epigenomics: DNA methylomes and histone-modification maps," Nature Reviews Genetics, vol. 8, No. 4, pp. 286-298, 2007.
Firoved et al., "Microarray analysis reveals induction of lipoprotein genes in mucoid Pseudomonas aeruginosa: implications inflammation for inflammation in cystic fibrosis," Infection and Immunity, vol. 72, No. 9, pp. 5012-5018, 2004.
Fnu et al., "Methylation of histone H3 lysine 36 enhances DNA repair by nonhomologous end-joining," Proceedings of the National Academy of Sciences USA, vol. 108, No. 2, pp. 540-545, 2011.
Franceschini et al., "STRING v9.1: protein-protein interaction networks, with increased coverage and integration," vol. 41, (Database issue), pp. D808-D815, 2013.
Galdiero et al., "Microbe-host interactions: structure and role of Gram-negative bacterial porins," Current Protein & Peptide Science, vol. 13, No. 8, pp. 843-854, 2012.
Garcia et al., "Facilitates chromatin transcription complex is an 'accelerator' of tumor transformation and potential marker and target of aggressive cancers," Cell Reports, vol. 4, No. 1, pp. 159-173, 2013.
Garrod, et al., "Desmosome structure, composition and function," Biochimica et Biophysica Acta, vol. 1778, No. 3, pp. 572-587, 2008.
Gasparian et al., "Curaxins: anticancer compounds that simultaneously suppress NF-kappaB and activate p53 by targeting FACT," Science Translational Medicine, vol. 3, No. 95, 2011.
Gillet, et al., "Mechanisms of multidrug resistance in cancer," Methods in Molecular Biology, vol. 596, pp. 47-76, 2010.
Goldman et al., "Inroads into the structure and function of intermediate filament networks," Journal of Structural Biology, vol. 177, No. 1, pp. 14-23, 2012.
Goll et al., "MPIDB: the microbial protein interaction database," Bioinformatics, vol. 24, No. 15, pp. 1743-1744, 2008.
Goure et al., "The V antigen of Pseudomonas aeruginosa is required for assembly of the functional PopB/PopD translocation pore in host cell membranes," Infection and Immunity, vol. 72, No. 8, pp. 4741-4750, 2004.
Greber et al., "Architecture of the large subunit of the mammalian mitochondrial ribosome," Nature, vol. 505, No. 7484, pp. 515-519, 2014.
Green, et al., "Desmosomes: new perspectives on a classic," Journal of Investigative Dermatology, vol. 127, No. 11, pp. 2499-2515, 2007.
Guerrero et al., "An integrated mass spectrometry-based proteomic approach: quantitative analysis of tandem affinity-purified in vivo cross-linked protein complexes (QTAX) to decipher the 26 S proteasome-interacting network," Molecular and Cellular Proteomics, vol. 5, No. 2, pp. 366-378, 2006.
Guerrero et al., "Characterization of the proteasome interaction network using a QTAX-based tag-team strategy and protein interaction network analysis," Proceedings of the National Academy of Sciences USA, vol. 105, No. 36, pp. 13333-13338, 2008.
Guillaumond et al., et al., "Chromatin remodeling as a mechanism for circadian prolactin transcription: rhythmic NONO and SFPQ recruitment to HLTF," FASEB Journal, vol. 25, No. 8, pp. 2740-2756, 2011.
Guttman et al., "Desmosomes are unaltered during infections by attaching and effacing pathogens," Anatomical Record, vol. 290, No. 2, pp. 199-205, 2007.
Hammer et al., "Proteomic analysis of doxorubicin-induced changes in the proteome of HepG2cells combining 2-D DIGE and LC-MS/MS approaches," Proteomics, vol. 10, No. 1, pp. 99-114, 2010.

Jager et al., "Global landscape of HIV-human protein complexes," Nature, vol. 481, No. 7381, pp. 365-370, 2012.
Jin et al., "Acinetobacter baumannii secretes cytotoxic outer membrane protein A via outer membrane vesicles," PLoS One, vol. 6, No. 2, e17027, 2011.
Kaneko et al., "The transition metal gallium disrupts Pseudomonas aeruginosa iron metabolism and has antimicrobial and antibiofilm activity," Journal of Clinical Investigation, vol. 117, No. 4, pp. 877-888, 2007.
Kao et al., "Development of a novel cross-linking strategy for fast and accurate identification of cross-linked peptides of protein complexes," Molecular & Cellular Proteomics, vol. 10, No. 1, pp. M110.002212, 2011.
Kao et al., "Mapping the structural topology of the yeast 19S proteasomal regulatory particle using chemical crosslinking linking and probabilistic modeling," Molecular & Cellular Proteomics, vol. 11, No. 12, pp. 1566-1577, 2012.
Karantza, "Keratins in health and cancer: more than mere epithelial cell markers," Oncogene, vol. 30, No. 2, pp. 127-138, 2011.
Khalid et al., "Modeling and simulation of a bacterial outer membrane protein: OprF from Pseudomonas aeruginosa," Proteins, vol. 63, No. 1, pp. 6-15, 2006.
Kulak et al., "Minimal, encapsulated proteomic-sample processing applied to copy-number estimation in eukaryotic cells," Nature Methods, No. 11, vol. 3, pp. 319-324, 2014.
Kumar, et al., "HPIDB—a unified resource for host-pathogen interactions," BMC Bioinformatics, vol. 11, Suppl 6:S16, 2010.
Kumari et al., "A role for SSRP1 in recombination-mediated DNA damage response," Journal of Cellular Biochemistry, vol. 108, No. 2, pp. 508-518, 2009.
Kwon et al- "Proteome analysis of outer membrane vesicles from a clinical Acinetobacter baumannii isolate," FEMS Microbiology Letters, vol. 297, No. 2, pp. 150-156, 2009.
Lane, et al., "Histone deacetylase inhibitors in cancer therapy," Journal of Clinical Oncology, vol. 27, No. 32, pp. 5459-5468, 2009.
Lee et al., "Acinetobacter baumannii outer membrane protein A induces dendritic cell death through mitochondrial targeting," Journal of Microbiology, vol. 48, No. 3, pp. 387-392, 2010.
Leitner et al.,"The molecular architecture of the eukaryotic chaperonin TRiC/CCT," Structure, vol. 20, No. 5, pp. 814-825, 2012.
Liévin-Le Moal, et al., "The front line of enteric host defense against unwelcome intrusion of harmful microorganisms: mucins, antimicrobial peptides, and microbiota," Clinical Microbiology Reviews, vol. 19, No. 2, pp. 315-337, 2006.
Lilic et al., et al., "Identification of the CysB-regulated gene, hslJ, related to the *Escherichia coli* novobiocin resistance phenotype," FEMS Microbiology Letters, vol. 224, No. 2, pp. 239-246, 2003.
Lin et al., "Outer membrane protein I of Pseudomonas aeruginosa is a target of cationic antimicrobial peptide/protein," Journal of Biological Chemistry, vol. 285, No. 12, pp. 8985-8994, 2010.
Liu et al., "Co-expression of cytokeratin 8 and breast cancer resistant protein indicates a multifactoral drug-resistant phenotype in human breast cancer cell line," Life Sciences, vol. 83, No. 13-14, pp. 496-501, 2008.
Liu et al., "Proteome-wide profiling of protein assemblies by cross-linking mass spectrometry," Nature Methods, advanced online publication, doi: 10.1038/nmeth.3603l available online at: http://www.nature.com/nmeth/journal/vaop/ncurrent/full/nmeth.3603.html, 2015.
Liu, et al., "Combinatorial electrostatic collision-induced dissociative chemical cross-linking reagents for probing protein surface topology," Analytical Chemistry, vol. 82, No. 14, pp. 6215-6223, 2010.
Maiso et al., "The histone deacetylase inhibitor LBH589 is a potent antimyeloma agent that overcomes drug resistance," Cancer Research, vol. 66, No. 11, pp. 5781-5789, 2006.
Maliepaard et al., "Circumvention of breast cancer resistance protein (BCRP)-mediated resistance to camptothecins in vitro using non-substrate drugs or the BCRP inhibitor GF120918," Clinical Cancer Research, vol. 7, No. 4, pp. 935-941, 2001.

(56) References Cited

OTHER PUBLICATIONS

Marcoux et al., "An enhanced protein crosslink identification strategy using CID-cleavable chemical crosslinkers and LC/MS(n) analysis," Structure, vol. 22, No. 5, pp. 781-790, 2014.

Marianayagam et al., "The power of two: protein dimerization in biology," Trends in Biochemical Sciences, vol. 29, No. 11, pp. 618-625, 2004.

Marquordt et al., "Posttranslational modification of serine to formylglycine in bacterial sulfatases. Recognition of the modification motif by the iron-sulfur protein AtsB," Journal of Biological Chemistry, vol. 278, No. 4, pp. 2212-2218, 2003.

McConnell et al., "Acinetobacter baumannii: human infections, factors contributing to pathogenesis and animal models," FEMS Microbiology Reviews, vol. 37, No. 2, pp. 130-155, 2013.

Meier et al., "Proteome-wide protein interaction measurements of bacterial proteins of unknown function," Proceedings of the National Academy of Sciences, vol. 110, No. 2, pp. 477-482, 2013.

Meng et al.,"Informatics and multiplexing of intact protein identification in bacteria and the archaea," Nature Biotechnology, vol. 19, No. 10, pp. 952-957, 2001.

Mizuno, "Isolation and characterization of major outer membrane proteins of Pseudomonas aeruginosa strain PAO with special reference to peptidoglycan-associated protein," Journal of Biochemistry, vol. 86, No. 4, pp. 979-989, 1979.

Mizuno, et al., "Isolation and characterization of a major outer membrane protein of Pseudomonas aeruginosa: Evidence for the occurrence of a lipoprotein," Journal of Biochemistry, vol. 85, No. 1, pp. 115-122, 1979.

Müller et al., "Cleavable cross-linker for protein structure analysis: reliable identification of cross-linking products by tandem MS," Analytical Chemistry, vol. 82, No. 16, pp. 6958-6968, 2010.

Navare et al., "Probing the protein interaction network of Pseudomonas aeruginosa cells by chemical cross-linking mass spectrometry," Structure, vol. 23, No. 4, pp. 762-773, 2015.

Nekrasova, et al., "Desmosome assembly and dynamics," Trends in Cell Biology, vol. 23, No. 11, pp. 537-546, 2013.

Norris et al., "Expression of multidrug transporter MRP4/ABCC4 is a marker of poor prognosis in neuroblastoma and confers resistance to irinotecan in vitro," Molecular Cancer Therapeutics, vol. 4, No. 4, pp. 547-553, 2005.

Nouwen et al., "The large first periplasmic loop of SecD and SecF plays an important role in SecDF functioning," Journal of Bacteriology, vol. 187, No. 16, pp. 5857-5860, 2005.

Okuda et al., "Translocation of Pseudomonas aeruginosa from the intestinal tract is mediated by the binding of ExoS to an Na,K-ATPase regulator, FXYD3," Infection and Immunity, vol. 78, No. 11, pp. 4511-4522, 2010.

Oliver et al., "High frequency of hypermutable Pseudomonas aeruginosa in cystic fibrosis lung infection," Science, vol. 288, No. 5469, pp. 1251-1253, 2000.

Olofsson et al., "Cytokeratin-18 is a useful serum biomarker for early determination of response of breast carcinomas to chemotherapy," Clinical Cancer Research, vol. 13, No. 11, pp. 3198-3206, 2007.

Ong et al., "Stable isotope labeling by amino acids in cell culture, SILAC, as a simple and accurate approach to expression proteomics," Molecular & Cellular Proteomics, vol. 1, No. 5, pp. 376-386, 2002.

Orchard et al., "The MIntAct project—IntAct as a common curation platform for 11 molecular interaction databases," Nucleic Acids Research, vol. 42, (Database issue), pp. D358-D363, 2014.

Oshima, "Apoptosis and keratin intermediate filaments," Cell Death & Differentiation, vol. 9, No. 5, pp. 486-492, 2002.

Pandita, et al., "Chromatin remodeling finds its place in the DNA double-strand break response," Nucleic Acids Research, vol. 37, No. 5, pp. 1363-1377, 2009.

Park et al., "Mechanism of anchoring of OmpA protein to the cell wall peptidoglycan of the gram-negative bacterial outer membrane," FASEB Journla, vol. 26, No. 1, pp. 219-228, 2012.

Parry et al., "Towards a molecular description of intermediate filament structure and assembly," Experimental Cell Research, vol. 313, No. 10, pp. 2204-2216, 2007.

Patel et al., "Convergent evolution of escape from hepaciviral antagonism in primates," PLoS Biology, vol. 10, No. 3, e1001282, 2012.

Petersen et al., "SignalP 4.0: discriminating signal peptides from transmembrane regions," Nature Methods, vol. 8, No. 10, pp. 785-786, 2011.

Peterson, et al., "Intestinal epithelial cells: regulators of barrier function and immune homeostasis," Nature Reviews Immunology, vol. 14, No. 3, pp. 141-153, 2014.

Petrotchenko et al., "An isotopically coded CID-cleavable biotinylated cross-linker for structural proteomics," Molecular & Cellular Proteomics, vol. 10, No. 2, pp. M110.001420, 2011.

Petrotchenko, et al., "Crosslinking combined with mass spectrometry for structural proteomics," Mass Spectrometry Reviews, vol. 29, No. 6, pp. 862-876, 2010.

Planas-Iglesias et al., "Understanding protein-protein interactions using local structural features," Journal of Molecular Biology, vol. 425, No. 7, pp. 1210-1224, 2013.

Pommier et al., "Topoisomerase I inhibitors: selectivity and cellular resistance," Drug Resistance Updates, vol. 2, No. 5, pp. 307-318, 1999.

Pommier, "Topoisomerase I inhibitors: camptothecins and beyond," Nature Reviews Cancer, vol. 6, No. 10, pp. 789-802, 2006.

Prasad et al., et al. "Morphogenic regulator EFG1 affects the drug susceptibilities of pathogenic Candida albicans," FEMS Yeast Research, vol. 10, No. 5, pp. 587-596, 2010.

Puig et al., "The tandem affinity purification (TAP) method: a general procedure of protein complex purification," Methods, vol. 24, No. 3, pp. 218-229, 2001.

Ramos et al., "Characterisation of a new Leishmania META gene and genomic analysis of the META cluster," FEMS Microbiology Letters, vol. 238, No. 1, pp. 213-219, 2004.

Rappsilber, "The beginning of a beautiful friendship: cross-linking/mass spectrometry and modelling of proteins and multi-protein complexes," Journal of Structural Biology, vol. 173, No. 3, pp. 530-540, 2011.

Rasheed, et al., "Mechanisms of resistance to topoisomerase I-targeting drugs," Oncogene, vol. 22, No. 47, pp. 7296-7304, 2003.

Rawling et al., "Epitope mapping of the Pseudomonas aeruginosa major outer membrane porin protein OprF," Infection and Immunity, vol. 63, No. 1, pp. 38-42, 1995.

Rawling et al., "Roles of the carboxy-terminal half of Pseudomonas aeruginosa major outer membrane protein OprF in cell shape, growth in low-osmolarity medium, and peptidoglycan association," Journal of Bacteriology, vol. 180, No. 14, pp. 3556-3562, 1998.

Robert, "Subcomplexes from the Xcp secretion system of Pseudomonas aeruginosa," FEMS Microbiology Letters, vol. 252, No. 1, pp. 43-50, 2005.

Robinson et al., "The molecular sociology of the cell," Nature, vol. 450, No. 7172, pp. 973-982, 2007.

Rosenstein, "Cystic fibrosis," Lancet, vol. 351, No. 9098, pp. 277-282, 1998.

Rottner et al., "Bacteria-host-cell interactions at the plasma membrane: stories on actin cytoskeleton subversion," Developmental Cell, vol. 9, No. 1, pp. 3-17, 2005.

Roy et al., "I-TASSER: a unified platform for automated protein structure and function prediction," Nature Protocols, vol. 5, 4, pp. 725-738, 2010.

Sahni et al., "Edgotype: a fundamental link between genotype and phenotype," Current Opinion in Genetics & Development, vol. 23, No. 6, pp. 649-657, 2013.

Salton et al., "Involvement of Matrin 3 and SFPQ/NONO in the DNA damage response," Cell Cycle, vol. 9, No. 8, pp. 1568-1576, 2010.

Schweizer et al., "New consensus nomenclature for mammalian keratins," Journal of Cell Biology, vol. 174, No. 2, pp. 169-174, 2006.

Shapira, et al., "A physical and regulatory map of host-influenza interactions reveals pathways in H1N1 infection," Cell, vol. 139, No. 7, pp. 1255-1267, 2009.

(56) References Cited

OTHER PUBLICATIONS

Shu et al., "Core structure of the outer membrane lipoprotein from *Escherichia coli* at 1.9 A resolution," Journal of Molecular Biology, vol. 299, No. 4, pp. 1101-1112, 2000.

Singh et al., "Chemical cross-linking and mass spectrometry as a low-resolution protein structure determination technique," Analytical Chemistry, vol. 82, No. 7, pp. 2636-2642, 2010.

Sinz, "Chemical cross-linking and mass spectrometry for mapping three-dimensional structures of proteins and protein complexes," Journal of Mass Spectrometry, vol. 38, No. 12, pp. 1225-1237, 2003.

Sinz, "Chemical cross-linking and mass spectrometry to map three-dimensional protein structures and protein-protein interactions," Mass Spectrometry Reviews, vol. 25, No. 4, pp. 663-682, 2006.

Snider, et al., "Post-translational modifications of intermediate filament proteins: mechanisms and functions," Nature Reviews Molecular Cell Biology, vol. 15, No. 3, pp. 163-177, 2014.

Soderblom, et al., "Collision-induced dissociative chemical cross-linking reagents and methodology: applications to protein structural characterization using tandem mass spectrometry analysis," Analytical Chemistry, vol. 78, No. 23, pp. 8059-8068, 2006.

Soiferman et al., "The effect of small molecules on nuclear-encoded translation diseases," Biochimie, vol. 100, pp. 184-191, 2014.

Sowa et al., "Defining the human deubiquitinating enzyme interaction landscape," Cell, vol. 138, No. 2, pp. 389-403, 2009.

Stanley, et al., "Pemphigus, bullous impetigo, and the staphylococcal scalded-skin syndrome," New England Journal of Medicine, vol. 355, No. 17, pp. 1800-1810, 2006.

Stoetzer et al., "Prediction of response to neoadjuvant chemotherapy in breast cancer patients by circulating apoptotic biomarkers nucleosomes, DNAse, cytokeratin-18 fragments and surviving," Cancer Letters, vol. 336, No. 1, pp. 140-148, 2013.

Sugawara et al., "Pseudomonas aeruginosa porin OprF exists in two different conformations," Journal of Biological Chemistry, vol. 281, No. 24, pp. 16220-16229, 2006.

Sugimoto et al., "Decreased expression of DNA topoisomerase I in camptothecin-resistant tumor cell lines as determined by a monoclonal antibody," Cancer Research, vol. 50, No. 21, pp. 6925-6930, 1990.

Sugimoto et al., "Elevated expression of DNA topoisomerase II in camptothecin-resistant human tumor cell lines," Cancer Research, vol. 50, No. 24, pp. 7962-7965, 1990.

Swanson, et al., "Phagocytosis by zippers and triggers," Trends in Cell Biology, vol. 5, No. 3, pp. 89-93, 1995.

Takara et al., "Molecular changes to HeLa cells on continuous exposure to SN-38, an active metabolite of irinotecan hydrochloride," Cancer Letters, vol. 278, No. 1, pp. 88-96, 2009.

Tange et al., "Biochemical analysis of the EJC reveals two new factors and a stable tetrameric protein core," RNA, vol. 11, No. 12, pp. 1869-1883, 2005.

Tarassov et al., "An in vivo map of the yeast protein interactome," Science, vol. 320, No. 5882, pp. 1465-1470, 2008.

Tosi et al., "Structure and subunit topology of the INO80 chromatin remodeler and its nucleosome complex," Cell, vol. 154, No. 6, pp. 1207-1219, 2013.

Trnka et al., "Matching cross-linked peptide spectra: only as good as the worse identification," Molecular and Cellular Proteomics, vol. 13, No. 2, pp. 420-434, 2014.

Tsukazaki et al., "Structure and function of a membrane component SecDF that enhances protein export," Nature, vol. 474, No. 7350, pp. 235-238, 2011.

Tsurutani et al., "Point mutations in the topoisomerase I gene in patients with non-small cell lung cancer treated with irinotecan," Lung Cancer, vol. 35, No. 3, pp. 299-304, 2002.

Turner, "Reading signals on the nucleosome with a new nomenclature for modified histones," Nature Structural & Molecular Biology, vol. 12, No. 2, pp. 110-112, 2005.

Uliana et al., "Leishmania: overexpression and comparative structural analysis of the stage-regulated meta 1 gene," Experimental Parasitology, vol. 92, No. 3, pp. 183-191. 1999.

Valot et al., "MassChroQ: a versatile tool for mass spectrometry quantification," Proteomics, vol. 11, No. 17, pp. 3572-3577, 2011.

van Schilfgaarde et al., "Paracytosis of Haemophilus influenzae through cell layers of NCI-H292 lung epithelial cells," Infection and Immunity, vol. 63, No. 12, pp. 4729-4737, 1995.

\* cited by examiner

Formula Weight : 1292.26(5)
Exact Mass : 1291.42335219(4)
Formula : $C_{66}H_{65}N_7O_{21}$
Composition : C 61.3% H 5.1% N 7.6% O 26.0%

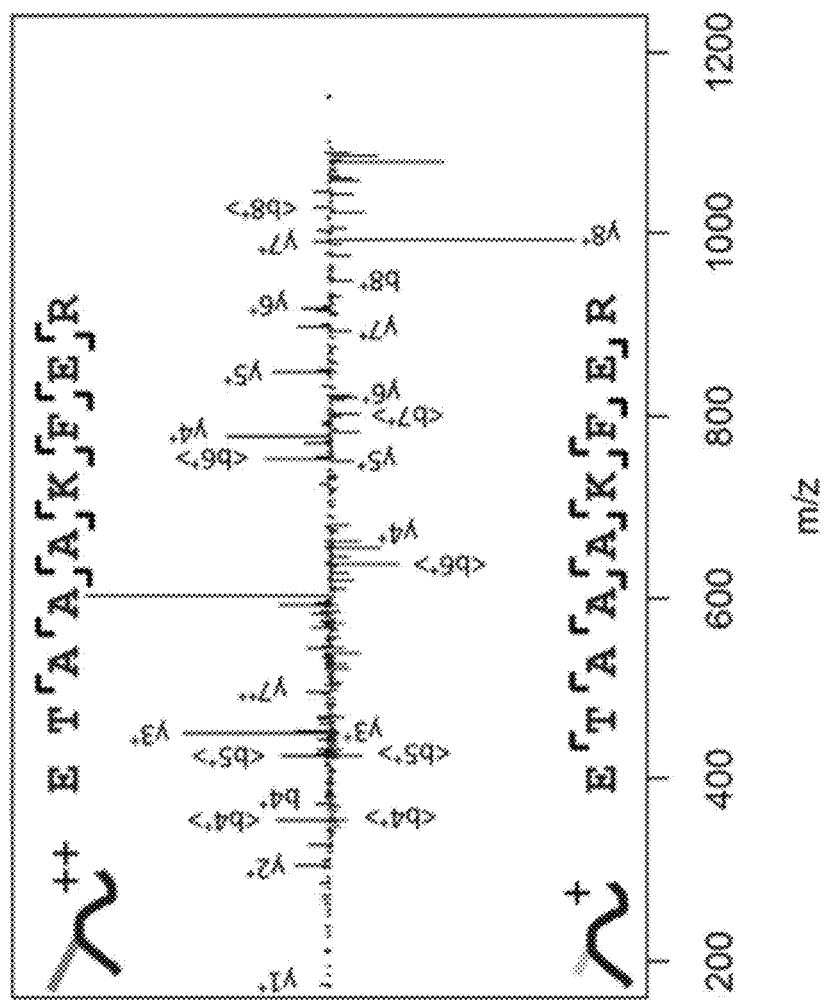

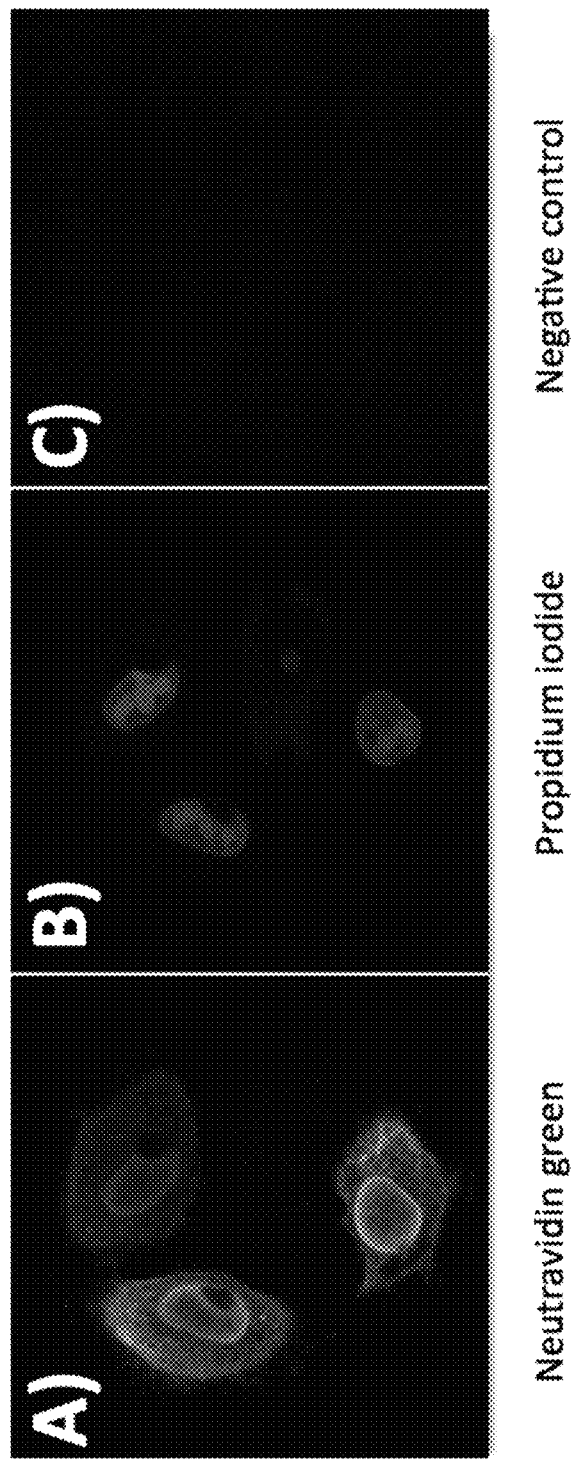

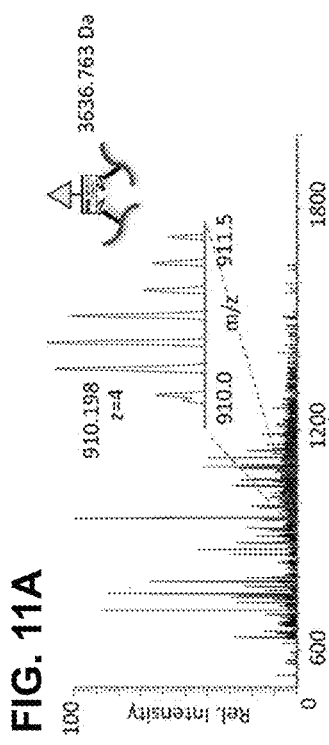
FIG. 11A
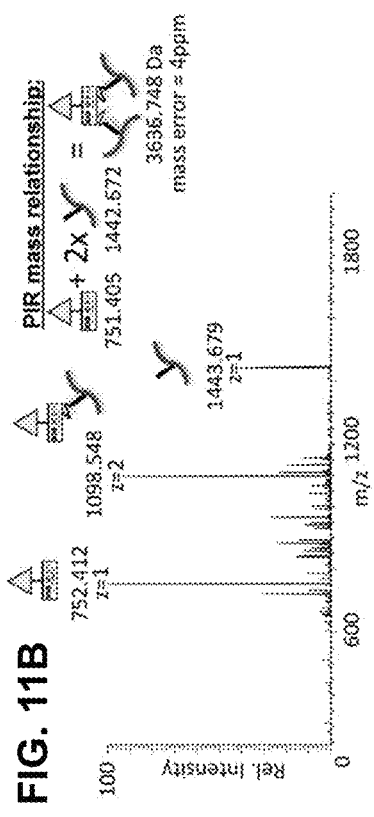
FIG. 11B
FIG. 11C
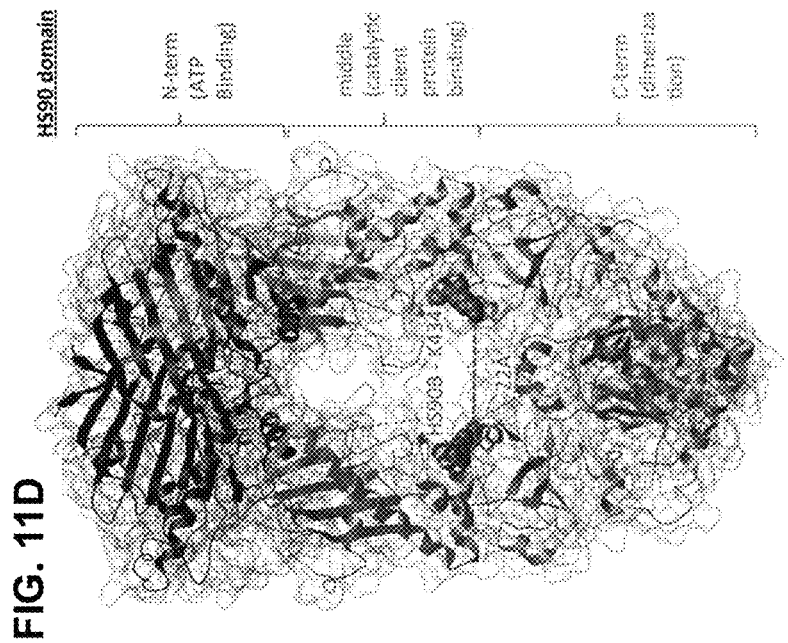
FIG. 11D
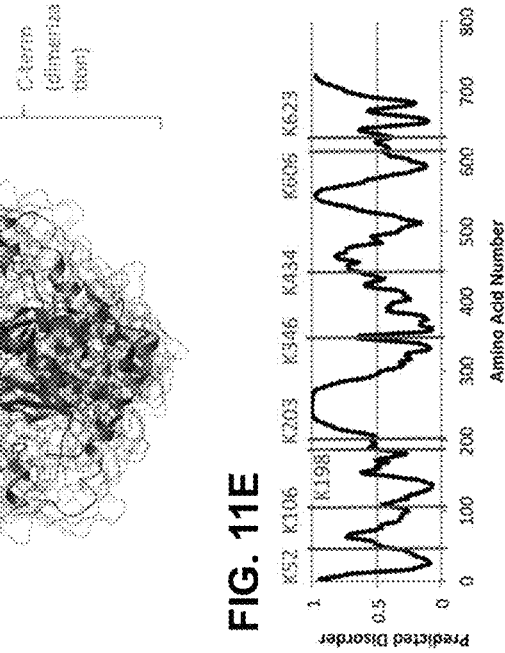
FIG. 11E

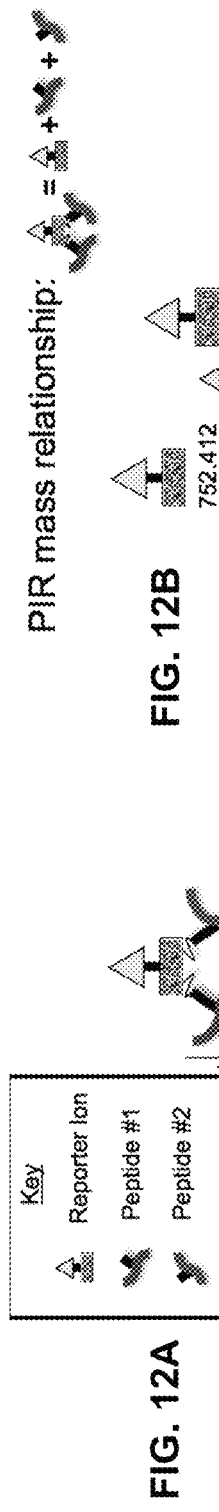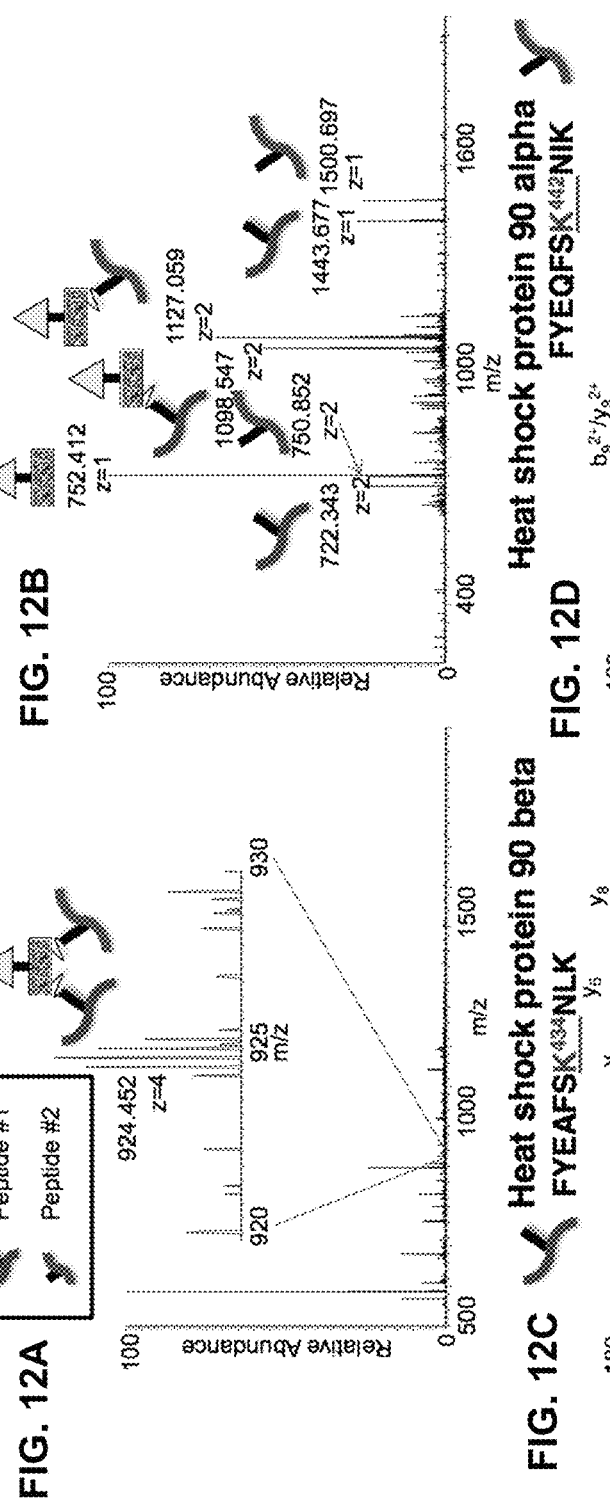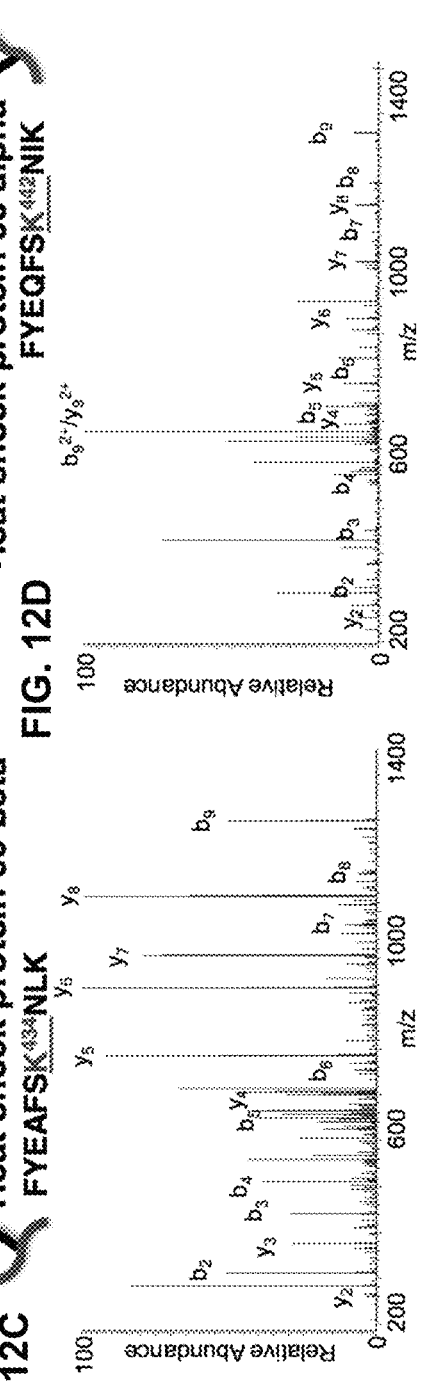
FIG. 12A
FIG. 12B
FIG. 12C
FIG. 12D

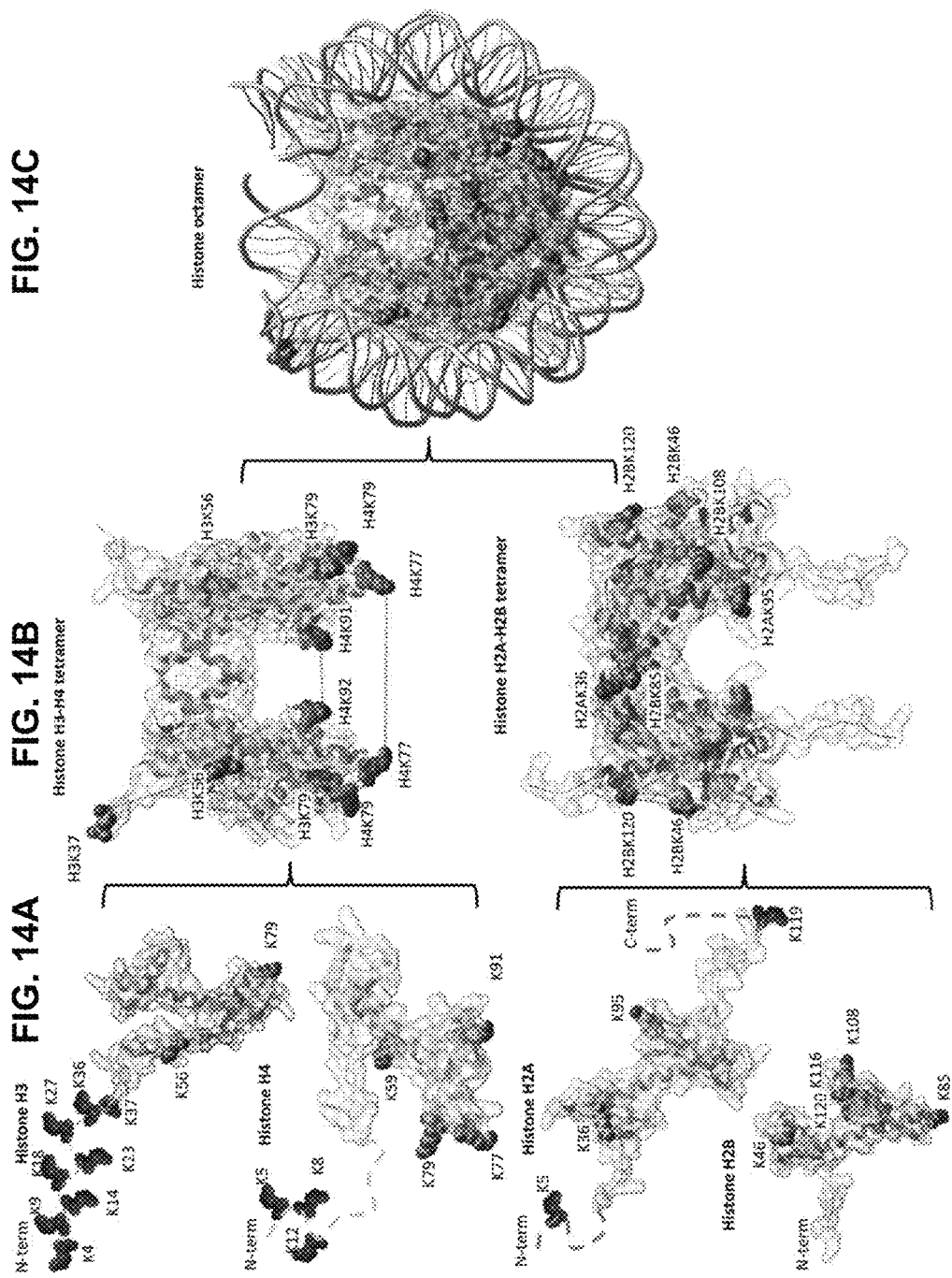
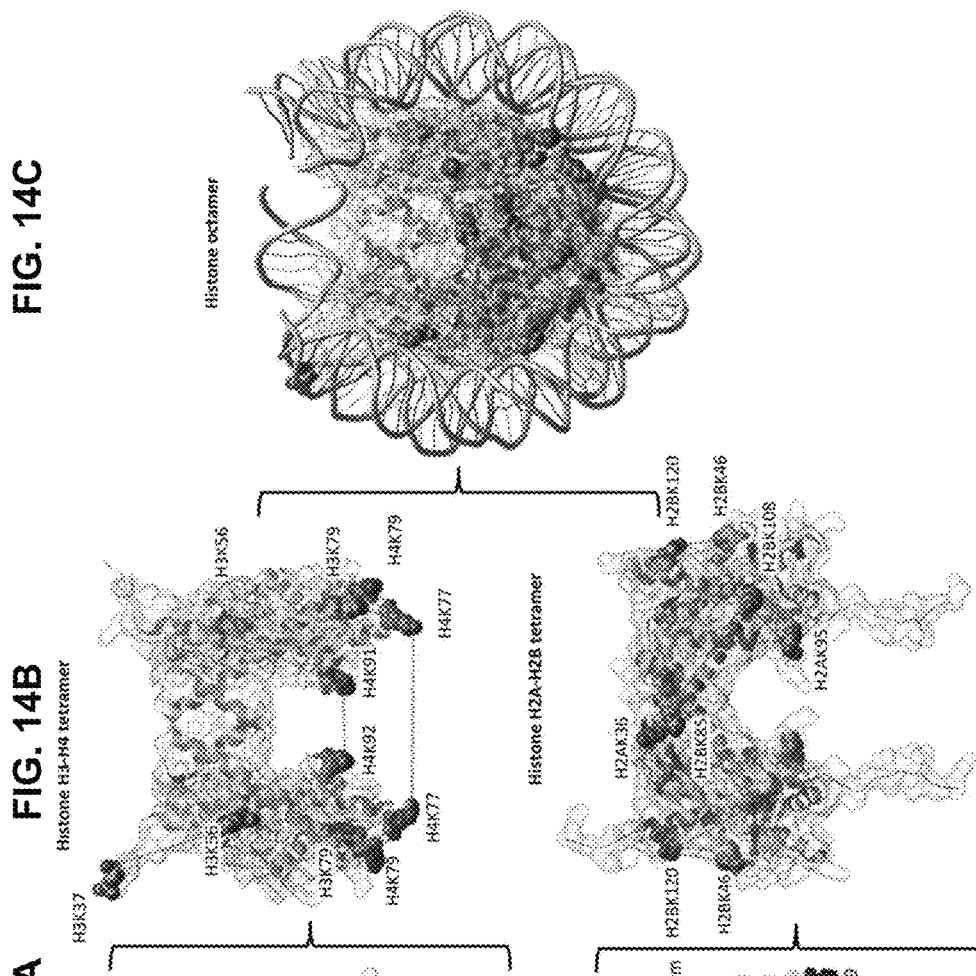
FIG. 14A  FIG. 14B  FIG. 14C

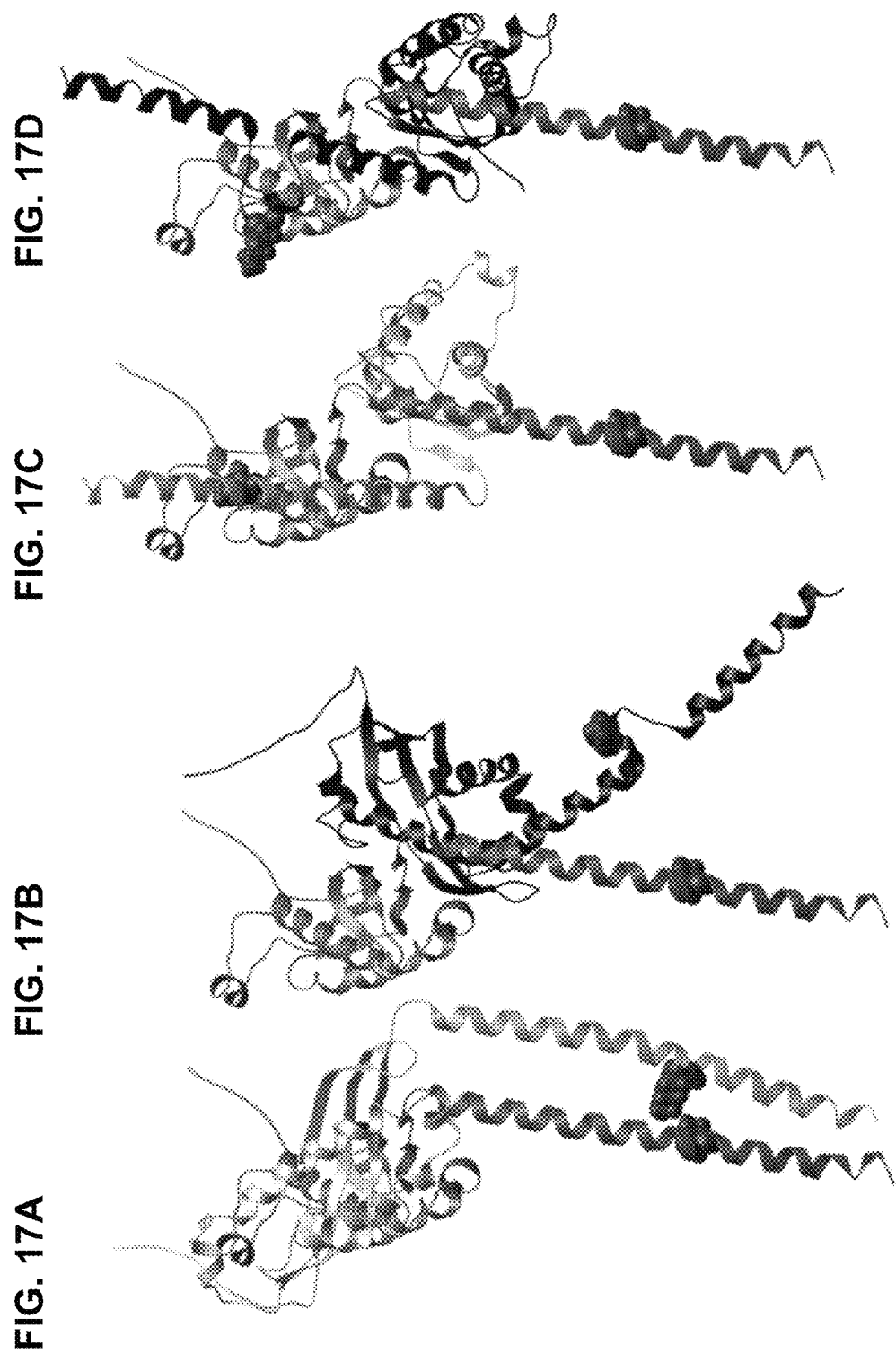

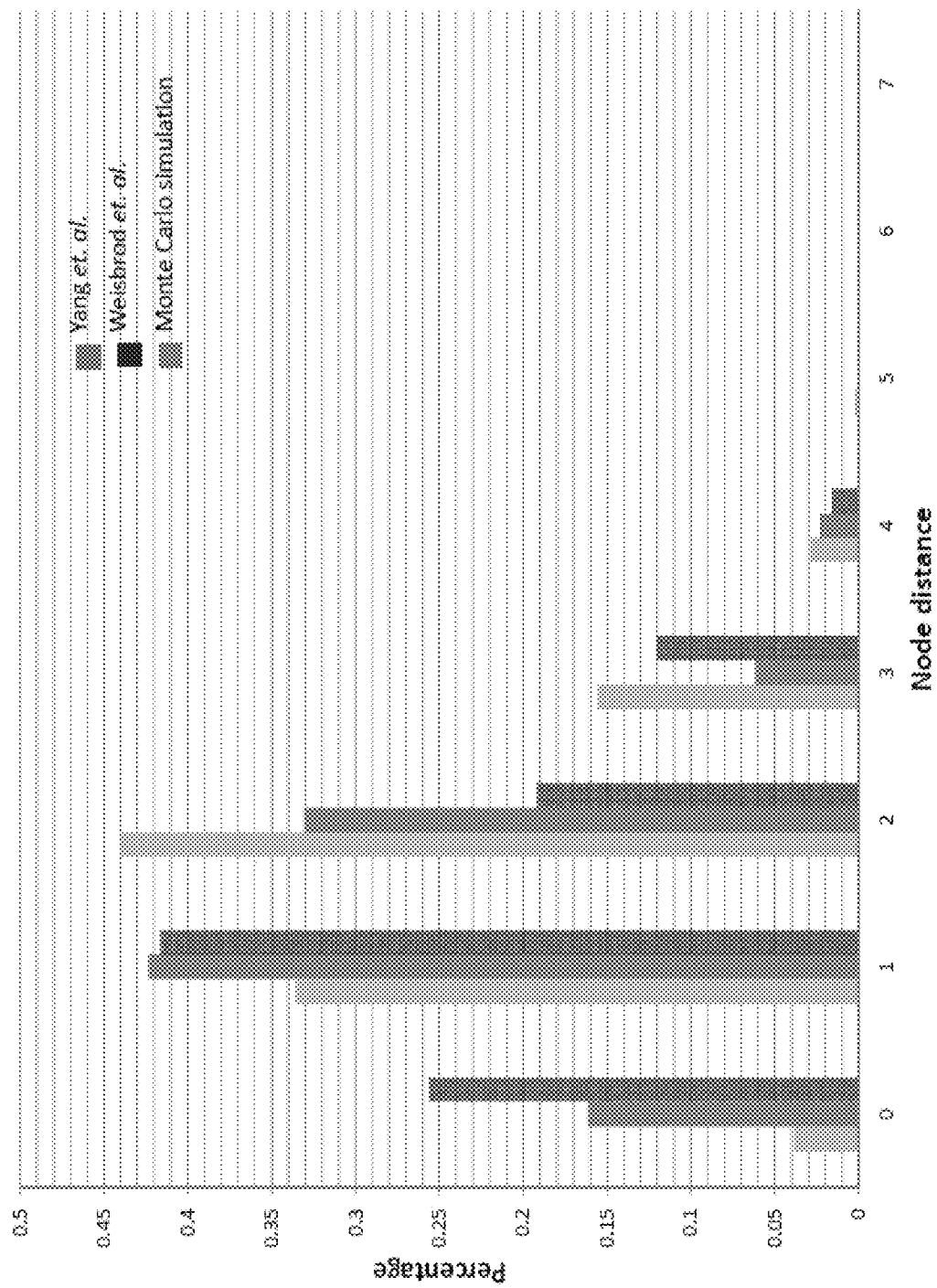

REAL-TIME ANALYSIS FOR CROSS-LINKED PEPTIDES

This application claims the benefit of U.S. Provisional Application No. 61/825,901, filed May 21, 2013, the disclosure of which is explicitly incorporated herein by reference in its entirety.

STATEMENT REGARDING FEDERALLY SPONSORED RESEARCH

This invention was made with government support under 5R01GM097112 and 5R01GM086688 awarded by the National Institutes of Health. The government has certain rights in the invention.

BACKGROUND

Proteins are the principal operatives within cells, involved in carrying out essentially all biological functions. A complex network of intra- and intermolecular interactions, post-translational modifications and abundance levels is required to maintain the delicate balance of function essential for life. Subtle changes within this network can give rise to specific biological responses to environmental factors, onset of disease, normal aging, and other biological processes. Therefore, direct experimental observation of protein structures and interactions in relation to biological function is paramount to improved understanding of living systems.

The versatility of protein function has its origins in topological shapes and features that these polymeric macromolecules can adopt. Moreover, the crowded intracellular environment profoundly influences their shape such that proteins that appear unstructured in vitro can adopt a more defined conformation inside cells. These induced topological features occur as a consequence of interaction within cellular compartments that may not be replicated in cell lysates or purified components.

Thus, there is a need in the art for methods that can reveal information about global protein topology under physiologically relevant conditions within native interactions and with intended partners inside cells, and a further need for methods that can do so with high sensitivity, specificity, and efficiency on a large scale.

SUMMARY

The present invention provides certain advantages and advancements over the prior art. In particular, the present disclosure provides methods for large-scale, high-throughput identification of protein-protein interactions and the topologies thereof under physiologically relevant conditions.

In one aspect, the disclosure provides methods for identifying one or a plurality of interacting peptides within a biological system, comprising: (a) obtaining a population of cross-linked precursor peptides produced by digestion of a population of proteins cross-linked with a cleavable protein interaction reporter (PIR) cross-linker; (b) subjecting the population of cross-linked precursor peptides to mass spectrometry (MS) to produce precursor ions; (c) subjecting precursor ions with a charge state equal to or greater than a cutoff charge state to conditions under which the cleavable PIR cross-linker is cleaved, thereby producing a population of released peptides and cleaved reporter ions; and (d) analyzing the population of released peptides to identify interacting peptides, wherein identifying interacting peptides comprises identifying released peptides that, when added to the mass of the reporter ion, have a combined mass equal to the mass of the corresponding precursor ion.

In another aspect, the disclosure provides methods of identifying a candidate compound for treating cancer comprising: (a) contacting a peptide pair from the group consisting of:

(i)
FYEQFSKNIK, (SEQ ID NO: 1)
FYEQFSKNIK; (SEQ ID NO: 1)

(ii)
FYEAFSKNLK, (SEQ ID NO: 2)
FYEAFSKNLK; (SEQ ID NO: 2)

(iii)
FYEQFSKNIK, (SEQ ID NO: 1)
FYEAFSKNLK; (SEQ ID NO: 2)

(iv)
FYEQFSKNIK, (SEQ ID NO: 1)
KHLEINPDHPIVETLR; (SEQ ID NO: 3)

(v)
APFDLFENKK, (SEQ ID NO: 4)
FYEQFSKNIK; (SEQ ID NO: 1)

(vi)
FYEQFSKNIK, (SEQ ID NO: 1)
KAAALEAMK; (SEQ ID NO: 5)
and (vii)
FYEAFSKNLK, (SEQ ID NO: 2)
KAAALEAMK; (SEQ ID NO: 5)

with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating cancer.

In another aspect, the disclosure provides methods of identifying a candidate compound for treating an antibiotic-resistant infection comprising: (a) contacting a peptide pair comprising KINLYGNALSR (SEQ ID NO: 6) and NDIAPYLGFGFAPKINK (SEQ ID NO: 7) with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating an antibiotic-resistant infection.

In another aspect, the disclosure provides methods of identifying a candidate compound for treating *A. baumannii* infection comprising: (a) contacting a peptide pair from the group consisting of:

(i)
VFFDTNKSNIKDQYKPEIAK, (SEQ ID NO: 8)

MSAAEAVKEK; (SEQ ID NO: 9)

(ii)
TKEGR, (SEQ ID NO: 10)

MSAAEAVKEK; (SEQ ID NO: 9)
and (iii)
LSTQGFAWDQPIADNKTK, (SEQ ID NO: 11)

MSAAEAVKEK; (SEQ ID NO: 9)

with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating *A. baumannii* infection.

In another aspect, the disclosure provides cleavable protein interaction reporter (PIR) cross-linkers comprising formula (I):

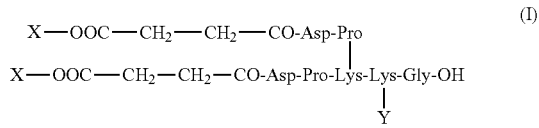

(SEQ ID NO: 27) wherein X is H, succinimid-N-yl, or phthalimid-N-yl; and Y is H or a capture moiety.

In another aspect, a method is provided. A computing device receives data representing a first protein structure. The computing device receives data representing a second protein structure. The computing device receives data representing an interaction between the first protein structure and the second protein structure. The computing device generates a display. The display is configured to show at least a portion of: the first protein structure, the second protein structure, and the interaction between the first protein structure and the second protein structure.

In another aspect, a computing device is provided. The computing device includes a processor and a tangible computer-readable medium. The tangible computer-readable medium is configured to include comprise instructions that, when executed by the processor, are configured to cause the computing device to perform functions. The functions include: receiving data representing a first protein structure; receiving data representing a second protein structure; receiving data representing an interaction between the first protein structure and the second protein structure; and generating a display, where the display is configured to show at least a portion of: the first protein structure, the second protein structure, and the interaction between the first protein structure and the second protein structure.

In another aspect, a tangible computer-readable medium is provided. The tangible computer-readable medium is configured to include comprise instructions that, when executed by a processor of a computing device, are configured to cause the computing device to perform functions. The functions include: receiving data representing a first protein structure; receiving data representing a second protein structure; receiving data representing an interaction between the first protein structure and the second protein structure; and generating a display, where the display is configured to show at least a portion of: the first protein structure, the second protein structure, and the interaction between the first protein structure and the second protein structure.

In another aspect, a device is provided. The device includes: means for processing; means for receiving data representing a first protein structure; means for receiving data representing a second protein structure; means for receiving data representing an interaction between the first protein structure and the second protein structure; and means for generating a display using the processing means, where the display is configured to show at least a portion of: the first protein structure, the second protein structure, and the interaction between the first protein structure and the second protein structure.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, in which:

FIG. 2A: Biotin Aspartate Proline N-Hydroxyphlalamide (BDP-NHP). FIG. 2B: Biotin Rink N-Hydroxysuccinimide (BRink-NHS). FIG. 2C: Rink N-Hydroxysuccinimide (2Rink-NHS).

FIG. 3 presents example MS, MS$^2$, and MS$^3$ spectra of a cross-linked homodimer peptide pair (K.GNGKSSDPAGSFR.V (SEQ ID NO: 12)) to demonstrate this capability.

FIGS. 4A-4C. FIG. 4A: High resolution MS$^2$ spectra acquired on a cross-linked species with two different cross-linkers within the same LC-ReACT experiment. The cross-linked site identified involves the same two peptides from RNase A (ETAAAKFER (SEQ ID NO: 13) and NLTKDR (SEQ ID NO: 14)). The top contains this site identified with BDP cross-linker, and the bottom contains this site identified with 2Rink cross-linker. Low resolution MS$^3$ used to make peptide sequence identification for NLTKDR (SEQ ID NO: 14) (FIG. 4B) and ETAAAKFER (SEQ ID NO: 13) (FIG. 4C) for both linkers.

FIG. 5A: High resolution MS¹ acquisition for precursor information; inset is an expanded view of the spectrum surrounding the cross-linked peptide precursor, 718.174 m/z. FIG. 5B High resolution MS² acquisition for cross-linked peptide relationship information. FIGS. 5C-5D: Low resolution MS³ acquisition for peptide sequence information (HFTAKLK (SEQ ID NO: 15); GLTFTYEPKVLR (SEQ ID NO: 16)). FIG. 5E: Tryptophanase crystal structure (*E. coli*, PDB: 2OQX) with all observed cross-links marked in grey; the cross-link observed in this data is marked in red, while other sites we observe in additional relationships are in grey.

FIG. 6A: A breakdown of the type of cross-links observed from *E. coli* (inter-protein, intra-protein, or unambiguous homodimer). FIG. 6B: Protein localization of proteins identified in cross-linked peptide pairs from *E. coli*. FIG. 6C: Protein interaction network constructed from all cross-links observed within *E. coli* cell experiments. FIGS. 6D-6F: Same information for HeLa cells.

FIGS. 10A-10C. Confocal microscopy images of PIR labeled HeLa cells. FIG. 10A: neutravidin green staining; FIG. 10B: propidium iodide staining; FIG. 10C: negative control.

FIG. 11A: Precursor FT-ICR mass spectrum for with inset illustrating the 4+ isotope distribution at m/z 910.198 for the homodimer cross-linked peptide pair. FIG. 11B: High resolution MS² spectrum for cross-linked peptide pair indicating released peptide and reporter ions. FIG. 11C: Ion trap MS³ spectrum used to identify peptide FYEAFSKNLK (SEQ ID NO: 2) from HS90B. FIG. 11D: Crystal structure for the yeast HSP90 dimer (PBD: 2CG9) highlighting position of cross-linked lysine 434 from HS90B near the interface of the middle and C-terminal domains (note: particular lysine residue is conserved between yeast and human although appears as K423 in yeast crystal structure). FIG. 11E: Predicted disorder plot (generated using VSL2 disorder prediction algorithm) for HS90B indicating presence of K434 near a transition between order and disordered region.

FIG. 12A-12D. Mass spectra identifying the hetero-dimer cross-link between heat shock protein 90-alpha and heat shock protein 90-beta (peptides FYEAFSKNLK (SEQ ID NO: 2); FYEQFSKNIK (SEQ ID NO: 1).

FIGS. 14A-14C. Cross-links mapped onto structure of nucleosome (PDB: 3AFA). FIG. 14A: Individual monomer structures of the four core histone proteins with cross-linker reactive lysine residues highlighted in space filling display. N-terminal and C-terminal tails not present in the crystal structure were drawn in manually (indicated by dashed lines) to illustrate cross-linked sites in these highly disordered regions. FIG. 14B: Tetramer structures for H32-H42 and H2A2-H2B2 with intraprotein and interprotein cross-links displayed as dashed lines. FIG. 14C: Complete nucleosome particle including 137 bp DNA wrapped around histone octamer complex with cross-links displayed.

FIGS. 17A-17D. Comparison of models for PHB-PHB homodimer, and PHB-PHB2 heterodimer for which cross-linking distance constraints were applied (FIGS. 17A and 17B) and were not applied (FIGS. 17C and 17D).

FIG. 18A: Protein kinase a holoenzyme structure (R2C2) assembled from known crystallographic and cross-linking data. Cross-links obtained using REACT are shown through denoting the lysine in the primary sequence which was found labeled and shown in space-filling form. The section between the two crystallized regions is displayed as a dotted line, because no spatial experimental data is available. However, cross-linking data obtained supports close proximity of the disorder linker region between the N-terminal and C-terminal regions with existing crystallographic data. FIG. 18B: RIα dimer upon binding with cAMP and release of the catalytic subunits.

FIG. 23 depicts a distribution of the node distances observed in cross-linked peptide data sets from cell lysates and intact cells as determined from the E. coli protein interaction database EciD, in accordance with an example embodiment.

Figure 1:
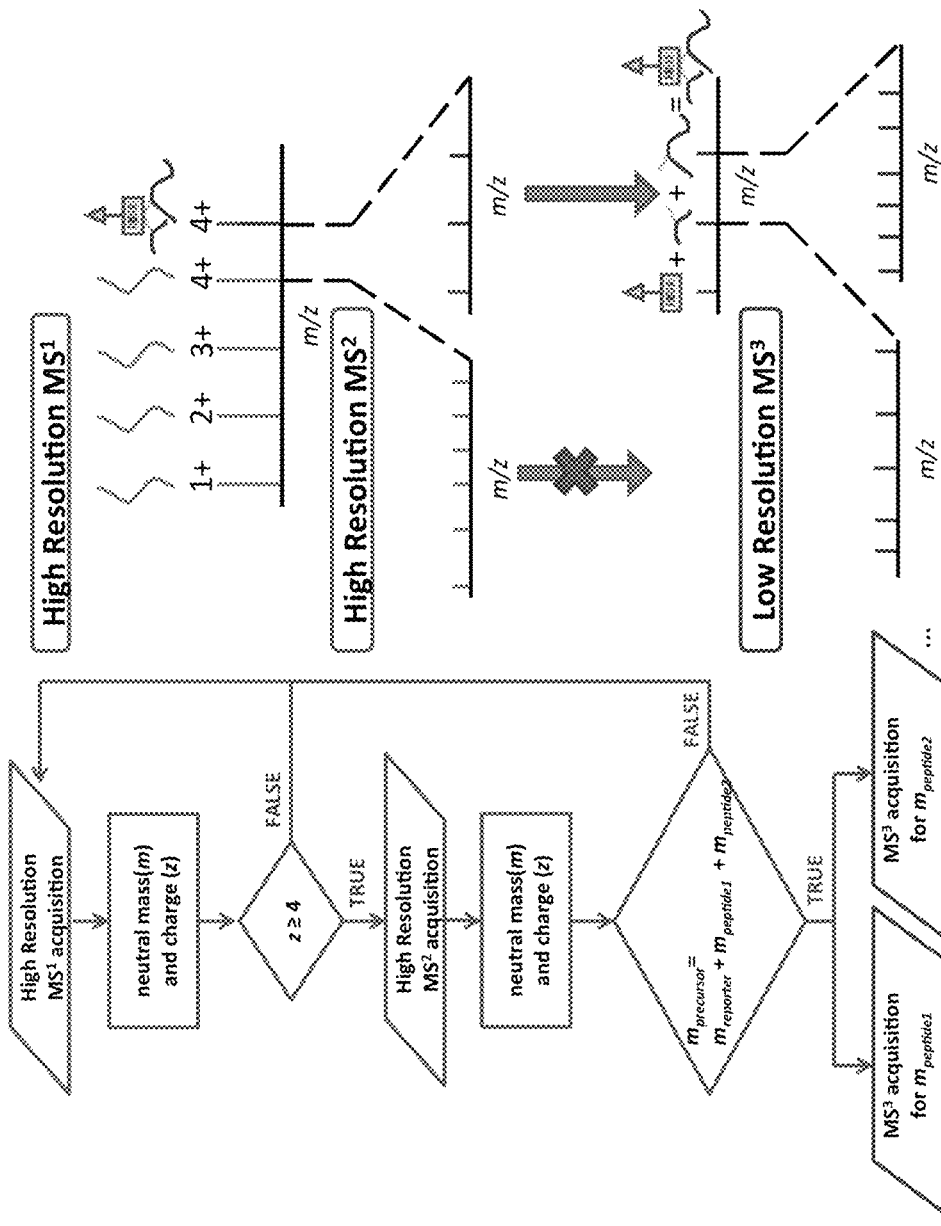
FIG. 1 shows, at left, a flow chart depicting an LC-MS algorithm functions during LC-MS experiments. At right is an idealized practical diagram of how the algorithm would operate on real data directly corresponding to the flow chart.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present invention.

DETAILED DESCRIPTION

All publications, patents, and patent applications cited herein are hereby expressly incorporated by reference for all purposes.

Before describing the present invention in detail, a number of terms will be defined. As used herein, the singular forms "a", "an", and "the" include plural referents unless the context clearly dictates otherwise. For example, reference to a "protein" means one or more proteins.

It is noted that terms like "preferably", "commonly", and "typically" are not used herein to limit the scope of the claimed invention or to imply that certain features are critical, essential, or even important to the structure or function of the claimed invention. Rather, these terms are merely intended to highlight alternative or additional features that can or cannot be used in a particular embodiment of the present invention.

For the purposes of describing and defining the present invention it is noted that the term "substantially" is used herein to represent the inherent degree of uncertainty that can be attributed to any quantitative comparison, value, measurement, or other representation. The term "substantially" is also used herein to represent the degree by which a quantitative representation can vary from a stated reference without resulting in a change in the basic function of the subject matter at issue.

All embodiments of the invention can be used in combination with any other embodiment(s) of any aspect of the invention unless the context clearly indicates otherwise.

In one aspect, the disclosure provides methods for identifying one or a plurality of interacting peptides within a biological system, comprising: (a) obtaining a population of cross-linked precursor peptides produced by digestion of a population of proteins cross-linked with a cleavable protein interaction reporter (PIR) cross-linker; (b) subjecting the population of cross-linked precursor peptides to mass spectrometry (MS) to produce precursor ions; (c) subjecting precursor ions with a charge state equal to or greater than a cutoff charge state to conditions under which the cleavable PIR cross-linker is cleaved, thereby producing a population of released peptides and cleaved reporter ions; and (d) analyzing the population of released peptides to identify interacting peptides, wherein identifying interacting peptides comprises identifying released peptides that, when added to the mass of the reporter ion, have a combined mass equal to the mass of the corresponding precursor ion.

The methods of the invention are useful, for example, to identify cross-linked peptide pairs using mass spectrometry cleavable cross-linkers that are directly integrated into the mass spectral acquisition. These methods, provide significant improvement over current detection and identification limits of cross-linked peptide pairs by focusing the analysis time and instrument duty cycle on those ions which specifically meet the mass relationships engineered in PIR chemical cross-linkers or similar molecules. Operational time is reduced by not having to perform post-acquisition data analysis beyond that of a proteome database search. The methods of the invention are compatible for use with any mass spectrometry cleavable cross-linker. The methods of the invention facilitate studies using a wide range of cross-linker chemistries for PPI and topology interrogation within complex biological systems, and as shown, even in human cells. The methods of the invention enable large-scale identification of cross-linked species from cells, on the order of 1000 s of cross-linked species, which represents a 10- to 100-fold improvement over any previous method. With these methods, proteome-wide PPI identification and topological analyses are possible.

As used herein, the term "protein interaction reporter" ("PIR") refers to any cleavable cross-linker that can yield expected mass relationships between a cross-linked precursor and the peptides released after cleavage of the PIR.

As used herein, the terms "polypeptide," "protein," and "peptide" all refer to a chain, usually unbranched, of amino acid monomers linked by peptide bonds. Typically, "peptide" refers to a protein fragment or small protein of less than about 100 amino acids in length. As used herein, the terms "residue" and "protein residue" are interchangeable and refer to an amino acid that is bonded with other amino acids by one or more peptide bonds within a protein.

As used herein, the term "MS$^n$" refers to a mass spectrometry (MS) analysis of order n. Thus, MS$^1$ refers to a first mass spectrometric analysis (e.g. the first quadrupole) in a multi-stage mass spectrometer; MS$^2$ refers to a second stage of mass spectrometric analysis; and MS$^3$ refers to a third stage of mass spectrometric analysis. As used herein, the terms "MS/MS" and "tandem mass spectrometry" are interchangeable and refer to mass spectrometric analysis with two stages. As used herein, the term "MS/MS/MS" refers to mass spectrometric analysis with three stages. For any stage of mass spectrometry, any suitable type of ion source can be used with the methods and compositions disclosed herein, including but not limited to electrospray ionization (ESI), electron impact ionization (EI), fast atom bombardment (FAB), chemical ionization (CI), atmospheric pressure chemical ionization (AFCI), and matrix-assisted laser desorption/ionization (MALDI). For any stage of mass spectrometry, any suitable type of mass analyzer can be used with the methods and compositions disclosed herein, including but not limited to time-of-flight (TOF) analyzers, quadrupole mass analyzers, ion traps, quadrupole ion traps (three-dimensional, linear, or toroidal), cylindrical ion traps, orbitraps, and Fourier transform ion cyclotron resonance analyzers.

As used herein, the term "protein-protein interaction" ("PPI") refers to physical contacts established between two or more proteins as a result of biochemical events and/or electrostatic forces.

As used herein, the term "topology" or "topological" refers to the geometric and spatial information regarding the interaction between two proteins. In the case where two proteins interact, topological information can include the amino acid residues of each protein that interact, the orientation of the interacting proteins with respect to one another, the orientation of the interacting amino acid residues with respect to one another or with respect to the proteins, three-dimensional structures of the protein surfaces that interact, the sites on the overall three dimensional protein structures governing the interaction, etc.

As used herein, the term "digest" or "digestion" refers to any means, such as proteolysis or proteolytic digestion, of splitting or degrading a protein into smaller peptide fragments. Many enzymes are capable of digesting proteins. These proteolytic enzymes (proteases) are commonly divided into six broad groups: serine proteases, threonine proteases, cysteine proteases, aspartate proteases, glutamic acid proteases, and metalloproteases. Examples of proteases commonly used in conjunction with mass spectrometry include trypsin (which cleaves the carboxyl side of arginine and lysine residues), LysN (which cleaves the amino side of lysine residues), LysC (which cleaves the carboxyl side of lysine residues), GluC (which cleaves the carboxyl side of glutamate), AspN (which cleaves the amino side of aspartate residues), and chymotrypsin (which cleaves the carboxyl side of tyrosine, phenylalanine, tryptophan and leucine).

As used herein, the term "cross-link" refers to a bond, usually a covalent bond, that links one biopolymer chain, such as a protein chain, to another. As used herein, the terms "cross-linking reagent," "cross-linking agent," or "cross-linker" are interchangeable and refer to a reagent or set of reagents capable of chemically linking two molecules, for example two proteins, by one or more bonds, for example covalent bonds.

Figure 2A:
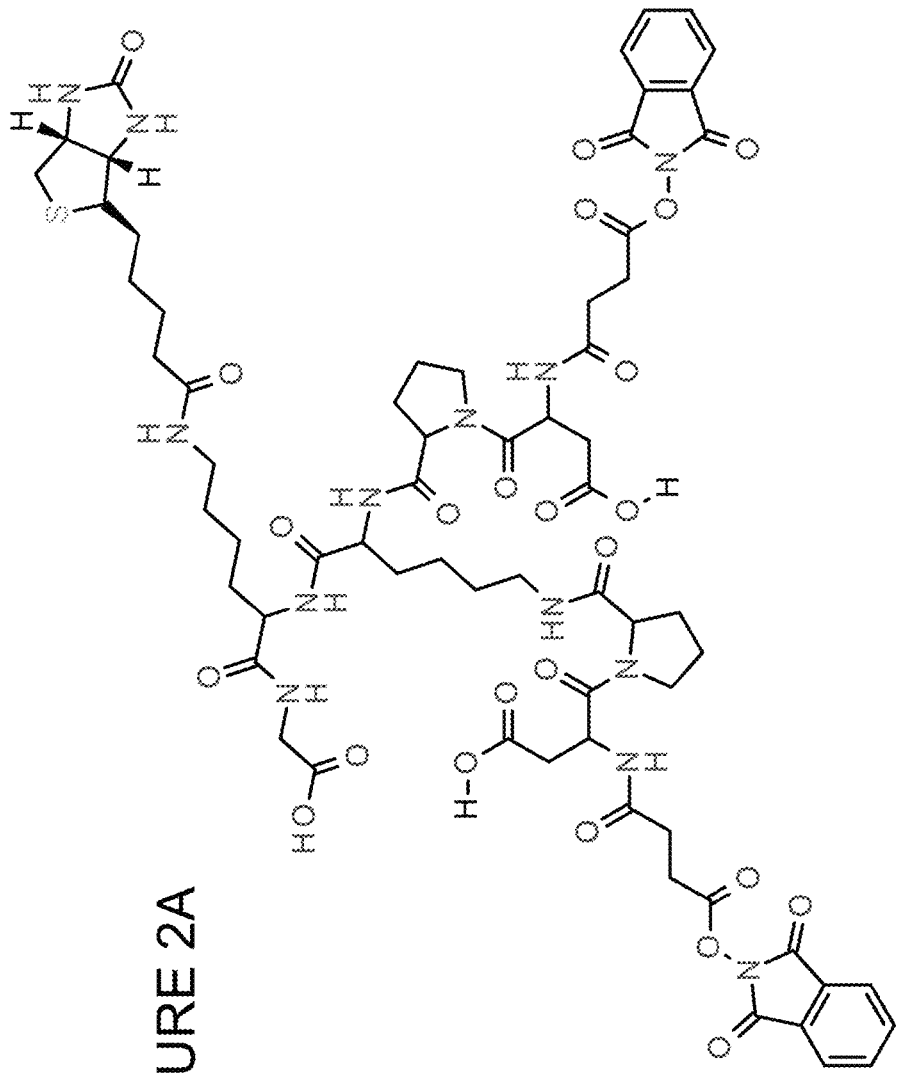
FIGS. 2A-2C. Protein interaction reporter (PIR) molecules which have been used in this study.
Figure 2B:
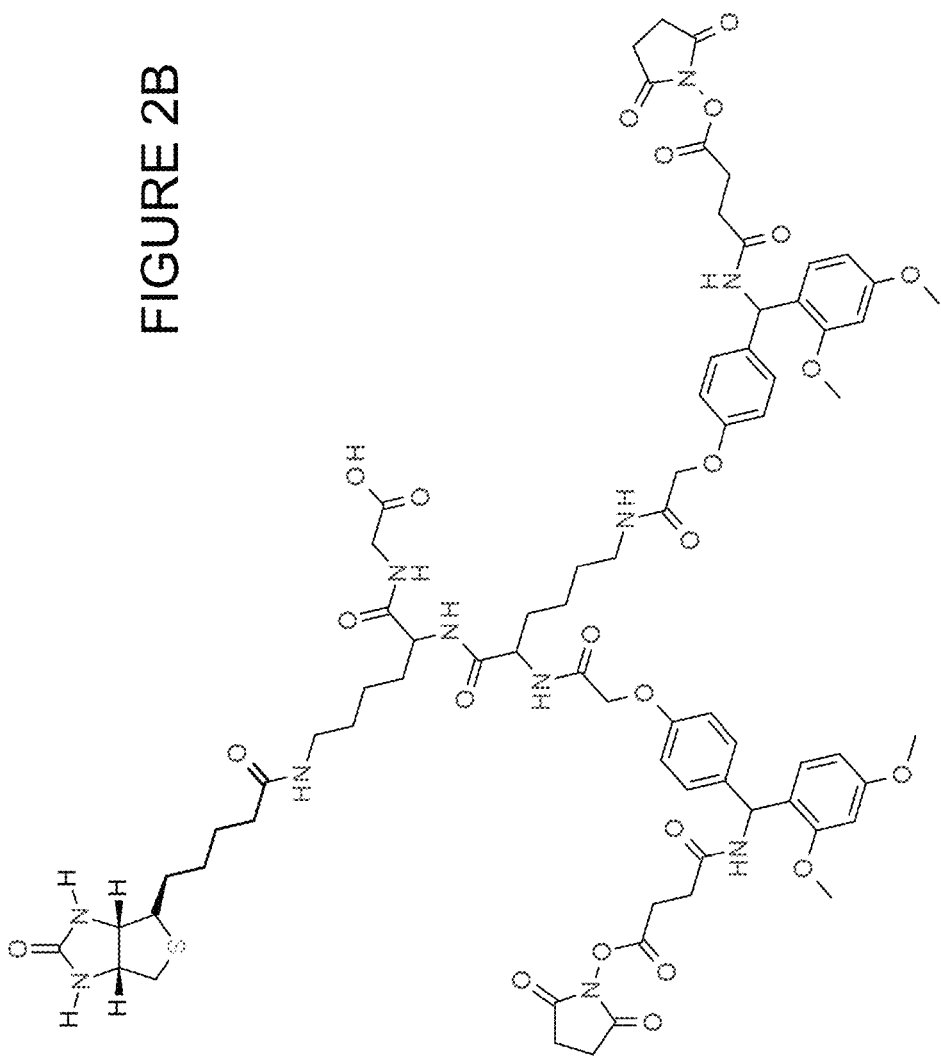
Figure 2C:
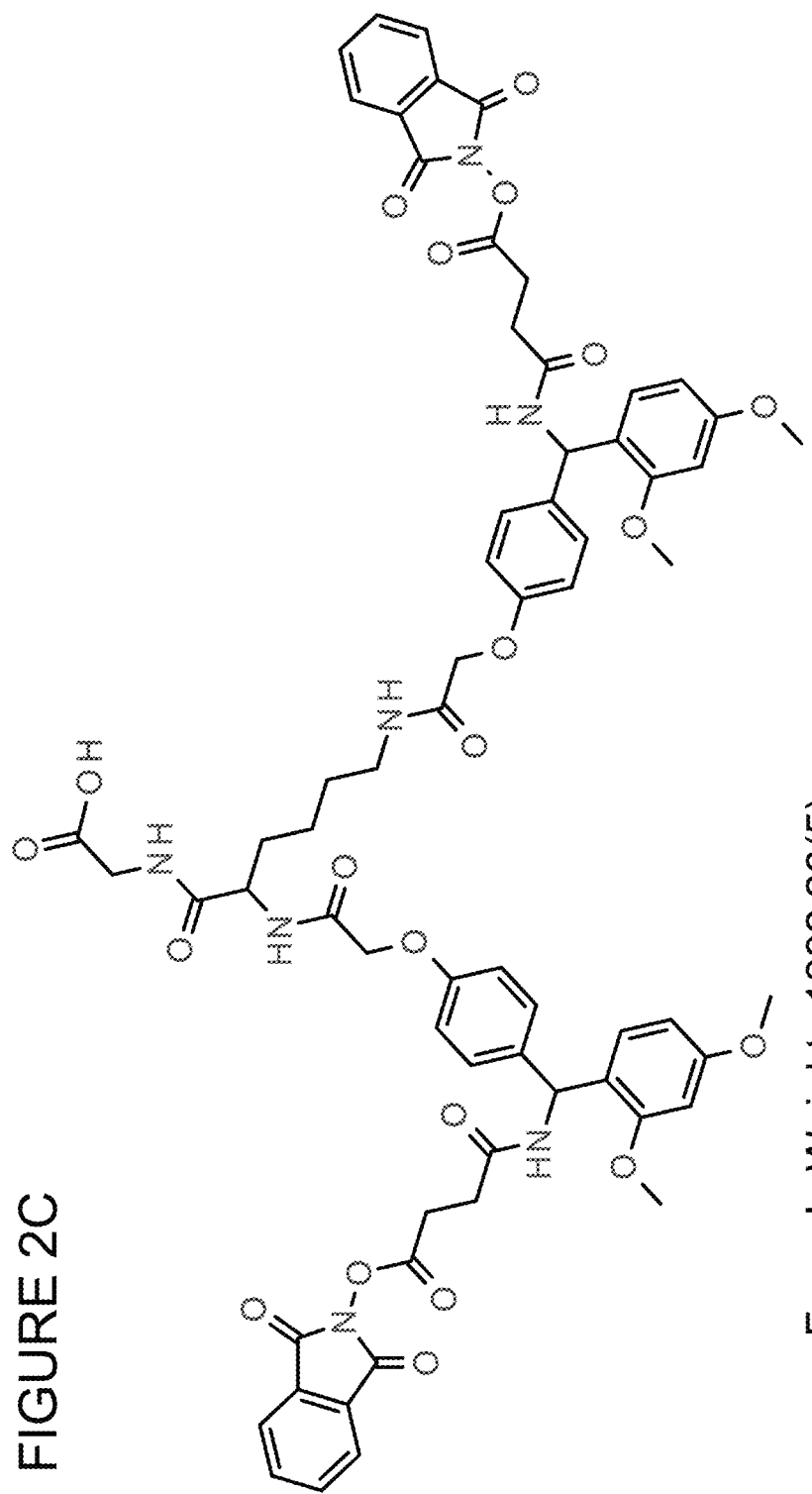

In general, chemical cross-linkers compatible with the methods disclosed herein possess a cleavage site, such as a low-energy CID cleavage site, to facilitate cross-linked peptide relationship recognition and subsequent $MS^3$ peptide fragmentation pattern acquisition. Non-limiting examples of PIR cross-linkers suitable for use with the disclosed methods are shown in FIG. 2. Although these compounds have a variety of structural and chemical properties, each contains the basic features of a mass-coded reporter ion and two low-energy CID cleavable bonds. In addition, the biotin-aspartate-proline (BDP) and BRink cross-linkers include a biotin moiety, useful for affinity purification of the conjugated reaction products. Among the benefits of using PIR cross-linkers are the engineered fragmentation patterns and the use of a reporter ion as an indicator of labeled species.

As used herein, the term "precursor" refers to a cross-linked molecule prior to the cleavage of the crosslink. Thus, in the case where a PIR cross-links two peptides, the precursor comprises the PIR cross-linker that is covalently attached to both peptides. Cleavage of the precursor yields at least one peptide and a reporter moiety.

In some embodiments of the methods disclosed herein, the population of cross-linked precursor peptides are obtained by contacting a biological system with a cleavable protein interaction reporter (PIR) cross-linker to produce cross-linked proteins, and obtaining the cross-linked precursor peptides therefrom.

In some embodiments, the methods further comprise purifying and digesting the cross-linked proteins to obtain the cross-linked precursor peptides. Purification of cross-linked peptides is used to allow those species to be detected with improved signal-to-noise ratio in the mass spectrometer. Purification is particularly beneficial with samples derived from cells, since the relative abundance of cross-linked peptides from in vivo cross-linking compared to non-cross-linked peptides is low. However, the disclosed methods can function to identify cross-linked peptides irrespective of purification, as long as the target ions are detectable in the samples. For solutions of pre-purified proteins that are cross-linked, for example, no affinity purification is needed and the disclosed methods operate to allow identification of cross-linked peptides.

In some embodiments, the biological system comprises a cell, tissue, cell lysate, blood, serum, sputum, or urine. As used herein, the term "biological system" refers to any set of molecules, cells, organisms, solutions, reagents, tissues, or other materials, which has any biological relevance. Examples of biological systems within the meaning of the disclosure include cells, cell lysates, cell cultures, tissues, organs, organisms, growth media, culture media, biological secretions, serum, blood, urine, feces, solutions or suspensions comprising proteins or peptides, etc.

In some embodiments of the disclosed methods, the conditions under which the cleavable PIR cross-linker is cleaved comprise collision-induced dissociation (CID). In mass spectrometry, "collision-induced dissociation" ("CID"), also known as "collisionally activated dissociation" ("CAD"), is a mechanism by which to fragment molecular ions in the gas phase. The molecular ions are usually accelerated by some electrical potential to high kinetic energy and then allowed to collide with neutral molecules (often helium, nitrogen or argon). In the collision some of the kinetic energy is converted into internal energy which results in bond breakage and the fragmentation of the molecular ion into smaller fragments. These fragment ions can then be analyzed by a mass spectrometer. For example, in a triple quadrupole mass spectrometer there are three quadrupoles. In one mode of operation, the first quadrupole ("Q1") can act as a mass filter and transmits a selected ion and accelerates it towards "Q2," a collision cell. The pressure in Q2 is higher and the ions collides with neutral gas in the collision cell and fragments by CID. The fragments are then accelerated out of the collision cell and enter "Q3" which scans through the mass range, analyzing the resulting fragments (as they hit a detector). This produces a mass spectrum of the CID fragments from which structural information or identity can be gained. Many other experiments using CID on a triple quadrupole exist, such as the methods disclosed herein.

In some embodiments, the population of released peptides in step (d) is analyzed using $MS^2$. In some embodiments the step (d) analysis comprises the isolation, fragmentation, and analysis of one precursor molecule at a time. In other embodiments, the step (d) analysis comprises multiplexed testing, wherein more than one precursor is isolated, fragmented and analyzed at a time. In such an embodiment, several 4+ or higher ions are isolated and fragmented simultaneously so that the disclosed methods are used to simultaneously find and identify released peptides from more than one cross-linked precursor.

In some embodiments, identifying interacting peptides in step (d) further comprises first identifying released peptides with masses lower than partial cleavage products prior to identifying released peptides that, when added to the mass of the reporter ion, have a combined mass equal to the mass of the corresponding precursor ion. In some embodiments, identifying released peptides with masses lower than partial cleavage products comprises identifying released peptides with masses that are less than the mass of the corresponding precursor ion minus the mass of the reporter ion minus the mass of lysine stumps, wherein lysine stumps are residual modifications that remain on lysine residues after cleavage.

In some embodiments, the methods disclosed herein further comprise determining the identities of the interacting peptides by subjecting the interacting peptides to conditions that cause peptide fragmentation to yield spectra that can be identified from genomic, proteomic, or other large protein sequence databases. In some embodiments, the identities of the interacting peptides are determined by $MS^3$.

In some embodiments, the $MS^3$ step takes place immediately after the $MS^2$ step. For example, in some embodiments, the identification of released peptides is accomplished during a single liquid chromatographic (LC) separation of thousands of molecules. Each species elutes from the LC column with a retention time characteristic of its overall hydrophobic character and detectable signals for each cross-linked precursor may only persist for 15 to 30 seconds. Thus, $MS^3$ proceeds before the detectable signals dissipate. In such a case, it is beneficial for $MS^3$ to proceed soon after the $MS^2$ stage (during which released peptides and precursor ions are analyzed to determine if they satisfy equation (1)) because the peptides identified in $MS^3$ are known to belong to the precursor that was analyzed by $MS^2$ moments before.

In other embodiments, $MS^3$ does not proceed immediately after $MS^2$. Rather, $MS^3$ may be performed at a later time and/or a separate location. In such a case, the ion yielding the released peptides identified in the later $MS^3$ step must be determined to be the same ion that yielded a given retention time and precursor mass in the earlier LC-$MS^2$ analysis.

In some embodiments of the methods disclosed herein, the cutoff charge state is from 0 to +10. In some embodiments, the cutoff charge state is at least +3. In some embodiments, the cutoff charge state is at least +4. In some embodiments, the cutoff charge state is at least +5.

In some embodiments, the precursor molecule comprises two cross-linked peptides. In other embodiments, the precursor molecule comprises three cross-linked peptides and the PIR cross-linker is capable of cross-linking three proteins. In other embodiments, the precursor molecule comprises four or more cross-linked peptides and the PIR cross-linker is capable of cross-linking four or more proteins.

In some embodiments of the methods disclosed herein, the cleavable PIR cross-linker comprises formula (I):

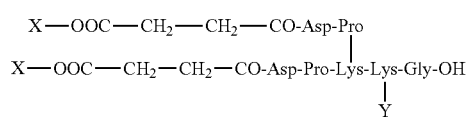

(SEQ ID NO: 27) wherein X is H, succinimid-N-yl, or phthalimid-N-yl; and Y is H or a capture moiety. In some embodiments, the capture moiety is biotin, a hemagglutinin (HA) tag, or a polyhistidine tag.

In some embodiments of the methods disclosed herein, the cleavage condition is collision-induced dissociation (CID).

As used herein, the term "capture moiety" refers to a chemical moiety attached to a molecule that can be used to capture the molecule, for example, through interaction with another chemical moiety, for purposes such as affinity purification. For example, a biotin capture moiety can be used in conjunction with a streptavidin column to affinity purify the molecule comprising the biotin moiety. A poly-histidine tag (His-tag, 6×His-tag, hexa histidine-tag, or His6-tag) is a capture moiety comprising at least six histidine amino acid residues that can be used to capture a His-tagged molecule because the string of histidine residues binds to several types of immobilized metal ions, including nickel, cobalt and copper, under specific buffer conditions. In addition, anti-His-tag antibodies are commercially available for use in methods involving His-tagged proteins. Any protein for which an antibody specific for that protein exists can comprise a capture moiety. Other examples of capture moieties include hemagglutinin (HA) tag, streptavidin-binding peptide, calmodulin-binding peptide, S-peptide, and chitin-binding domain.

In another aspect, the disclosure provides methods of identifying a candidate compound for treating cancer comprising: (a) contacting a peptide pair from the group consisting of:

(i)
              (SEQ ID NO: 1)
FYEQFSKNIK, (SEQ ID NO: 1)
FYEQFSKNIK;

(ii)
              (SEQ ID NO: 2)
FYEAFSKNLK, (SEQ ID NO: 2)
FYEAFSKNLK;

(iii)
              (SEQ ID NO: 1)
FYEQFSKNIK, (SEQ ID NO: 2)
FYEAFSKNLK;

(iv)
              (SEQ ID NO: 1)
FYEQFSKNIK, (SEQ ID NO: 3)
KHLEINPDHPIVETLR;

(v)
              (SEQ ID NO: 4)
APFDLFENKK, (SEQ ID NO: 1)
FYEQFSKNIK;

-continued (vi)
FYEQFSKNIK, (SEQ ID NO: 1)

KAAALEAMK; (SEQ ID NO: 5)
and (vii)
FYEAFSKNLK, (SEQ ID NO: 2)

KAAALEAMK; (SEQ ID NO: 5)

with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating cancer.

In another aspect, the disclosure provides methods of identifying a candidate compound for treating cancer comprising: (a) contacting a protein pair or fragments thereof from the group consisting of:
(i) HS90A (GenBank: CAI64495.1; SEQ ID NO: 20), HS90A (GenBank: CAI64495.1; SEQ ID NO: 20);
(ii) HS90B (GenBank: AAH68474.1; SEQ ID NO: 21), HS90B (GenBank: AAH68474.1; SEQ ID NO: 21);
(iii) HS90A (GenBank: CAI64495.1; SEQ ID NO: 20), HS90B (GenBank: AAH68474.1; SEQ ID NO: 21);
(iv) HS90A (GenBank: CAI64495.1; SEQ ID NO: 20), STIP1 (GenBank: AAH39299.1; SEQ ID NO: 22);
(v) HS90B (GenBank: AAH68474.1; SEQ ID NO: 21), STIP1 (GenBank: AAH39299.1; SEQ ID NO: 22);
with a plurality of test compounds under conditions suitable for binding of one member of the protein pair or a fragment thereof to the other member of the protein pair or a fragment thereof; and (b) identifying a test compound that reduces binding of one member of the protein pair or a fragment thereof to the other member of the protein pair or a fragment thereof relative to a control, wherein the identified test compound is a candidate compound for treating cancer, and wherein pairs (i) and (ii) represent the interaction of a protein with itself.

In another aspect, the disclosure provides methods of identifying a candidate compound for treating an antibiotic-resistant infection comprising: (a) contacting a peptide pair comprising KINLYGNALSR (SEQ ID NO: 6) and NDIAPYLGFGFAPKINK (SEQ ID NO: 7) with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating an antibiotic-resistant infection.

In another aspect, the disclosure provides methods of identifying a candidate compound for treating an antibiotic-resistant infection comprising: (a) contacting a protein pair or fragments thereof comprising Oxa-23 (GenBank: ACJ39972.1; SEQ ID NO: 23) and CarO (GenBank: ACN32317.1; SEQ ID NO: 24) with a plurality of test compounds under conditions suitable for binding of one member of the protein pair or a fragment thereof to the other member of the protein pair or a fragment thereof; and (b) identifying a test compound that reduces binding of one member of the protein pair or a fragment thereof to the other member of the protein pair or a fragment thereof relative to a control, wherein the identified test compound is a candidate compound for treating an antibiotic-resistant infection.

In another aspect, the disclosure provides methods of identifying a candidate compound for treating *A. baumannii* infection comprising: (a) contacting a peptide pair from the group consisting of:

(i)
VFFDTNKSNIKDQYKPEIAK, (SEQ ID NO: 8)

MSAAEAVKEK; (SEQ ID NO: 9)

(ii)
TKEGR, (SEQ ID NO: 10)

MSAAEAVKEK; (SEQ ID NO: 9)
and (iii)
LSTQGFAWDQPIADNKTK, (SEQ ID NO: 11)

MSAAEAVKEK; (SEQ ID NO: 9)

with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating *A. baumannii* infection.

In another aspect, the disclosure provides methods of identifying a candidate compound for treating *A. baumannii* infection comprising: (a) contacting a protein pair or fragments thereof comprising OmpA (GenBank: AAR83911.1; SEQ ID NO: 25) and desmoplakin (GenBank: AAA85135.1; SEQ ID NO: 26) with a plurality of test compounds under conditions suitable for binding of one member of the protein pair or a fragment thereof to the other member of the protein pair or a fragment thereof; and (b) identifying a test compound that reduces binding of one member of the protein pair or a fragment thereof to the other member of the protein pair or a fragment thereof relative to a control, wherein the identified test compound is a candidate compound for treating *A. baumannii* infection.

In another aspect, the disclosure provides cleavable protein interaction reporter (PIR) cross-linkers comprising formula (I):

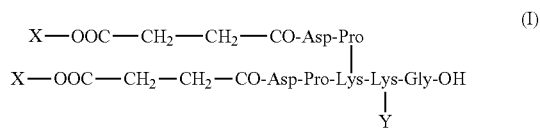

(SEQ ID NO: 27) wherein X is H, succinimid-N-yl, or phthalimid-N-yl; and Y is H or a capture moiety. In some embodiments, the amino acids are L-amino acids. In some embodiments, the capture moiety is biotin, a His tag, or an HA tag.

The methods and compositions disclosed herein relate to cross-linking mass spectrometry (XL-MS). These methods involve "fixing" the biological system through covalent chemical modification of amino acid residues and investigating the cross-linked sites using mass spectrometry methods. XL-MS enables the identification of PPIs as well as unique topological features and yields large-scale data. An advantage of cross-linking is the potential to study protein topologies that cannot be readily investigated using other techniques, such as disordered protein domains and membrane proteins. Unlike X-ray crystallography or NMR structure determination, cross-linking data can provide unique structural insight on many proteins as they exist in their natural cellular environment in a single experiment. XL-MS thus has the capacity to produce large-scale data sets, although in the past, technical limitations have constrained the scope of XL-MS methods to the identification of less than 100 cross-linked peptides in vivo.

As large-scale cross-linking data becomes available, new software tools for data processing and visualization are required to replace manual data analysis. The XLink-DB system, or XLink-DB for short, can include a software package that serves as a data storage site and visualization tool for cross-linking results. XLink-DB accepts data generated with any cross-linker and stores them in a relational database. Cross-linked sites are automatically mapped onto PDB structures if available, and results are compared to existing protein interaction databases. A protein interaction network is also automatically generated for the entire data set. A server with the XLink-DB system, including examples, and a help page are available for noncommercial use (see brucelab.gs.washington.edu/cross-linkdbvl/). The source code can be viewed and downloaded; e.g., see sourceforge.net/projects/cross-linkdb/?source=directory.

Protein interactions support most biological functions and are directed by the shapes or topologies of the interacting proteins. Improved measurements of protein interaction topologies in cells are needed to increase our understanding of how protein interactions carry out their life supporting functions. Chemical cross-linking with mass spectrometry has been used to study protein structures and complex topologies for several years Most prior applications have been limited to either purified proteins or complexes due to the complexity and wide dynamic range presented by complex biological samples. Recent technical advancements of the chemical cross-linking methods achieved in a number of laboratories have allowed this technique to be extended to complex systems. Successful applications of chemical cross-linking to studies of intact virus particles, cell lysates, and even intact bacterial and human cells suggest that in the future, cross-linking methods may provide a majority of structural and topological data on protein complexes as they exist in cells or other complex samples.

As is the case with most large-scale biological data, its usage among investigators in biochemistry, biophysics, cellular and molecular biology, as well as proteomics requires that new tools be developed to visualize, share and compare these results. This is especially true for large-scale cross-linking data since current growth in data quantity exceeds manual data analysis capabilities. Furthermore cross-linking with mass spectrometry data sets are unique in that they contain multiple tiers of information on protein sequence, interaction, and structural levels for which no single existing data analysis tool can sufficiently support. Often data analysis requires comparison of cross-linking results with existing crystal structure data if available. In addition, cross-linking data are often compared with existing protein interaction data. If previously unknown interactions are discovered, the cross-linked site information can be superimposed by computational docking of interacting structures. These steps can require hours of efforts even with only a few cross-linked peptide pairs in a single experiment and this approach becomes intractable for hundreds of cross-linked peptides.

XLink-DB includes software designed to serve both as a storage site and an online data processing and visualization tool to enable analysis of large-scale cross-linked peptide data sets. Importantly, XLink-DB is useful among biological and proteomics research communities since it provides new analysis capabilities and improved access to complex cross-linking topological data.

Figure 21A:
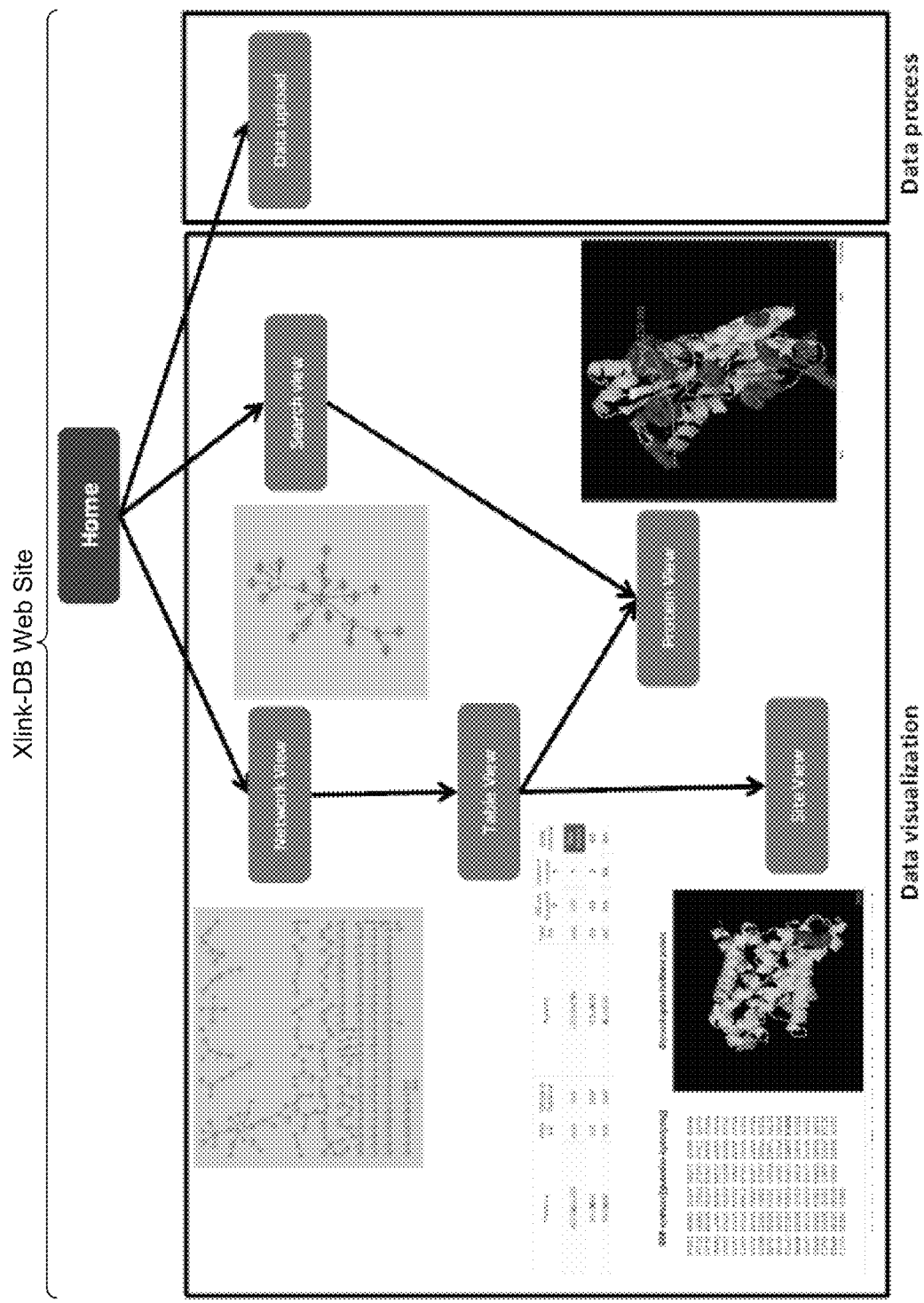
FIG. 21A depicts a web structure for the XLink-DB system, in accordance with an example embodiment. XLink-DB allows loading, visualization and analysis of protein-protein interaction data acquired with chemical cross-linking and mass spectrometry. Cross-linked peptides are mapped against protein structured downloaded from PDB so that cross-linked sites can be automatically visualized on protein structures. A Cytoscape interaction network is created with XLink-DB so that all identified protein-protein interactions can be visualized. This network is mapped against existing protein-protein interaction databases acquired with yeast two hybrid, co-IP other technologies.

XLink-DB allows users to upload their cross-linking data and populate a relational database, as well as browse existing data sets. As indicated in FIG. 21B, XLink-DB can use a data process algorithm for uploaded data that automatically retrieves related protein sequence information from the UniProt catalog and high resolution structure information from the Protein Data Bank (PDB). If relevant structures are available, cross-linked site annotation can be automatically performed with XLink-DB and visualized within the Jmol applet (see jmol.sourceforge.net). The cross-linking data is also visualized in a protein interaction network view with an embedded web-based Cytoscape tool. The data stored in XLink-DB can be compared to existing protein interaction databases such as IntAct and EciD. We anticipate that XLink-DB can be a useful tool and benefit the proteomics research community as well as all researchers interested in protein topologies and interactions.

Several protein interaction databases have been established and embraced by the scientific community, such as PDB, EciD and IntAct. But none of them provide protein interaction topological data that can be provided by XLink-DB. XLink-DB was developed to maximize the access and utility of protein interaction topological data that is now available and can come from these technological advancements.

XLink-DB presents a new way to organize and demonstrate protein interaction data with topological information. Conventional databases either lack the interaction information or lack the topological information for the protein complexes. With the advancement of new cross-linking technologies, large scale protein interaction studies are now becoming reality. XLink-DB is the first database to allow compilation and analysis of large-scale cross-linking data. XLink-DB can help the cross-linking community to store, share and process their data, as well as enable sharing the data with other scientists with interests in protein interactions and topologies.

The XLink-DB System

The XLink-DB system can be embodied using a computing device operating a web site. An as example of the XLink-DB system, an example XLink-DB web site can utilize PHP 5.5 and JavaScript, example XLink-DB data analysis tools can be programmed with Java 1.6, and example XLink-DB data can be stored in a relational database, such as a MySQL database. Other embodiments can utilize other software techniques and/or programming languages for the XLink-DB web site. In some embodiments, functionality of the XLink-DB web site can depend on both Java applets and flash plug-in. As shown in FIG. 21A, the XLink-DB web site contains two major modules: (1) data upload, process and storage and (2) data visualization.

Five different views (interaction network, protein structure, search, site and table views) are available for cross-linked peptide data analysis. Interaction network view shows the protein interaction network generated from the data set. Protein structure view shows the cross-linking peptide pairs on the existing PDB structure. A key feature of XLink-DB is the ability to map cross-linked sites on protein complexes for which individual protein crystal structures exist, but no cocrystals have been reported. Site view is designed to display the sites when the co crystal structure does not exist. Search view is a subnetwork of the data set. The table view is a summary of the data set in a table. To help users get familiar with the features of the database, we have created a video tutorial which can be found in the help page. In addition, we have also put tooltips on some parameters to guide the users. Details on each module are discussed below.

Data Upload, Process, and Storage

The users can choose if they want their data to be publically available. If they choose not to release their data to the public, they can get a table name after the data upload is finished and their data cannot appear in the drop-down list to choose. Instead, the users can use the table name to access their nonpublic data. Their data can be stored in the database for 90 days. If the user chooses to make their data public available, the data can be permanently stored in the database and can appear in a dropdown list in the selection box under "Choose a data set". The users can access their published and previously uploaded data from the drop-down list. Data are uploaded in XLink-DB in a tab-delimited file format with column arrangements as indicated on XLink-DB help page (see brucelab.gs.washington.edu/cross-linkdbvl/help-.php).

FIG. 21B illustrates an example data process algorithm. In this data process algorithm, XLink-DB can parse the input file to extract the UniProt identifiers for each cross-linked protein contained within the data set. The UniProt files containing protein annotation is then automatically downloaded from the UniProt database. The sequence information and identifiers for each labeled protein are parsed from the UniProt file and stored within the database in XLink-DB. If available, the PDB code associated with each protein is also retrieved from the UniProt annotation.

Figure 21C:
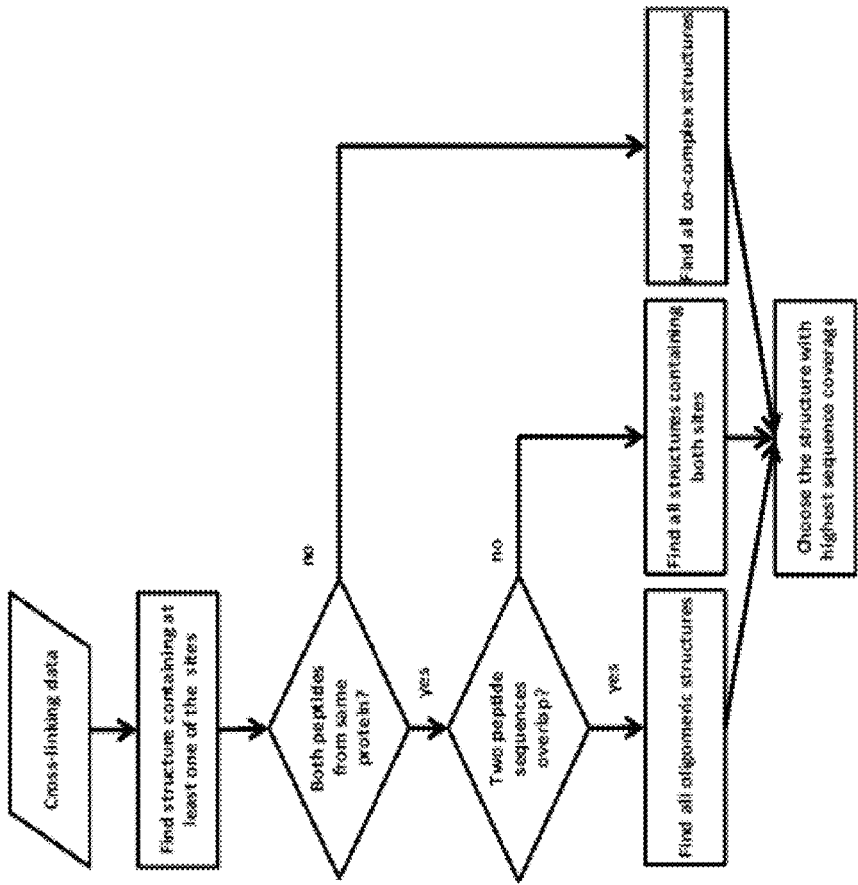
FIG. 21C is a flowchart for an algorithm for choosing PDB structures by the XLink-DB system, in accordance with an example embodiment.
Figure 21B:
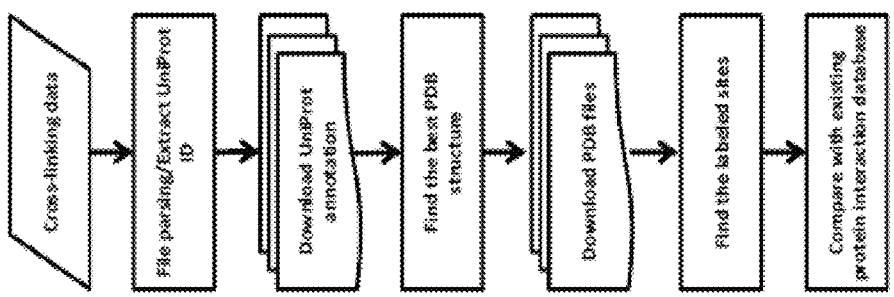
FIG. 21B is a flowchart for a data process algorithm for the XLink-DB system, in accordance with an example embodiment.

FIG. 21C illustrates an example algorithm for selecting structures related to cross-linked proteins for visualization. For cases where more than one PDB code is associated with one protein, XLink-DB can select and retrieve the PDB structure on the basis of the following rules: First XLink-DB can find all the PDB files that contain structural information covering the cross-linked site. If two cross-linked peptides originate from different protein sequences, which identifies a hetero interaction, all the cocrystal structures containing the two labeled proteins can be put in the candidate pool for later selection. Next, if the cross-linked peptide pair contains identical or overlapping peptide sequences that originate within a single protein sequence, all oligomer structure files containing both sites can be put in the candidate pool. If the cross-linked peptide pair does not fall into either of the two categories above, individual structure files containing both sites can be put into the candidate pool.

FIG. 21C indicates that the algorithm can involve choosing the structure with highest sequence coverage from the candidate pool to use for visualization of the cross-linked peptide pair. The structure with highest sequence coverage can be chosen to allow a best-possible representation of the entire protein and greatest-possible chance to cover cross-linked sites. If no structural file can be found that contains both labeled sites, the algorithm can choose the best individual structures for each labeled site.

Returning to FIG. 21B, after the PDB codes are assigned to each protein, the PDB files for these proteins are automatically downloaded. XLink-DB can computes atom numbers for all cross-linked peptide sites by at least:

The peptide sequence can be mapped to the protein sequence in the PDB file.

The atom numbers and coordinates of every copy of the cross-linked peptide in the PDB file can be identified. The chosen atoms can include the a carbon of the cross-linked lysine residues.

The shortest distance between the two cross-linked sites contained in each cross-linked peptide pair can be calculated from the atomic coordinates of the a carbon atoms.

The associated atom numbers of the cross-linked sites are stored within the database embedded in XLink-DB.

The final data processing procedure shown in FIG. 21B is to compare the uploaded data with an existing protein interaction databases, such as the IntAct and EciD databases. These databases were utilized on the basis of the coverage of protein interaction data; e.g., IntAct is used for human data, EciD is used for $E.$ $coli.$ In some cases, a node distance can be determined between two cross-linked proteins. The node distance between two cross-linked proteins can serve as a measurement from the reference protein interaction network composed from existing protein interaction database information.

The node distance can provide a numerical value for direct and indirect interactions. For example, if two cross-linked proteins, A and B, are known to interact, the node distance within the reference protein interaction network can be determined to be 0; i.e. a node distance of 0 indicates a direct interaction between the cross-linked proteins A and B.

Otherwise the node distance can be determined to be the smallest number of nodes or proteins that exist in the reference network linking the two cross-linked proteins. For example, suppose the two cross-linked proteins A and B have an interaction involving N=2 interactors (nodes or proteins); e.g., A and B would be linked by additional proteins C and D. The node distance for the interaction can be set to N to indicate an indirect interaction between the cross-linked proteins involving N interactors. In this example, the node distance between A and B linked via interactors C and D would be 2. Many other examples of direct interactions, indirect interactions, and corresponding node distances are possible as well.

If the cross-linked proteins cannot be connected in the reference network, a not-applicable value; e.g., "N/A" can be returned for this computed distance.

Data Visualization

Protein data visualization can be provided using a number of views; e.g., a Network View, a Protein View, a Table View, a Site View, a Search View, and perhaps other views, as shown in FIG. 21A. In Network View, a protein interaction network of the cross-linked peptide data set can be generated with a Cytoscape plugin and be displayed on the left side of the page. A complete set of features available in the Cytoscape plugin are described by Lopez.

Each node in the Network View represents a protein, and each edge represents all the cross-linked peptide pairs linking the two proteins. The users can open files, save files and change the layout and style options using a menu. A toolbox at a right bottom corner of the network graph enables panning and zooming in the graph. Every node and edge in the graph can be selected, dragged and edited.

The page can include three tabs: Visual Style, Filter and Properties. The Visual Style tab allows users to change the color of the nodes, edges and background. The Filter tab allows users to filter the nodes based on the value of attributes. The Properties tab is automatically activated when nodes or edges are selected. When one or more nodes are selected, the interacting partners of the selected nodes can be listed in a table. The name of each interacting partner is converted into a button, which can lead to the Protein View of this protein complex. When one or more edges are selected, the interactions that are represented by the selected edges can be listed in a table. Each interaction is converted to a button, which can lead to the Protein View of the pair.

In addition, the protein interaction network developed with cross-linking data can be compared with previous known protein structural and interaction information. For instance, the size of the node can indicate whether a crystal structure for the protein exists in PDB. The thickness of the edges can be related to the number of cross-linked peptide pairs that have been identified in the data set. For example, thicker lines can be indicative of two or more cross-links. The color of the edge can indicate the distance of connection of the two proteins in reference protein interaction database. As an example, red edges can indicate that direct interactions between linked proteins are found in IntAct or EciD. Also, green edges can indicate that linked proteins have been found to share a common interactor in the reference database and are therefore one node away. As another example, black edges can indicate that linked proteins are more than one node away or were not found in the reference databases. It should be noted that for linkages that contain two peptides from the same protein, the edge color can appear red unless one or more cross-linked pairs are comprised of two peptides with overlapping sequences indicating unambiguous linkage of a homodimer. In these unambiguous homodimer cases, proteins previously known to form homomultimers can appear with red edges, while those not yet known to form homomultimers can appear with green edges. Other visualization schemes, including other coloring schemes, are possible as well.

A Protein View page can contain a Jmol applet on the top if the structure is available, and a result table on the bottom. The user can change basic display options; e.g., using a right-click menu in a Jmol layer.

Part of the page can contain a result table with all the pairs associated with the two proteins. This table can contain data such as peptide sequence, gene name, PDB code, and a number of cross-linked pairs that involve the peptide. The number of cross-linking pairs involving the peptide can measure reactivity and spatial proximity of the labeled site. A larger number of cross-linking pairs can indicate that the labeled site is close to many other sites and thus the labeled site is highly reactive. The users can also use their own favorite structure if they do not appreciate the preassigned structures by inputting the PDB code and the chain IDs for the respective proteins of the own favorite structure.

Buttons on the Protein View page can be used change the display of cross-linked peptide pairs. A "display all" button can illustrate all cross-linked sites associated with the two proteins displayed in the Jmol layer. A "reset complex" button can remove all the cross-linking pairs labeled on the structure. A "display single pair" button can display the selected pair on the structure. A "generate table view" button can change the display to the Table View. Other controls, such as buttons, can be used to change the display as well.

The Table View page can include a result table page. The result table page can contain a top part and a bottom part. The top part can show a title and a link to the network view. The bottom part can show a result table with a peptide sequence, protein accession, PDB code, distance of connection and links to the Protein View. The result table can be sorted by entries within each column by clicking on respective column headings. Each entry in Peptide NB columns can be hyperlinked to the Site View page discussed immediately below. Protein names shown in Protein A/B column within the table can be hyperlinked to relevant UniProt pages for each protein to facilitate further investigation. Similarly, PDB code for peptide NB names can be hyperlinked to the relevant PDB page for additional structure information as needed. A show structure button can produce a protein-level view of the cross-linked pair.

The Site View can show two or more labeled sites in parallel windows to enable visualization of the location of the labeled peptide in the protein. When the crystal structure is available for either protein but not the complex, the site can be highlighted using a predetermined color, such as magenta, on the structure. Otherwise, the entire cross-linked peptide can be highlighted using another predetermined color, such as red, in the protein sequence.

The Search View can be accessed from the home page. The user can search for a protein of interest using a UniProt ID, UniProt accession, or gene name. The user can search for one protein or search for a list of protein IDs. The search can be performed against all the data sets for the selected organism.

Example XLink-DB Results

Two data sets were used to demonstrate the features of XLink-DB. One data set, "Weisbrod et al.", is a large scale cross-linking experiment performed in our laboratory on intact $E.\ coli$ cells (see companion manuscript by Weisbrod et al.). The other "Yang et al." data set was extracted from a recent publication by Yang et al., in which the researchers performed cross-linking on $E.\ coli$ cell lysate. Both data sets comprise large reported cross-linking data sets and contain several hundred unique cross-linked sites.

There are a few differences in the two experiments. Weisbrod et al. used a customized cross-linker, which is mass spectrometry cleavable and has biotin affinity tag for purification. Yang et al. used commercially available DSS, which is noncleavable. Both data sets used strong cation exchange to enrich high charge peptides. Weisbrod et al. performed avidin capture to enrich biotin-tagged peptides prior to mass spectrometry analysis.

Figure 22:
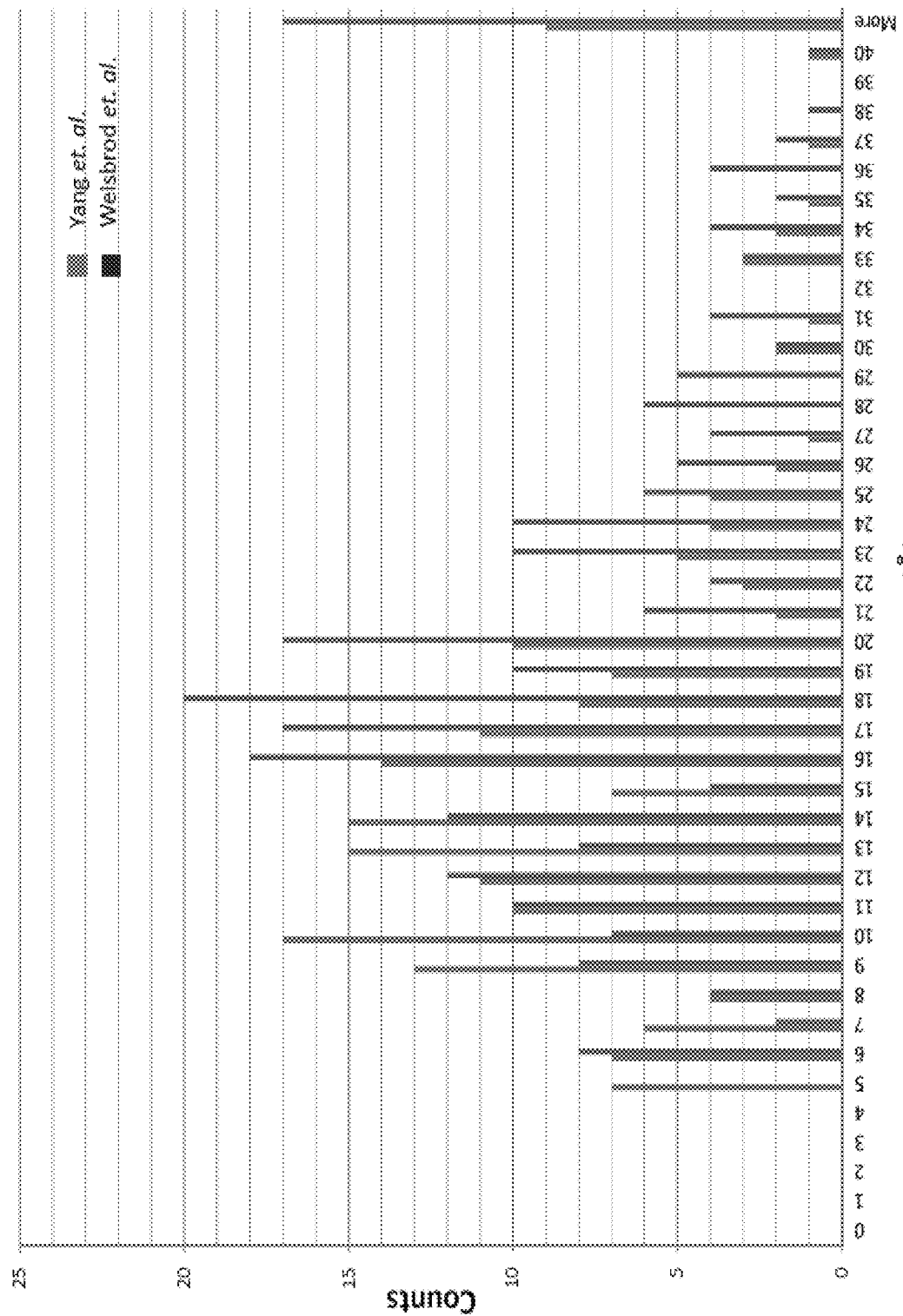
FIG. 22 depicts a distribution of interlinked distances of large-scale cross-linked peptide data sets from cells and cell lysates, in accordance with an example embodiment.

Using XLink-DB to analyze these data sets can provide unique insight into data sets that would have been difficult and time-consuming to get manually. FIG. 22 illustrates a distribution of cross-linked distances extracted from XLink-DB and plotted in Excel. Both data sets show broad distributions of observed cross-linked distances. Disuccinimidyl suberate (DSS) a cross-linker with a relatively short spacer arm length (11.4 A) was applied in the Yang et al. data set. The cross-linker used in the Weisbrod et al. data set has a spacer arm longer than 30 A. However, the fact that both data sets show similar cross-linked distance distributions suggests that cross-linker size is less important than protein flexibility in determination of which protein sites are cross-linked in complex mixtures.

Using XLink-DB, both data sets were compared to the $E.\ coli$ protein interaction database EciD, while only considering interactions from experimentally derived data. FIG. 23 shows the distribution of the node distances of both data sets and a Monte Carlo simulation of the expected distance for randomly selecting two proteins. Both cross-linking data sets consist of approximately 130 inter-protein interactions. For the Monte Carlo simulation, 130 randomly selected protein pairs were chosen to represent the sample size of the cross-linking experiment. The experiment was repeated 100 times, and the average percentage of each distance is plotted in FIG. 23. On the basis of the Monte Carlo simulation, the most probable expected distance of two randomly chosen proteins is 2 nodes. The majority of the distances for the two cross-linking data sets is below or equal to one node, suggesting that both the Weisbrod et al. and Yang et al. data sets for cross-linking experiments show good correlation with other experimental techniques. Furthermore, the Weisbrod et al. data set contains the highest percentage (25%) of known direct interactors (0 nodes), whereas random simulation predicts about 4%. This suggests that data from either the Weisbrod et al. or Yang et al. cross-linking experiments is significantly different from random data based on existing known interactions from EciD.

Example

Computing Network

Figure 24A:
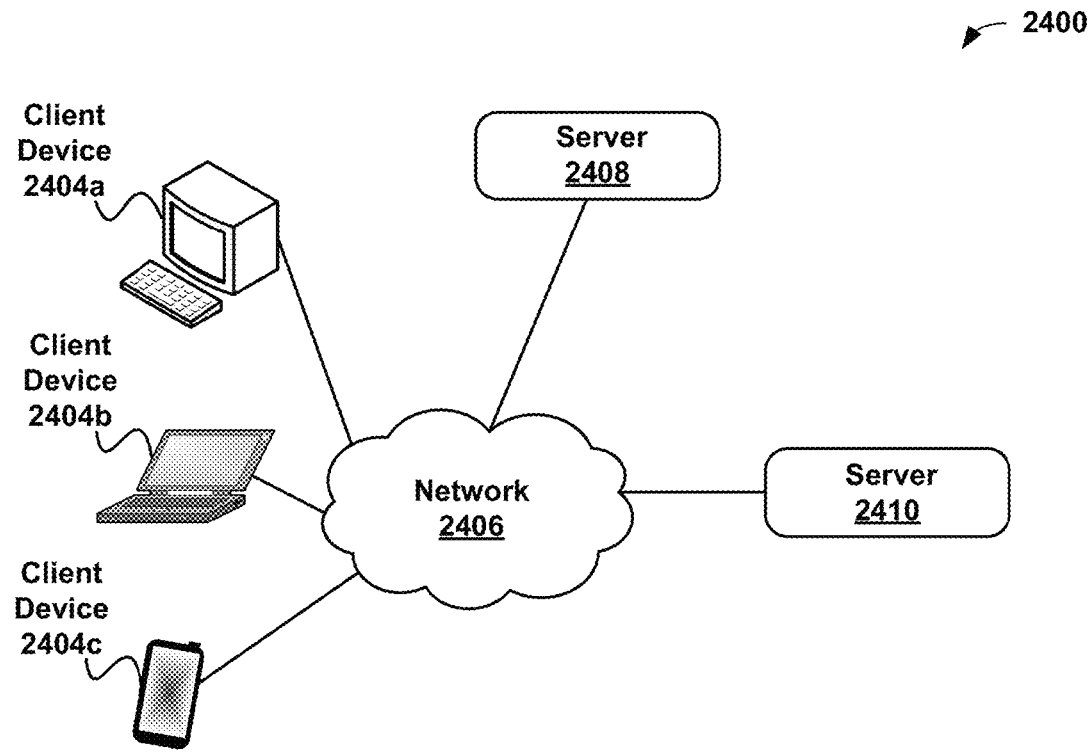
FIG. 24A is a block diagram of an example computing network, in accordance with an embodiment.

FIG. 24A is a block diagram of example computing network 2400 in accordance with an example embodiment. In FIG. 24A, servers 2408 and 2410 are configured to communicate, via a network 2406, with client devices 2404a, 2404b, and 2404c. As shown in FIG. 24A, client devices can include a personal computer 2404a, a laptop computer 2404b, and a smart-phone 2404c. More generally, client devices 2404a-2404c (or any additional client devices) can be any sort of computing device, such as a workstation, network terminal, desktop computer, laptop computer, wireless communication device (e.g., a cell phone or smart phone), and so on.

The network 2406 can correspond to a local area network, a wide area network, a corporate intranet, the public Internet, combinations thereof, or any other type of network(s) configured to provide communication between networked computing devices. In some embodiments, part or all of the communication between networked computing devices can be secured.

Servers 2408 and 2410 can share content and/or provide content to client devices 2404a-2404c. As shown in FIG. 24A, servers 2408 and 2410 are not physically at the same location. Alternatively, servers 2408 and 2410 can be co-located, and/or can be accessible via a network separate from network 2406. Although FIG. 24A shows three client devices and two servers, network 2406 can service more or fewer than three client devices and/or more or fewer than two servers.

Example Computing Device

Figure 24B:
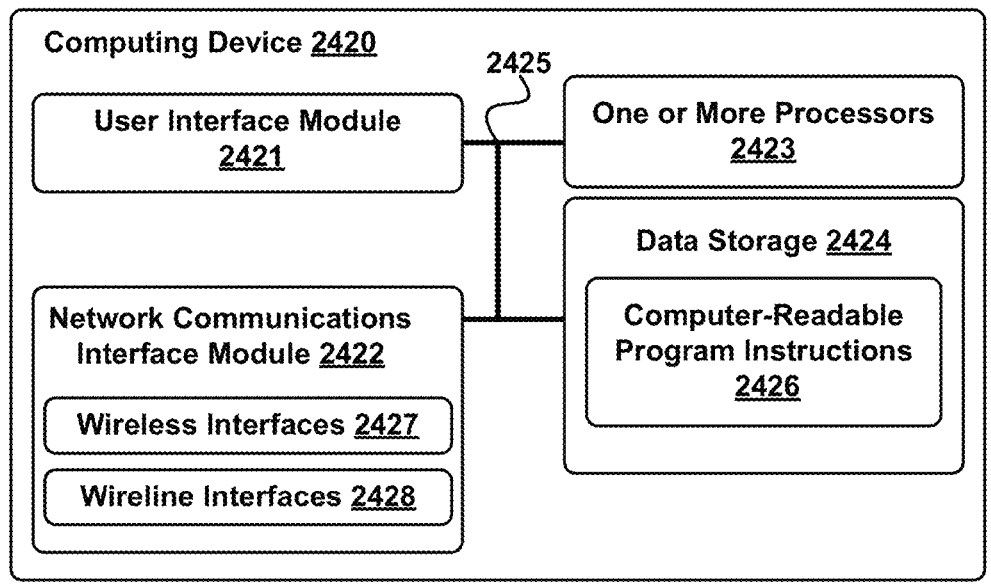
FIG. 24B is a block diagram of an example computing device, in accordance with an embodiment.

FIG. 24B is a block diagram of an example computing device 2420 including user interface module 2421, network-communication interface module 2422, one or more processors 2423, and data storage 2424, in accordance with embodiments of the invention.

In particular, computing device 2420 shown in FIG. 24B can be configured to perform one or more functions of the herein-described XLink-DB system, client devices 2404a-2404c, network 2406, and/or servers 2408, 2410. Computing device 2420 may include a user interface module 2421, a network-communication interface module 2422, one or more processors 2423, and data storage 2424, all of which may be linked together via a system bus, network, or other connection mechanism 2425.

Figure 25:
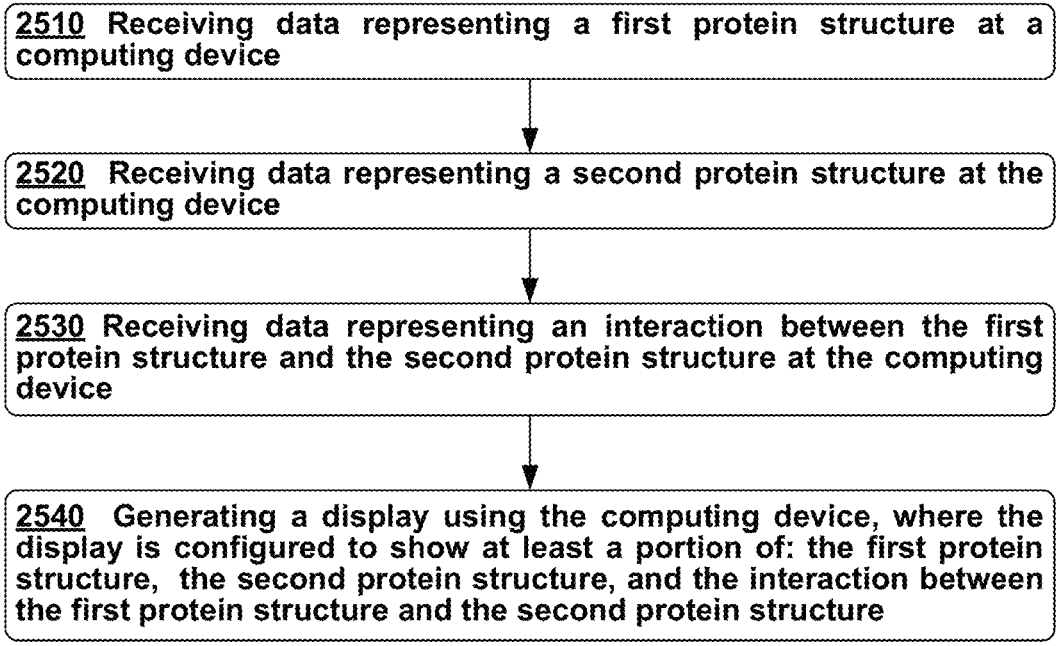
FIG. 25 is a flowchart for an example method for generating a display of multiple protein structures, in accordance with an example embodiment.

Computing device 2420 can be a desktop computer, laptop or notebook computer, personal data assistant (PDA), mobile phone, embedded processor, touch-enabled device, or any similar device that is equipped with at least one processing unit capable of executing machine-language instructions that implement and/or perform at least part of the herein-described techniques, algorithms, and methods, including but not limited to the data process algorithm discussed above at least in the context of FIG. 21B, the algorithm for selecting structures discussed above at least in the context of FIG. 21C, one or more functions of the herein-described XLink-DB system, and the method 2500 discussed below in the context of at least FIG. 25.

User interface 2421 can receive input and/or provide output, perhaps to a user. User interface 2421 can be configured to send and/or receive data to and/or from user input from input device(s), such as a keyboard, a keypad, a touch screen, a computer mouse, a track ball, a joystick, and/or other similar devices configured to receive input from a user of the computing device 2420. User interface 2421 can be configured to provide output to output display devices, such as one or more cathode ray tubes (CRTs), liquid crystal displays (LCDs), light emitting diodes (LEDs), displays using digital light processing (DLP) technology, printers, light bulbs, and/or other similar devices capable of displaying graphical, textual, and/or numerical information to a user of computing device 2420. User interface module 2421 can also be configured to generate audible output(s), such as a speaker, speaker jack, audio output port, audio output device, earphones, and/or other similar devices configured to convey sound and/or audible information to a user of computing device 2420.

Network-communication interface module 2422 can be configured to send and receive data over wireless interface 2427 and/or wired interface 2428 via a network, such as network 2406. Wireless interface 2427 if present, can utilize an air interface, such as a Bluetooth®, Wi-Fi®, ZigBee®, and/or WiMAX™ interface to a data network, such as a wide area network (WAN), a local area network (LAN), one or more public data networks (e.g., the Internet), one or more private data networks, or any combination of public and private data networks. Wired interface(s) 2428, if present, can comprise a wire, cable, fiber-optic link and/or similar physical connection(s) to a data network, such as a WAN, LAN, one or more public data networks, one or more private data networks, or any combination of such networks.

In some embodiments, network-communication interface module 2422 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well as or in addition to those listed herein to secure (and then decrypt/decode) communications.

Processor(s) 2423 can include one or more central processing units, computer processors, mobile processors, digital signal processors (DSPs), microprocessors, computer chips, and/or other processing units configured to execute machine-language instructions and process data. Processor(s) 2423 can be configured to execute computer-readable program instructions 2426 that are contained in data storage 2424 and/or other instructions as described herein.

Data storage 2424 can include one or more physical and/or non-transitory storage devices, such as read-only memory (ROM), random access memory (RAM), removable-disk-drive memory, hard-disk memory, magnetic-tape memory, flash memory, and/or other storage devices. Data storage 2424 can include one or more physical and/or non-transitory storage devices with at least enough combined storage capacity to contain computer-readable program instructions 2426 and any associated/related data structures.

Computer-readable program instructions 2426 and any data structures contained in data storage 2426 include computer-readable program instructions executable by processor(s) 2423 and any storage required, respectively, to implement and/or perform at least part of the herein-described techniques, algorithms, and methods, including but not limited to the data process algorithm discussed above at least in the context of FIG. 21B, the algorithm for selecting structures discussed above at least in the context of FIG. 21C, one or more functions of the herein-described XLink-DB system, and the method 2500 discussed below in the context of at least FIG. 25.

Example Methods of Operation

FIG. 25 is a flowchart for an example method 2500 for generating a display of multiple protein structures, in accordance with an example embodiment. Method 2500 can be carried out by a computing device, such as computing device 2420 discussed above in the context of at least FIG. 24B.

Method 2500 can begin at block 2510, where a computing device can receive data representing a first protein structure, such as discussed above at least regarding FIG. 21B.

In some embodiments, the computing device comprises a relational database configured to store at least the data representing the interaction between the first protein structure and the second protein structure.

At block 2520, the computing device can receive data representing a second protein structure, such as discussed above at least regarding FIG. 21B.

At block 2530, the computing device can receive data representing an interaction between the first protein structure and the second protein structure, such as discussed above regarding FIGS. 21B and 21C. In some embodiments, the interaction between the first protein structure and the second protein structure can include a cross-link between the first protein structure and the second protein structure, such as discussed above at least regarding FIGS. 21A, 21B, and 21C.

At block 2540, the computing device can generate a display. The display can be configured to show at least a portion of: the first protein structure, the second protein structure, and the interaction between the first protein structure and the second protein structure, such as shown in at least FIG. 21A.

In some embodiments, generating the display can include: after determining that the co-crystal structure for the first protein structure and the second protein structure is available, generating a first display of the co-crystal structure with an indication of the interaction between the first protein structure and the second protein structure.

In other embodiments, generating the display can include: after determining that the co-crystal structure for the first protein structure and the second protein structure is not available, generating a view of at least one site associated with the interaction between the first protein structure and the second protein structure.

In some embodiments, method 2500 can further include: determining a shortest distance between the first site and the second site, such as discussed above in the context of at least FIGS. 22 and 23.

In other embodiments, method 2500 can further include: determining whether a co-crystal structure for the first protein structure and the second protein structure is available, such as discussed above in the context of at least FIGS. 21B and 21C.

In still other embodiments, method 2500 can further include: performing a comparison of the interaction between the first protein structure and the second protein structure to a plurality of interactions stored in a reference interaction database; and determining a node distance for the interaction based on the comparison. In particular of these embodiments, the comparison can indicate that the interaction between the first protein structure and the second protein structure is a direct interaction. Then, determining the node distance for the interaction based on the comparison comprises determining a node distance of zero for the direct interaction. In other particular of these embodiments, the comparison can indicate that the interaction between the first protein structure and the second protein structure is an interaction involving N interactors, where N>0; i.e., the first protein structure and the second protein structure are indirectly interacting. Then, determining the node distance for the interaction based on the comparison comprises determining a node distance of N for the interaction involving N interactors.

EXAMPLES

The Examples that follow are illustrative of specific embodiments of the invention, and various uses thereof. They are set forth for explanatory purposes only, and are not to be taken as limiting the invention.

Example 1

Liquid Chromatography-Mass Spectrometry (LC-MS) Method

"Real-time Analysis for Cross-linked peptide Technology (ReACT)," combines chemical cross-linking with mass spectrometry (MS) of collisionally induced dissociation (CID) of cleavable cross-linked peptides and permits assignment of cross-linked peptides "on-the-fly." ReACT enables mass relationship-directed tandem mass spectrometry real-time targeting of released peptides for fragment analysis and identification. This increases the sensitivity, specificity and efficiency of cross-linked peptide identification within a single LC/MS data acquisition. ReACT can also be used to define topological features in protein complexes refractory to conventional structural biology approaches. Thus ReACT is a versatile approach that expedites the characterization of protein-protein interactions and identification of novel binding interfaces.

The general ReACT strategy is outlined in FIG. 1. First, high resolution $MS^1$ spectra are acquired and deconvoluted to obtain the neutral mass and charge state of all species detected. For any species with charge state equal to or greater than 4+, a high resolution $MS^2$ is acquired in a data-dependent fashion (e.g. selection of the top N most abundant 4+ ionic species). Charge state exclusion alternates between two parameter sets depending on the order, n, of each stage of $MS^n$ analysis. The set of parameters allows ions with charge state ≥4+ to be selected from high resolution mass spectral acquisition. This is done to focus instrument capabilities on cross-linked species for subsequent tandem mass spectrometry analyses.

Next, the $MS^2$ is deconvoluted to obtain the neutral mass and charge state of all species detected. All ions generated during high resolution $MS^2$ acquisition for which charge states are assigned are considered during the mass relationship discovery phase of the experiment. By identifying these relationships as the analytes elute from the LC column, ReACT effectively achieves real-time application of analysis strategies for PIR cleavable cross-linkers. More specifically, ReACT analysis identifies spectral features that satisfy a mass relationship that is based on the use of MS-cleavable cross-linkers. Namely, any two released and observed peptide masses added to the reporter mass must equal the observed precursor mass within a user definable mass tolerance, as set forth in equation (1):

$$PRECURSOR = REPORTER + PEPTIDE_1 + PEPTIDE_2, \quad (1)$$

where PRECURSOR is the mass of any selected precursor ion, REPORTER is the mass of the reporter ion (after cleavage of the PIR cross-linker) and $PEPTIDE_n$ is the mass of the released peptide n. This equation is applied during real-time data acquisition and requires checking N $MS^2$ high resolution product ions with each other. This amounts to $N^2/2$ calculations where N is equal to the number of detected isotopic distributions in the $MS^2$ pattern.

In some cases, in an effort to make the ReACT method more efficient, masses observed in the $MS^2$ spectra are only considered for further analysis if they also satisfy equation (2):

$$PEPTIDE_{for2} < PRECURSOR - REPORTER - STUMP, \quad (2)$$

where STUMP is the residual mass modification which remains on lysine residues after CID cleavage. In other words, a released peptide is considered only if its mass is less than the mass of its precursor ion minus the mass of the reporter ion minus the mass of any residual modifications left on the peptide. This limits the computational space of the calculation by only considering ions lower in mass than PIR partial cleavage products. Partial cleavage products result from incomplete cleavage of the PIR cross-linked products. In such a case, the reporter ion remains covalently linked to one of two peptides involved in the cross-link. While these products can represent a significant contribution to the overall signal of the fragmentation pattern, they are not used in determining whether equation 1 has been satisfied.

In the event that two ion masses from the $MS^2$ spectrum satisfy equation 1 and, optionally, equation 2, they are stored for targeted $MS^3$ analysis in the next scan cycle. In this way, no loss of instrument duty cycle occurs during the relationship calculation. During $MS^3$, peptide fragmentation spectra are acquired. Up to two $^{13}C$ offsets are considered to address cases of incorrect monoisotopic peak assignment for cross-linked precursors or product ions. A $^{13}C$ offset is defined as the mass difference in Daltons (Da) between $^{12}C$ and $^{13}C$.

The final step in the ReACT analysis is to extract the MS3 information and perform a database search with conventional proteome database search tools such as SEQUEST, Mascot, or others. Since ReACT uses mass relationships to direct $MS^3$ events, the number of spectra to be searched scales with the number of relationships found. The selectivity of ReACT results in reduced demand on instrument duty cycle, yet enables specific targeting of cross-linked peptides which are often observed with lower abundance. These species may be missed by traditional data-dependent analyses based on ion abundance alone. The loss of analysis time spent on species that do not meet these criteria is eliminated using ReACT, allowing for the detection of many more cross-linked peptide species than possible with any other current method.

For the ReACT experiments described below, all samples were analyzed on a custom dual linear RF ion trap Fourier transform ion cyclotron resonance mass spectrometer, hereafter referred to as the Velos-FT. The mass spectrometer was directly coupled with a Waters NanoAcquity UPLC system. Cross-linked peptide samples were loaded onto a trap column (3 cm×100 µm i.d.) packed with 200 A Magic-C4AQ (Michrom) using a flow rate of 2 µL/min of 99% solvent A ($H_2O$ containing 0.1% formic acid) and 1% solvent B (acetonitrile containing 0.1% formic acid) where they were washed for a total of 10 minutes. Peptides were then eluted from the trap column and separated by reversed-phase chromatography over an analytical column (30 cm×75 µm i.d.) packed with 100 A Magic-C4AQ at a flow rate of 200 nL/min using a linear gradient from 90% solvent A/10% solvent B to 60% solvent A/40% solvent B over 120 min for a 2 hr data acquisition or 240 min for a 4 hr data acquisition. The structure of a ReACT method consists of the following mass spectrometry data acquisition parameters. The first acquisition is a high-resolution precursor acquisition (50,000 resolving power (RP) @ 400 m/z). The second is a high resolution $MS^2$ acquisition on ≥4+ charge state isotope distributions. This requires the use of charge state exclusion. Dynamic exclusion is utilized with the following parameters: repeat count=2, repeat duration=15 s, dynamic exclusion list size=500, dynamic exclusion duration=30 s. FT preview mode and predictive automated gain control (pAGC) were not utilized. Monoisotopic precursor selection was used. A series of four RF ion trap $MS^3$ acquisitions were used to acquire fragmentation spectra of peptides observed in cross-linked relationships. These $MS^3$ events include acquisition on the 1+ and 2+ charge states of the peptides found in PIR relationships. Acquiring $MS^3$ spectra on two charge states has been instituted to overcome charge scavenging or unequal distribution of charge upon cleavage of the cross-linked complex.

The ReACT algorithm was written in ion trap control language (ITCL), a native language used with Thermo Electron mass spectrometers.

Example 2

Synthesis of Protein Interaction Reporter (PIR) Cross-Linkers

The PIR cross-linker molecules used in these examples have several engineered features, which aid in the successful identification of cross-linked sites: a biotin affinity tag to allow for enrichment of low abundance cross-linked species, two low energy CID cleavable bonds to release cross-linked peptides and allow for independent sequencing, and a reporter ion to indicate the presence of a cross-linked product.

PIR synthesis was performed using solid phase peptide synthesis (SPPS) methods (Merrifield, 1964, *Biochemistry* 3:1385-90). The Endeavor 90 (Apptec, Louisville, Ky.) SPPS unit was used for all PIR synthesis steps with the exception of the final N-hydroxy ester (NHX, where X=succinimide or phthalimide) ester formation step. Biotin Rink-PIR (BRink) and Rink-PIR (2Rink) synthesis was as follows. The super acid sensitive resin (SASRIN) with a glycine residue pre-coupled was utilized (Bachem, Munich, Germany). Synthesis of the cross-linker proceeds through fluorenylmethyloxycarbonyl (Fmoc) N-terminally protected SPPS methods (Paramelle et al., 2012, *Proteomics* 13:438-56). Additions to the resin occur in order and were the following, Fmoc-Lys (biotin), Fmoc-Lys (Fmoc), Fmoc-Rink (all amino acids obtained from Bachem), and succinic anhydride (Sigma-Aldrich, St. Louis, Mo.). 2Rink is synthesized through the same series of steps with the exception of the addition of Fmoc-Lys (biotin). The activated NHS-ester form of the cross-linker is created in a final esterification step immediately prior to use with TFA-NHS. Overall yield for this synthesis was ~90%. Purity was confirmed by direct infusion ESI-MS analysis. Cross-linker was cleaved from the resin using 1% trifluoroacetic acid (TFA) in methylene chloride and purified using a semi-preparative partisil C18 column (Whatmann, United Kingdom) at low pH to prevent hydrolysis of the NHS ester. BRink and 2Rink were dissolved in dimethylsulfoxide to a concentration of 100 mM.

Biotin Aspartate Proline-PIR (BDP) cross-linker synthesis was also accomplished using Fmoc chemistry as follows. SASRIN-glycine resin was used for the solid support. Amino acid additions to the resin occur in order and were the following: Fmoc-Lys (Biotin), Fmoc-Lys (Fmoc), Fmoc-Pro, Fmoc-Asp (otBu), and succinic anhydride. The activated NHX form of the cross-linker is created in a final esterification step immediately prior to use with TFA-NHX (X=phthalamide or succinimide). Cleavage from the solid support and de-protection of Asp (otBu) was performed simultaneously using 95% TFA/5% methylene chloride. Purification was performed immediately subsequent to Asp de-protection and cleavage via diethyl ether precipitation using 1:15 (cleavage mixture:diethyl ether). Diethyl ether solution was centrifuged at 3400 g to pellet precipitate. Diethyl ether was decanted and pellet was dried to yield ~90-95% pure BDP-ester. Purity was assayed via direct infusion ESI-MS analysis. BDP was dissolved in dimethylsulfoxide to a concentration of 500 mM to form a stock solution.

Example 3

Data Interpretation and Sequence Identifications

ReACT provides a list of cross-linked relationships observed during an entire data acquisition. Raw mass spectrometry data is converted to mzXML format using ReAdW (ver. 4.3.1). $MS^2$ accurate precursor mass and $MS^3$ fragmentation patterns are extracted from the mzXML and converted to Mascot Generic Format (mgf) for Mascot (version 2.3.1) sequence database searches using MzXML2Search (Ver. 4.4) or mzXML was searched directly using SEQUEST (version UWPR2011.01.1). Mascot searches were conducted with a 10 ppm precursor mass tolerance and 0.8 Da fragment ion tolerance. SEQUEST searches were conducted 10 ppm precursor mass tolerance and a 0.36 Da fragment tolerance (0.11 Da fragment offset). The most probable match for each query is accepted (with an expectation value threshold <0.05) and mapped back to the cross-linked relationship for in vitro or standard protein experiments. Sequence databases utilized here include standard proteins (21 sequences including isoforms), SwissProt *E. coli* (4178 sequences) (http://www.uniprot.org), SwissProt *H. sapiens* (64,984 sequences) (http://www.uniprot.org), and a database containing cAMP dependent protein kinase regulatory subunit I alpha and beta (RIα and RIβ) and cAMP-dependent protein kinase catalytic domain (pkaC). False discovery during sequence identification for cell experiments was estimated using well-described reverse database search methods. Relationship discovery in real-time required a tolerance of 20 ppm between the putative cross-linked precursor and the cross-linked peptide relationship. This mass tolerance was selected for relationship discovery through balancing sensitivity of relationship discovery with false relationship discovery. False relationship discovery was estimated by performing ReACT analysis on a yeast lysate digest without cross-linker added (<5% of all acquired $MS^2$ result in false mass relationships).

Figure 3:
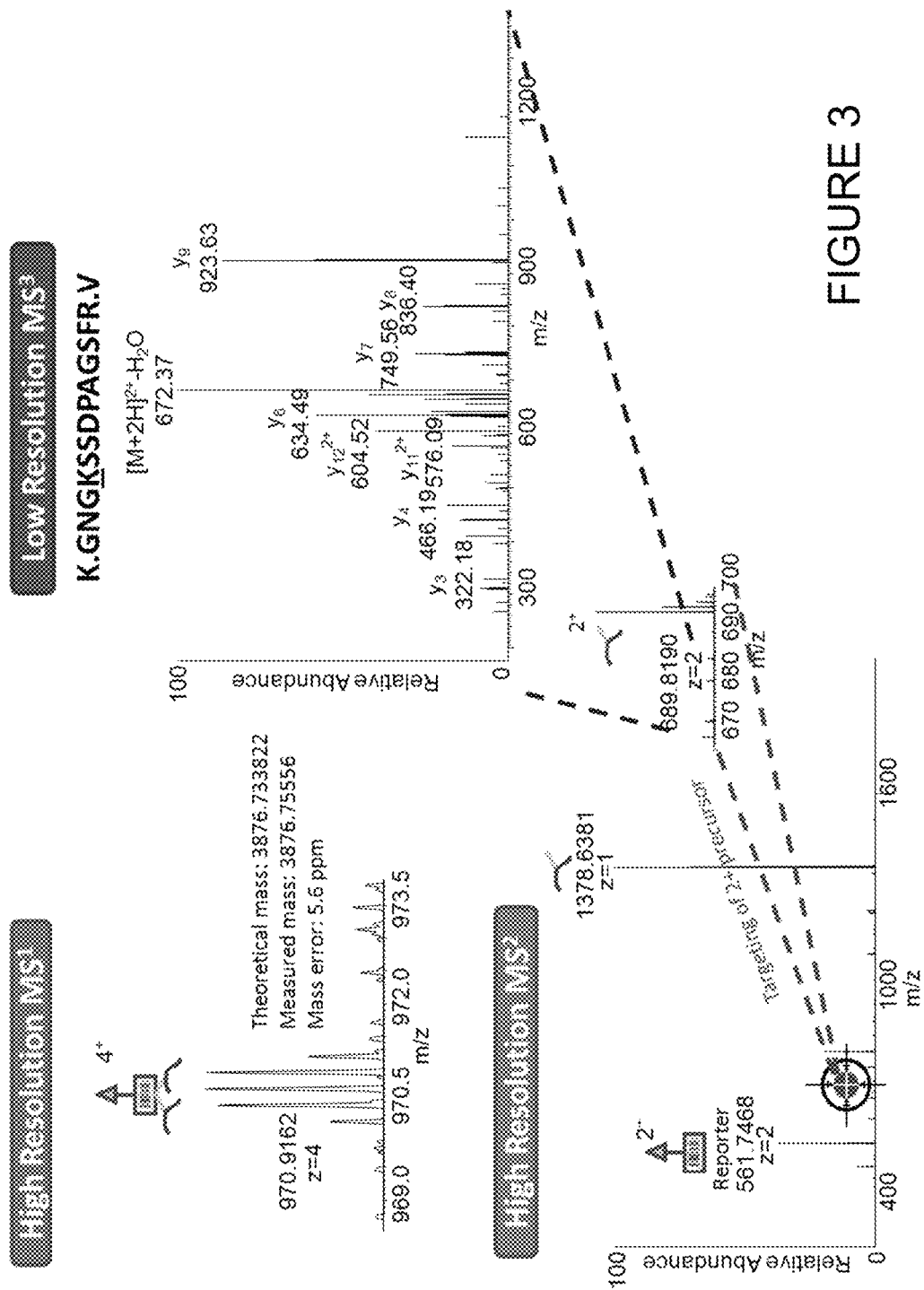
FIG. 3. REACT algorithm permits targeting released peptide products from cross-linked pairs to increase peptide identification probability.

Singly charged ions often yield low quality peptide fragmentation patterns when analyzed with ion trap-based instrumentation. The ReACT algorithm includes the ability to target higher charge state released peptides even if the signal-to-noise ratio of higher charge state ions is too low to be selected or even observable within the mass spectrum. It has been shown previously that quadrupole ion storage devices are prone to exclusion of low abundance ions if simultaneously accumulated with more abundant ions (Kim et al., 2005, *Science* 307(5710):690; Boettcher et al., 2011, *Structure* 19(2):265). Instrument duty cycle has been reduced as described above. The analysis time liberated by using the real-time targeted approach can be utilized here in the accumulation of low abundance ions. The targeting of low abundance, higher charge ions in some cases results in a cross-linked peptide identification, which would otherwise not be obtainable with 1+ fragmentation patterns alone. This targeting feature of ReACT is illustrated in FIG. 3, where the 2+ ion for the released peptide is observed at a low intensity near the noise level, while the 1+ ion is the base peak in the spectrum. By specifically targeting the 2+ ion for $MS^3$, a fragmentation spectrum useful for peptide sequence identification was acquired. However, $MS^3$ analysis of the 1+ ion of this peptide did not yield sufficient fragment ion information to obtain sequence identification.

Example 4

Structural Modeling

All models were created and rendered using Pymol (Delano Scientific). In vitro PKA structural models were created using coordinates from PDB identifiers 1RGS, 2QCS, and 3IM3. The cAMP binding cassette B in the free RIα was aligned with the corresponding region in the RIα-catalytic subunit complex to show the movement of cAMP binding cassette A. *E. coli* tryptophanase structural model was created using coordinates from PDB identifier 2OQX. *E. coli* 30S ribosome structural model was created using coordinates from PDB identifier 3FIH. RNA sequence in the *E. coli* ribosome was omitted from the rendering process. The human nucleosome structural models were created using coordinates from PDB identifier 3A6N.

Example 5

In Vitro Cross-Linked Protein Analysis

A set of purified proteins were labeled to illustrate that ReACT is useful for real-time analysis of PIR cross-linked peptides.

Alcohol dehydrogenase (*S. cerevisiae*), α-lactalbumin (*Bos taurus*), carbonic anhydrase (*Bos taurus*), cytochrome C (*Equus caballus*), hemoglobin (*Homo sapiens*), ribonuclease A (*Bos taurus*), and myoglobin (*Equus caballus*) were all obtained from Sigma Aldrich (St. Louis, Mo.) and used as received. Each protein was dissolved at a concentration of 1 mg/mL in phosphate buffered saline (PBS) buffer, pH 7.4. The cross-linking reaction was performed by adding BDP-NHS at a final concentration of 1 mM and incubating the reaction solution at room temperature for 1 hour with constant mixing. A second sample of ribonuclease A was labeled using 2Rink at the same concentration from the multiple cross-linker experiment. After cross-linking disulfide bonds were reduced using 5 mM tris(2-carboxyethyl) phosphine (TCEP) and the resulting free thiols were alkylated using 10 mM iodoacetamide (IAA). Digestion was carried out at using a 1:200 w/w ratio of sequencing grade modified trypsin (Promega, Madison, Wis.) to protein and incubating at 37° C. overnight with constant mixing. The samples were de-salted using C18 Sep-Pak (Waters Corporation, United Kingdom) and dried in a centrifugal concentrator (Genevac, Gardiner, N.Y.). The cross-linked, digested samples were redissolved in solvent A then stored at −80° C. until LC-MS analysis.

The data resultant from this set of experiments (not shown; see Weisbrod et al., 2013, *J. Proteome Res.* 12:1569-79) show an unambiguous α-β hemoglobin cross-link, as well as unambiguous homodimeric cross-links supporting protein dimerization of ribonuclease A and carbonic anhydrase. The presence of concentrated tryptic peptides from each protein, approximately 100 times more abundant than cross-linked products, provided a more appropriate test for the algorithm. Some examples within the data were identified with a signal-to-noise ratio of ~2. This illustrates the ability of ReACT to extract useful information, even from low intensity ions.

One important feature of ReACT is that the algorithm is customizable for use with any mass spectrometry cleavable cross-linker including linkers with mono, bi, or higher order CID cleavage sites.

Figure 4A:
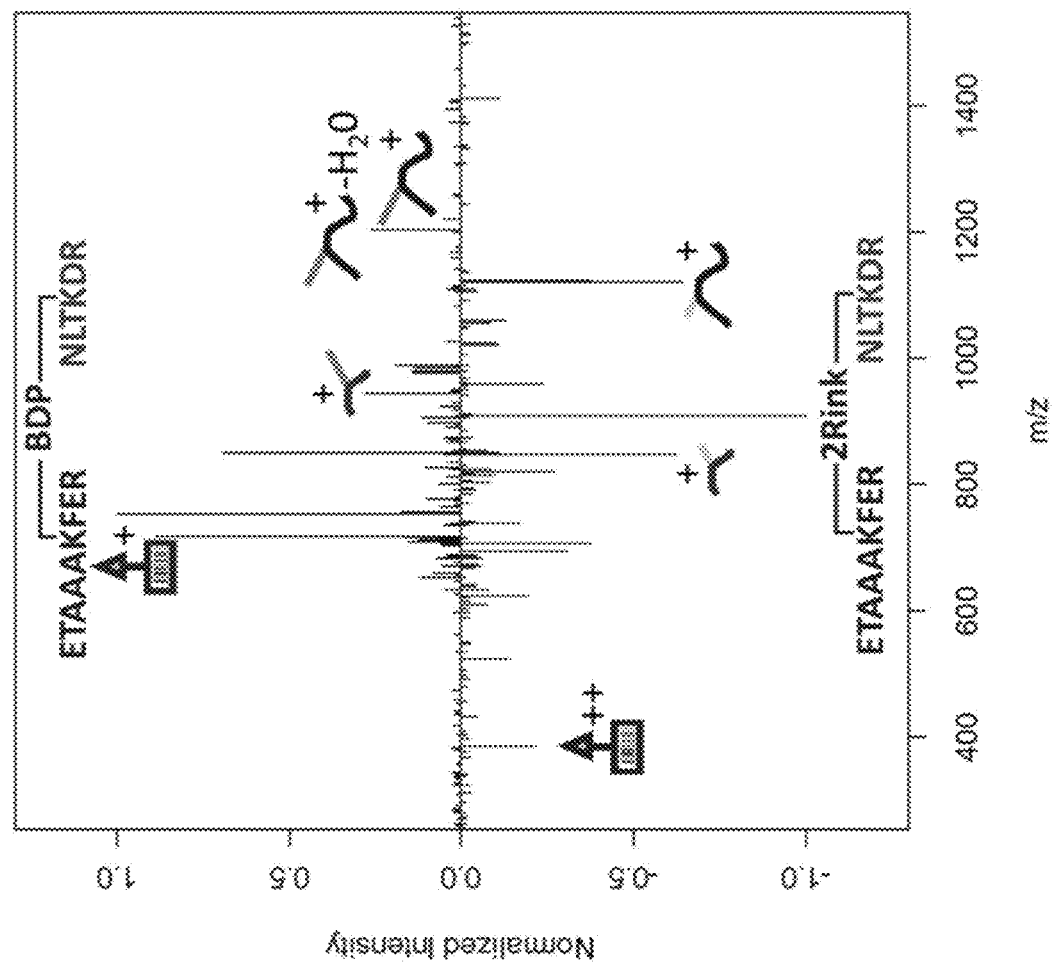
Figure 4B:
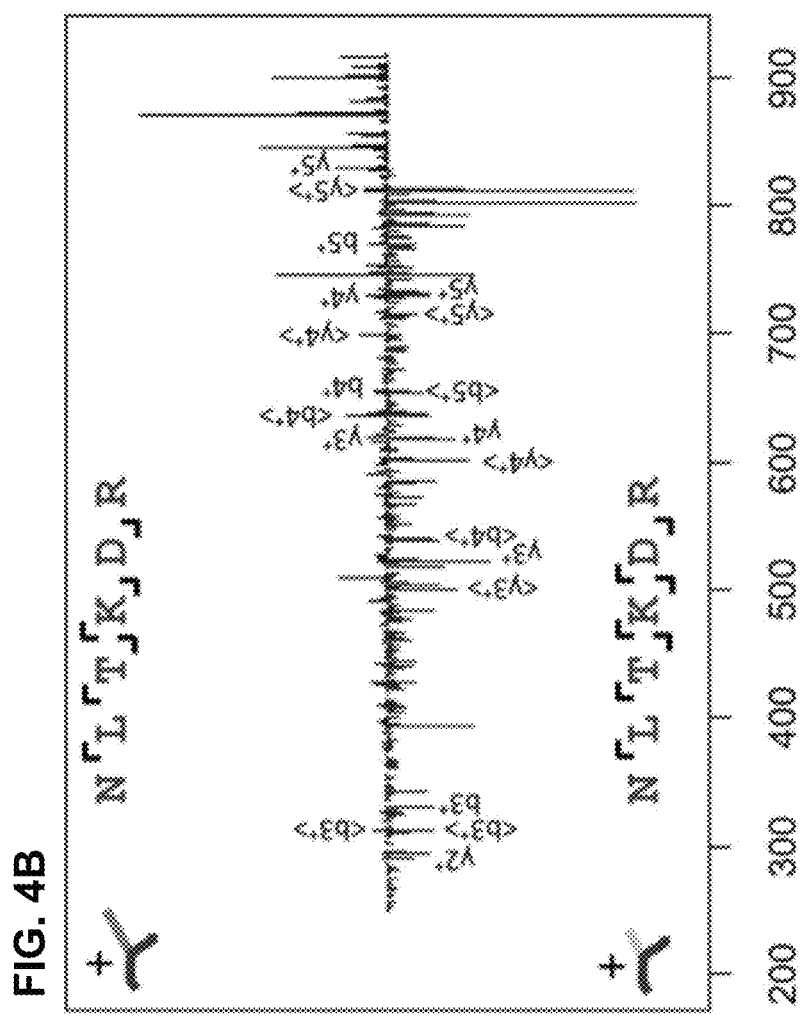

To demonstrate this flexibility, Ribonuclease A (RNase A) was cross-linked with two different PIR molecules, 2Rink and BDP, 14,20 and the ReACT approach was applied. For this sample, the respective reporter masses were entered into ReACT so that ions matching either the mass relationship for 2Rink or for BDP would be identified as cross-linked peptide pairs. In either case, ReACT selected the released peptide ions that fulfilled the relationships in Equation 1 for MS3 analysis. BDP and 2Rink labeled RNase A digests were mixed in equimolar ratios and four fully identified cross-linked products are discussed next. Of the four, two are obtained from BDP, and two are obtained from 2Rink. All four share a single peptide with a unique second peptide. One pair overlaps between the two linkers (ETAAA KFER-NLTKDR; SEQ ID NOS: 13-14). In FIGS. 4A-4C, this cross-linked site has been identified with both linkers within a single ReACT experiment. These two PIR cross-linkers differ in their engineered cleavage site. In BDP, the proline-aspartate amide bond acts as the low energy cleavage site, whereas, in 2Rink it is the tertiary amine within the Rink core structure. The permanent lysine modification or "stump" mass of these linkers differs (99.032 Da for 2Rink or 197.032 Da for BDP). Therefore, peptides identified with this site have b and y fragment ions with different mass shifts due to the modification (FIGS. 4A and 4B). Although this effort is focused on the initial description and application of ReACT, these results demonstrate the capacity of multiple simultaneous cross-linker analyses with ReACT. This feature of ReACT will benefit sample analyses with multiple cross-linker molecules, e.g., with variable structure lengths, reactivity, or physiochemical properties, and may further increase the number of observed cross-linked sites from cells.

Example 6

ReACT Analysis of Protein-Protein Interactions in *E. coli*

In vivo cross-linking of *E. coli* was accomplished as follows. *E. coli* K12 cell suspensions were harvested at O.D. 0.6-0.8. The cells were pelleted and washed 5 times with 1 mL PBS before cross-linking. A 150 µL cell pellet was re-suspended in 150 mL PBS and biotin-aspartate-proline N-hydroxyphlalamide (BDP-NHP) PIR cross-linker was added to the suspension to a final concentration of 10 mM. The reaction was carried out at 4° C. for 1 hr. The cells were lysed by heating to 95° C. in 4% sodium dodecylsulfate (SDS) 1×Tris buffer at pH 8.5. The sample was ultrasonicated to shear DNA. The sample was centrifuged at 16 kg for 10 min to remove insoluble material. It was then added to a 30 kDa molecular weight cut-off (MWCO) filter (Millipore, Billerica, Mass.) and concentrated by centrifugation at 7.5 kg for 30 min. A protein extract yield of 2.0 mg/mL was determined using a Coomassie Plus assay (Pierce, Rockford, Ill.). The sample was reduced, alkylated, and digested as described above. Strong cation exchange (SCX) fractionation of the sample was performed using Macro SCX Spin Columns (Nest Group Inc., Southborough, Mass.) and ammonium acetate in 25% acetonitrile, 75% water for elution. Fractions were collected at 0, 50, 80, 300, 500, and 1000 mM ammonium acetate. Prior to affinity enrichment each fraction was de-salted using C18 Sep-Pak 50 cc (Waters Corporation, United Kingdom). The fractions were biotin affinity enriched for BDP cross-linked peptide products using Ultralink Monomeric Avidin (Pierce, Rockford, Ill.). To each fraction 300 µL of settled avidin resin was added in 500 µL of 100 mM ammonium bicarbonate. Enriched cross-linked peptide samples were stored at −80° C. until LC-MS analysis.

ReACT has been developed to provide selectivity in LC-MS$^n$ analyses to focus on only those ions which are likely cross-linked peptides. This selectivity is illustrated in an example ReACT dataset acquired from *E. coli* cells (FIG. 4).

Figure 5B:
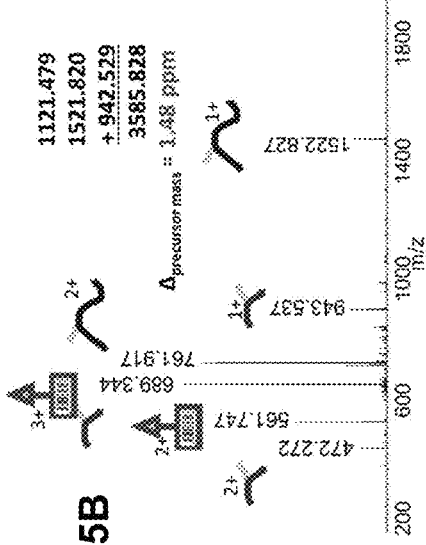
FIGS. 5A-5E show an example of ReACT data acquired from PIR-labeled *E. coli* cells.
Figure 5A:
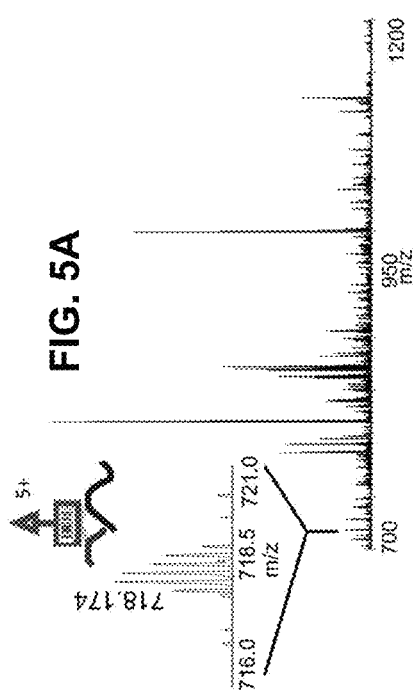
Figure 5E:
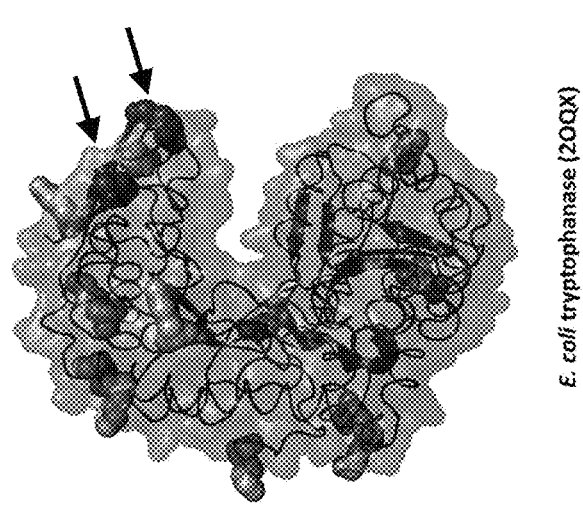
Figure 5C:
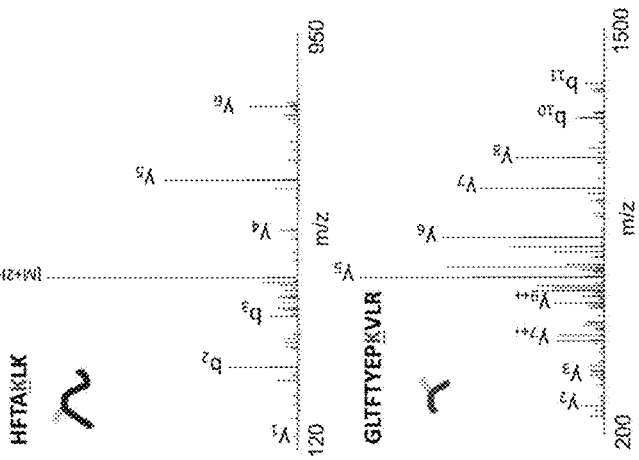
Figure 5D:
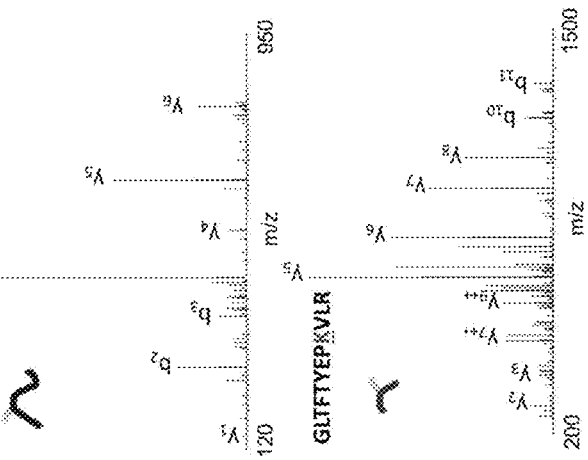

ReACT selectivity for cross-linked species is achieved first on the MS$^1$ precursor stage through exclusion of ions with charge less than or equal to 4+, since two peptides covalently linked will possess on average 4+ charge state or greater. Many potential analytes are present within the spectrum in FIG. 5A; however, ReACT application results in selection of only those ions with 4+ charge state or higher. In fact, the analyte of interest, 718.174 m/z, is the 576th most abundant peak within the spectrum and would likely never have been sampled by conventional intensity-driven data dependent analyses. Requirement of the CID cleavable linker mass relationships to be observed with narrow mass tolerance (±20 ppm) imparts additional specificity in the analysis of the selected high charge state ions. In the example shown, the measurement error between the observed precursor and sum of masses of the relationship (Equation (1)) is less than 1.5 ppm (FIG. 5B). Typically, mass measurement error for observed cross-linked relationships is less than or equal to 5.0 ppm which significantly reduces false relationship discovery. Upon successful relationship detection, ReACT directs MS$^3$ events to automatically acquire fragment ion spectra for sequence identification of the released peptides (1+ and 2+ charge states for each). Both peptides identified in this example belong to tryptophanase (TNAA_ECOLI). The cross-linked sites were mapped onto the existing crystal structure for *E. coli* tryptophanase (PDB: 2OQX), where the lysine residues highlighted with arrows represent the cross-linked sites in this example (other residues shown in space-filling form indicate other cross-linking sites found; FIG. 5E).

Previously, PIR technology was employed without ReACT to study PPIs and topologies in vivo within *E. coli* (Zheng et al., 2011, *Mol. Cell Proteomics* 10(10): M110.006841). A total of 65 cross-linked peptide pairs were identified using previously published mass spectrometry analysis methods and informatics tools. Conclusive identification of these 65 cross-linked pairs was a labor intensive process, requiring multiple LC-MS runs, multiple sample preparations, and significant efforts in data processing and analysis.

In contrast, ReACT enabled analysis of 519 fully identified cross-linked peptide pairs in *E. coli*, where both released peptides were identified using SEQUEST with false discovery rate (FDR) below 5% (data not shown; see Weisbrod et al., 2013, *J. Proteome Res.* 12:1569-79). Because identification of each peptide proceeds via independent $MS^3$ in ReACT, it is possible that only a single peptide is identified by $MS^3$ while the other peptide fragmentation pattern fails to yield a conclusive assignment at the 5% FDR cutoff. Within *E. coli*, an additional 539 cross-linked relationships were observed in this category. In these cases, accurate released peptide masses and the number of observed matching fragment ions were used to make putative sequence assignments to the peptides above the 5% FDR threshold. Even though the observed SEQUEST score for these ions did not fall within the 5% FDR cutoff, in all cases the accurate peptide mass and the largest number of matching fragment ions search yielded the top scoring SEQUEST candidate. Inclusion of these assignments increased the total number of cross-linked pairs to 1058 cross-linked peptides from *E. coli* (data not shown; see Weisbrod et al., 2013, *J. Proteome Res.* 12:1569-79). ReACT greatly advances the ability to identify cross-linked peptides from intact cellular systems and has enabled acquisition of the first set of cross-linked peptides from eukaryotic cells (FIG. 5).

ReACT is a shotgun proteomics approach that advances peptide sequence identification for peptides in cross-linked relationships. Identified peptides are used to infer protein identity. However, in contrast to typical shotgun proteomics experiments where identification of many peptides from a single protein supports that protein or protein family's presence within the sample, a single cross-linked peptide may be the only reactive site identified from an entire protein sequence. It should be noted that this same issue exists for all large-scale cross-linking and post-translational modification studies. To date, this remains a difficult problem to adequately address in large-scale proteomics data sets where modifications are considered. ReACT analysis results in identification of two peptides cross-linked to each other that may or may not belong to the same protein/family. Within the high confidence *E. coli* cell data presented here, 81% of the cross-linked sites are reported to have both peptides non-redundant (described by a single protein) within the database. Additionally, 12.4% (88 of 708 identified) one of the peptides associated with a cross-linked site are redundant (peptide sequence shared by multiple proteins). Finally, in only 1.5% (11 of 708 identified) of the cases are both peptides redundant in the database. (Data not shown; see Weisbrod et al., 2013, *J. Proteome Res.* 12:1569-79.)

For peptides that are redundant among two or more protein sequences, putative protein identities were inferred through a set of logical criteria derived to address this issue and described here. First, a peptide is preferentially assigned to a single protein from the list if that peptide can be mapped to the same protein as the other peptide in the cross-linked site. This logical assumption is derived from the fact that lysine residues nearby any reacted lysine site will predominantly be within the same protein sequence. Thus, if one of the redundant proteins is the same as the protein that yielded the other non-redundant cross-linked peptide, this entity is chosen. If this step cannot be satisfied, the redundant peptide is preferentially assigned to a protein from the pool of proteins resultant from all non-redundant peptides identified within ReACT data sets. This logical assumption arises from the fact that because the protein was identified as cross-linked on other sites, cross-linker accessibility and reactivity with this protein is demonstrated. If one or more proteins in this pool contain the redundant peptide sequence, the proteins are assigned on the basis of their order of appearance within the database. Finally, if neither of the associations above can be made, a putative protein ID is assigned on the basis of the order of appearance within the entire protein database. With acquisition of larger cross-linking data sets where the number of redundant peptides is likely to become larger, advanced protein assignment methodologies will be implemented. These efforts will rank such assignments on the basis of the frequency of representation of the protein family within the database, relative genomic distance between the two cross-linked proteins (e.g., are the genes for the two proteins within the same operon or under control of a single promoter), established protein interaction databases, or based on proteins uniquely identified in other cross-linked sites (or e-values).

The primary utility of cross-linking data from cells includes the identification of PPIs and topologies directly from their native physiological environment. The size of resultant ReACT datasets present a significant wealth of structural information. Key macromolecular interactions in *E. coli* and human cells include ribosome and histone structures for which structural data are available and ReACT data on these complexes is discussed below. Nonetheless, the entire datasets of cross-linked peptides from *E. coli* and human cells are presented in Weisbrod et al., 2013, *J. Proteome Res.* 12:1569-79 and Chavez et al., 2013, *Mol. Cell Proteomics* 12(5):1451-67, which are expressly incorporated by reference herein for all purposes.

In *E. coli*, ribosomes have two subunits and are comprised of RNA and protein molecules with 56 different protein sequences. FIG. 6 illustrates the *E. coli* ribosome structure (PDB: 3FIH) with 3 of 4 inter-protein cross-linked pairs identified from cells in this study using ReACT. In this figure, all heterocross-linked peptides are presented where linkage between two different ribosomal protein sequences was observed. For clarity, other ribosomal intra-protein cross-linked pairs (111 cross-linked pairs) that were identified are omitted; however, these cross-links still provide unique topological information such as distance constraints between lysine residues. Also omitted are inter-protein cross-linked pairs between ribosomal and non-ribosomal proteins e.g. elongation factor TU. In the ribosome, we were able to assign 3 of 4 heterodimeric cross-links directly to crystallographic data (all cross-link sites are <25 A). One observed cross-linked pair was not mapped since the available ribosomal crystal structure does not contain these proteins (RL7_ECOLI and RL10_ECOLI). However, this cross-link between RL7_RL10 illustrates how ReACT can provide new information about well-studied systems directly from cells. For the first time we are able to validate crystallographic measurements of ribosome against data obtained directly from cells using ReACT. Many (160<5%

FDR) other non-ribosomal heterodimeric linkages are present within these data which allows new knowledge to be gained beyond previously characterized PPIs and topologies.

Interprotein cross-links discovered with ReACT provide new information about protein interactions directly from *E. coli* cells. These data can be broken down into three separate categories: previously observed, likely, and uncharacterized. To do this, the interprotein cross-link results presented in FIG. 5 were compared to available protein interaction data from Ecocyc.org (EciD—protein interaction database). From this comparison, 39% of the PPIs presented here have been observed previously through alternative experimental techniques (yeast two hybrid, coIP, etc.). However, even for these known interactions, the data acquired with ReACT provide new topological information on these and help visualize how these proteins interact as they exist inside cells. Moreover, 50% of the PPIs discovered using ReACT were found within one node of a known interacting pair discovered using other experimental techniques. That is, 50% of the PPI discovered in cells with ReACT include proteins that are known to participate in the same complexes, but not previously known to interact directly. For example, protein A interacts with protein B and protein B interacts with protein C, but protein A is not known to interact directly with protein C based on empirical data. Here, these PPI's are classified as secondary interactors and include for example, N-acetylmuramoyl-L-alanine amidase (AmiA) that has been shown to interact directly with proteins in the 30 s (rpsA and rpsO) and the 50 s (rplD) ribosome. Although direct cross-linked sites between AmiA and rplD, rpsA, or rpsO were not observed, AmiA was identified as a cross-linked product with rplB (a known direct interaction partner of rplD) of the 50 s ribosome with two unique sites. Although this and other interactions appear in existing databases as secondary interactions, in vivo cross-linking results made possible with ReACT illustrate they are present in cells close to one another and can be linked directly together. If these proteins are not directly interacting, the cross-linking data suggests they are at least participating in the same complexes at the same time with nonrandom relative orientation. In summary, 89% of the interactions identified with ReACT are previously known as direct or secondary interactors. Excitingly, ReACT yields new topological data on all these interactions as they exist in cells.

Example 7

In Vivo Cross-Linking and PPI Identification in HeLa Cells

HeLa cells were grown at 37° C. under a humidified atmosphere containing 5% $CO_2$ in Dulbecco's modified Eagle medium (DMEM) containing 10% fetal bovine serum (FBS) and 1% penicillin/streptomycin until they reached 80% confluence. Cells were harvested by trypsinization and collected into centrifuge tubes. The cells were pelleted and washed 5 times with 1 mL PBS before cross-linking. A 150 µL cell pellet was re-suspended in 150 mL PBS and BDP-NHP cross-linker was added to the suspension with a final concentration of 10 mM. The reaction was carried out at 4° C. for 1 hr. The cells were lysed by heating to 95° C. in 4% sodium dodecylsulfate (SDS) lx Tris buffer at pH 8.5. The sample was ultrasonicated to shear DNA. The sample was centrifuged at 16 kg for 10 min to remove insoluble material. It was then added to a 30 kDa molecular weight cut-off (MWCO) filter (Millipore, Billerica, Mass.) and concentrated by centrifugation at 7.5 kg for 30 min. A protein extract yield of 2.0 mg/mL was determined using a Coomassie Plus assay (Pierce, Rockford, Ill.). The sample was reduced alkylated and digested as described above for the BSA sample. Strong cation exchange (SCX) fractionation of the sample was performed using Macro SCX Spin Columns (Nest Group Inc., Southborough, Mass.) and ammonium acetate in 25% acetonitrile, 75% water for elution. Fractions were collected at 0, 50, 80, 300, 500, and 1000 mM ammonium acetate concentration. Prior to affinity enrichment each fraction was de-salted using C18 Sep-Pak 50 cc (Waters Corporation, United Kingdom). The fractions were biotin affinity enriched for BDP cross-linked peptide products using Ultralink Monomeric Avidin (Pierce, Rockford, Ill.). To each fraction 300 µL of settled avidin resin was added in 500 µL of 100 mM ammonium bicarbonate. Enriched cross-linked peptide samples were stored at −80° C. until LC-MS analysis.

Figure 20A:
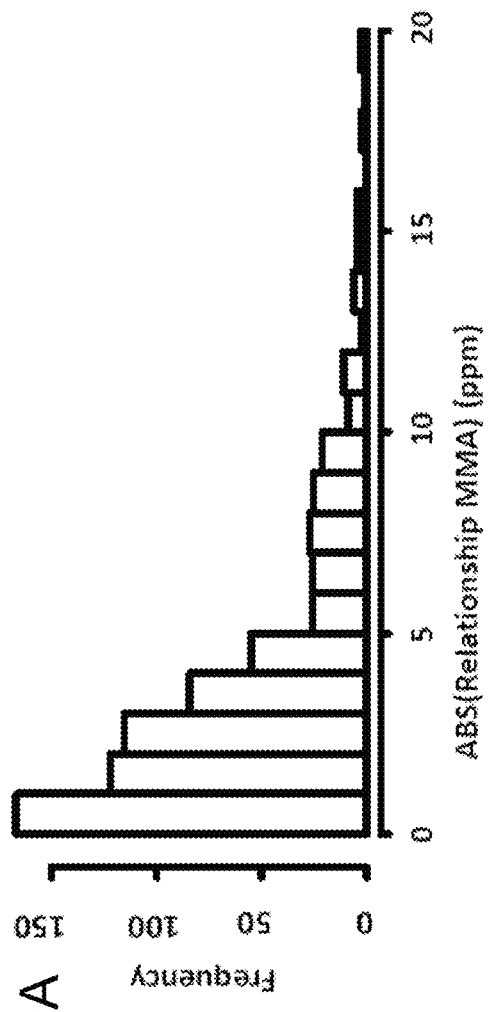
FIGS. 20A-20B. Histogram of relationship mass error determined by ReACT for both *E. coli* (FIG. 20A) and HeLa cell experiments (FIG. 20B).
Figure 20B:
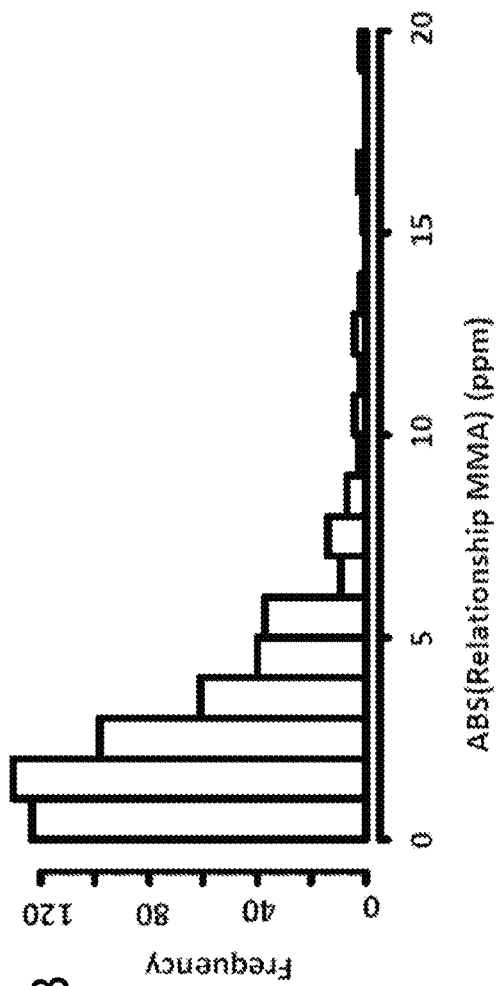

Although fewer in number (260 cross-links at 5% false discovery rate (FDR)), it is important to note that HeLa cell data were generated from fewer biological replicates than the *E. coli* data above. Nevertheless, these efforts represent the first report of a large-scale cross-linked peptide dataset from a human cell line. A majority of the identified cross-linked peptide relationships from *E. coli* and HeLa cells were observed with mass errors <5 ppm, even though the tolerance for cross-linked peptide relationship discovery was set to ±20 ppm (FIGS. 20A-20B; see also Weisbrod et al., 2013, *J. Proteome Res.* 12:1569-79 and Chavez et al., 2013, *Mol. Cell Proteomics* 12(5):1451-67). Additionally, a majority of the cross-linked peptide pairs detected and presented here resulted from cross-link types designated as "intra-protein" (FIGS. 6A, 6D), where both peptides originated within the same protein sequence. Homodimer cross-links and intraprotein cross-links both are likely present in this category, since no comprehensive effort has been made to differentiate the two types.

Figure 6B:
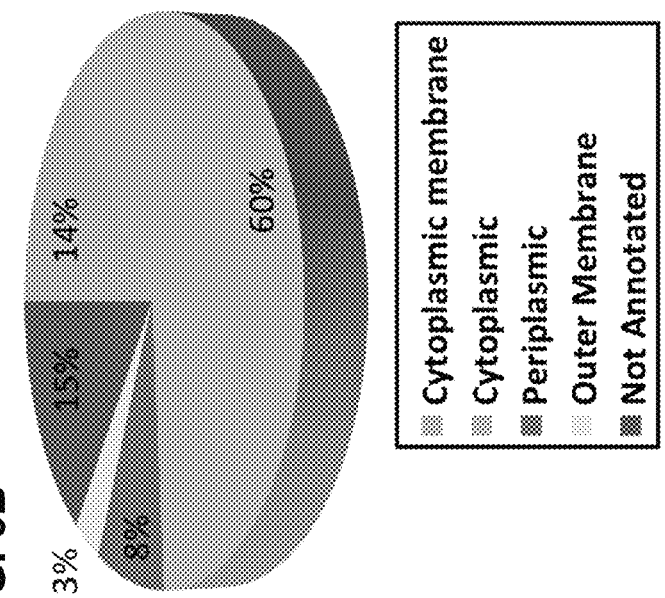
FIGS. 6A-6F. Cellular cross-linking results obtained with ReACT from both *E. coli* and HeLa experiments.
Figure 6A:
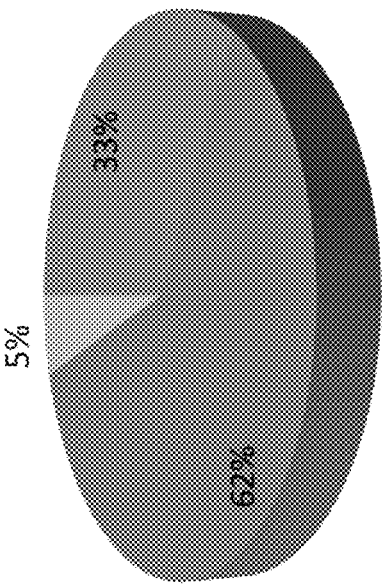
Figure 6C:
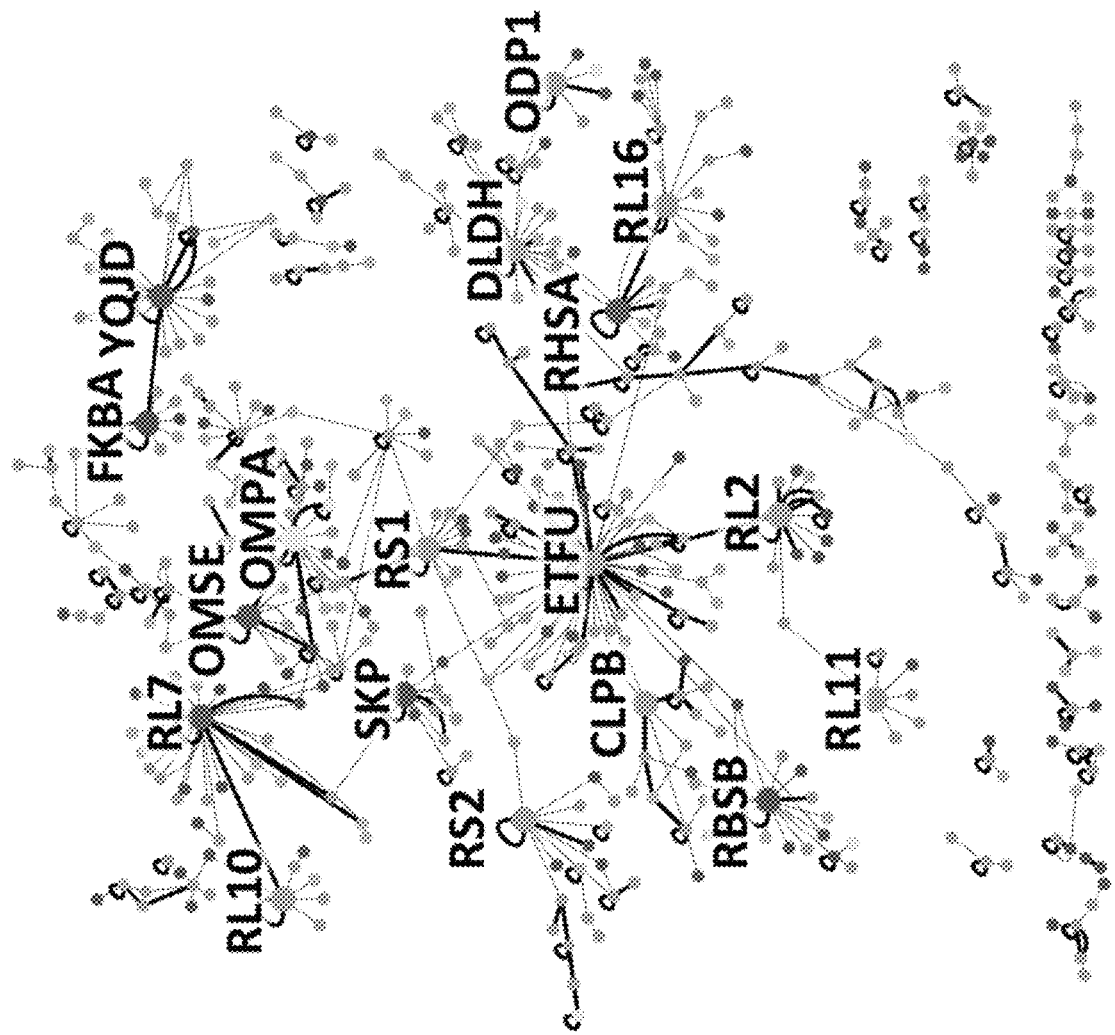
Figure 6E:
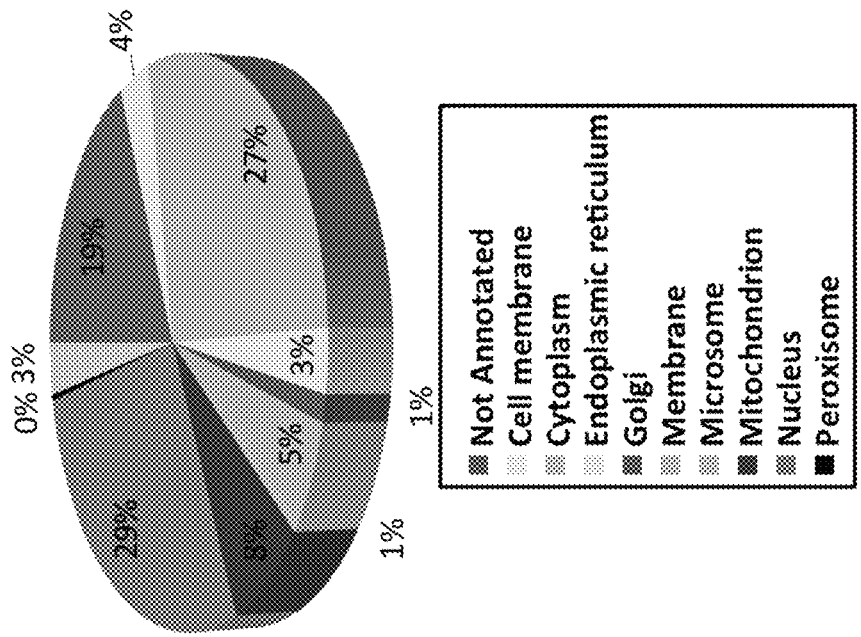
Figure 6D:
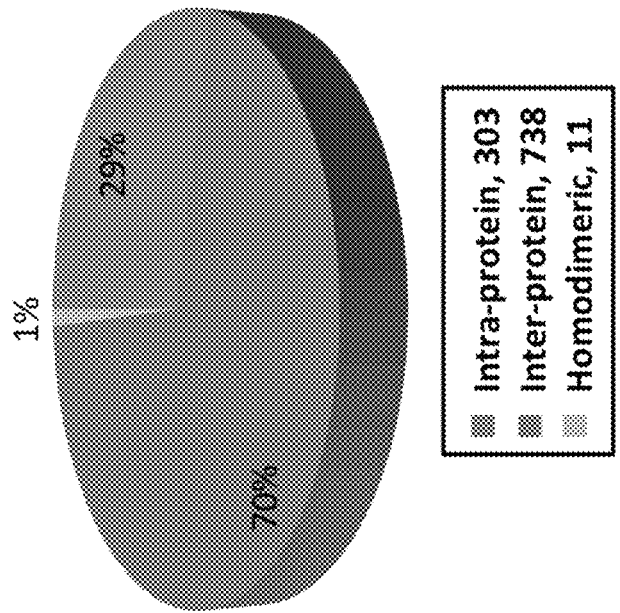
Figure 6F:
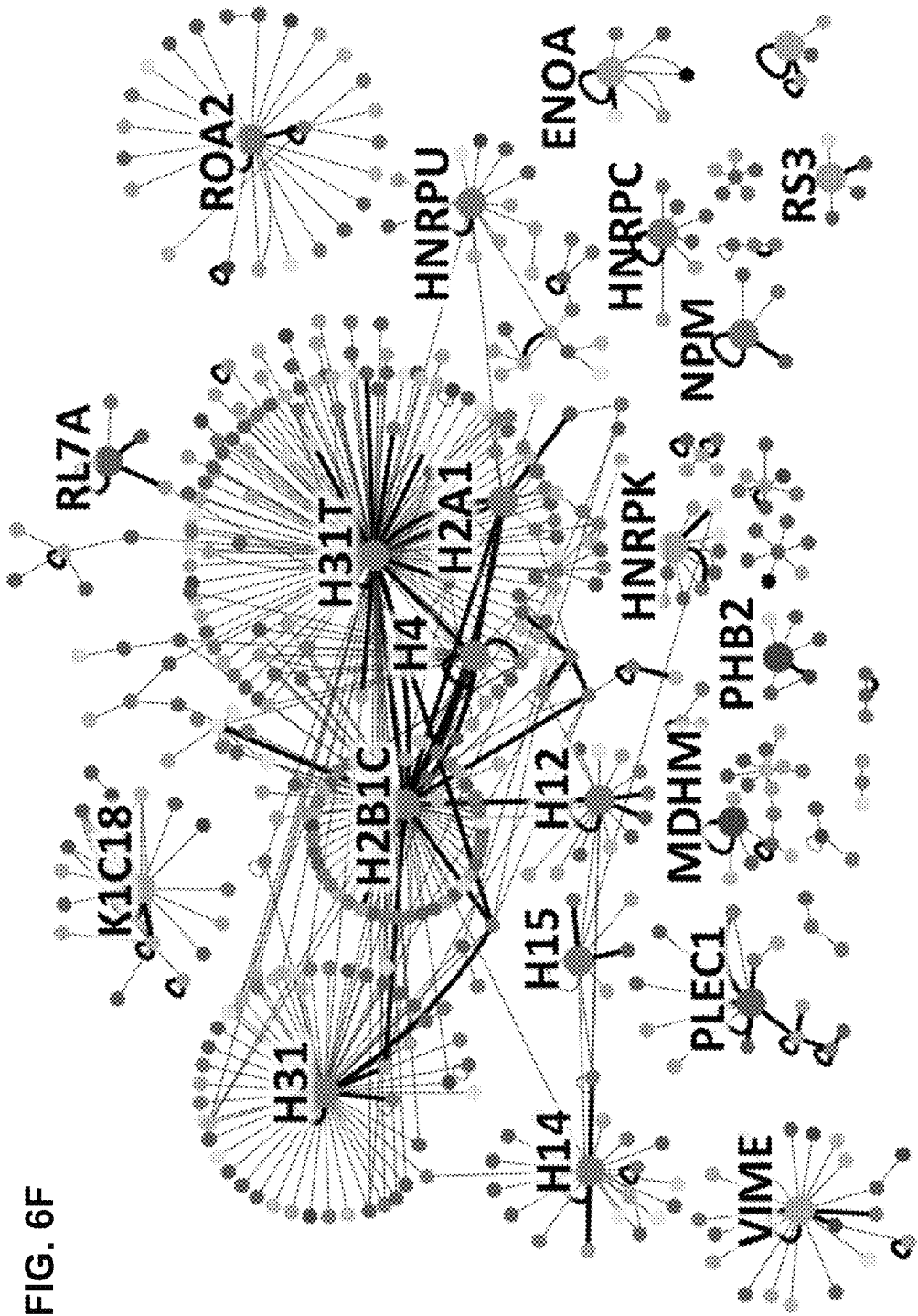
Figure 7:
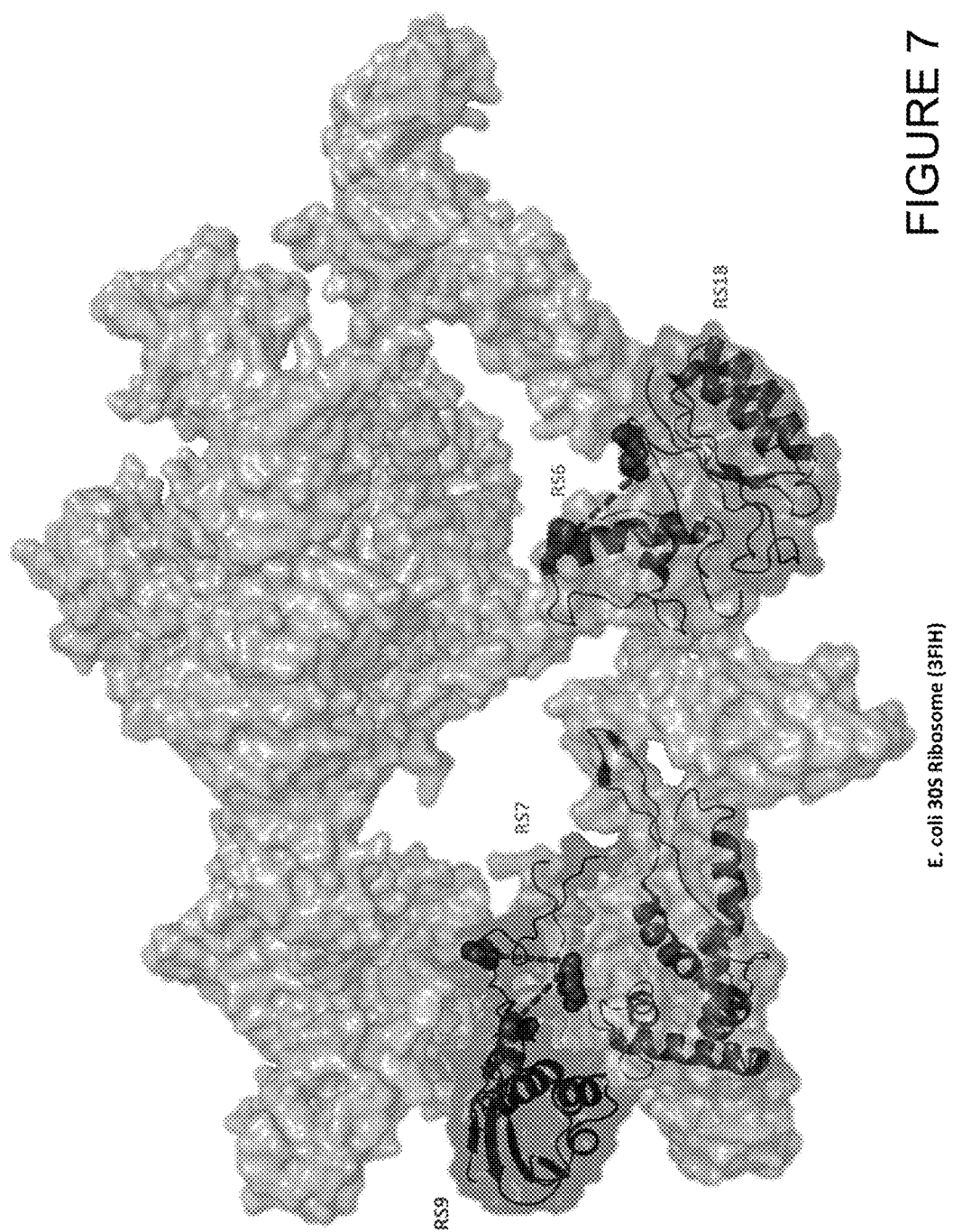
FIG. 7. *E. coli* 30 s ribosome (PDB: 3FIH) with 3 of 4 observed heterodimeric ribosomal cross-links mapped (RNA has been omitted).

The distributions of cross-linked peptide types observed were similar between *E. coli* and HeLa cells. More than 100 inter- and 100 intra-protein cross-linked peptides were identified with ReACT at less than 5% false discovery. However, many so-called "unambiguous homodimeric" cross-linked peptides where two identical sequences that could have only have originated from a cross-linked homodimer were observed. For unique proteins involved in cross-linked peptide relationships, the predicted cellular localization is shown in FIGS. 6B, 6E. Protein interaction networks for both *E. coli* and HeLa cells were constructed using ReACT data (FIGS. 6C, 6F). Proteins found in many cross-linked relationships are indicated as central nodes in these networks and are labeled with their Uniprot protein identifier. Connections between nodes are thick if the cross-link was identified at <5% FDR or thin if identified with the accurate mass and fragment ion method. Protein nodes are colored according to sub-cellular localization. These are the first interaction networks derived from cross-linked cell data.

Among the discovered inter-protein linkages, many of these proteins are known to co-localize, including 79 cross-linked peptide pairs identified from histone proteins for which co-crystal structure data are available. These histone protein data indicate that PIR molecules cross-link proteins within the cell nucleus. In fact, nuclear proteins represent the largest fraction of cross-linked proteins identified in this study, comprising 29% of the total (FIG. 6E). Many of the inter-protein linkages involve proteins known to co-localize which provides strong evidence that ReACT can yield new information on biologically-relevant interactions.

Figure 8:
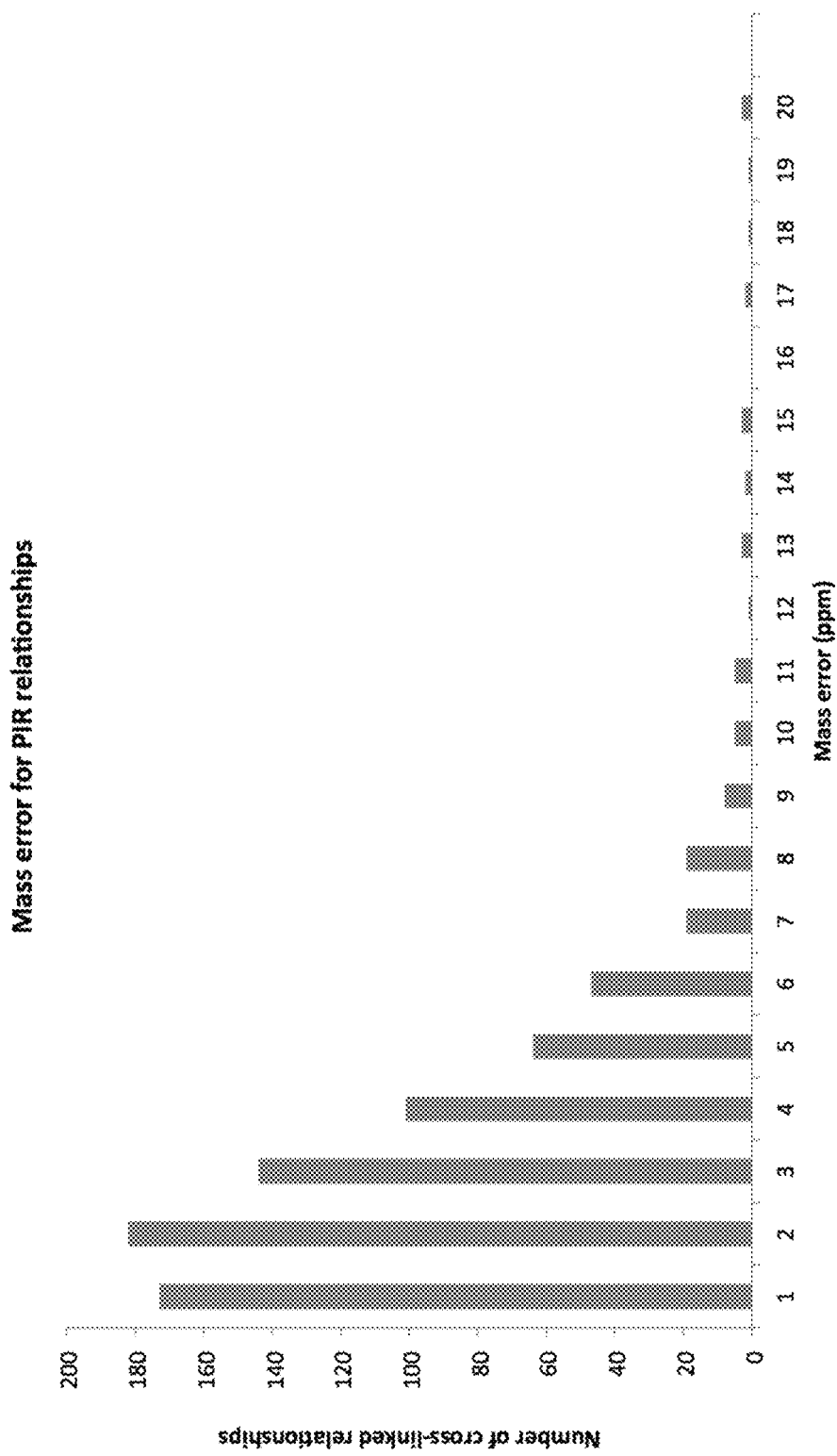
FIG. 8. Distribution of mass errors for 648 PIR relationships. Mass error is calculated as $10^{6}*|(\text{mass cross-linked precursor}-(\text{mass peptide 1}+\text{mass peptide 2}+\text{mass reporter}))|/\text{mass cross-linked precursor}$.

These investigations applied a two-stage approach. The first stage consists of enrichment and shotgun proteomics identification of PIR labeled proteins. In this stage, 15,415 unique peptides were identified at less than 1% FDR, corresponding to 3348 proteins that are putative reactive targets with the PIR cross-linker (data not shown; see Chavez et al., 2013, *Mol. Cell Proteomics* 12(5):1451-67). The second stage consisted of affinity enrichment of PIR labeled peptides allowing for the identification of the cross-linked site of interaction. A unique feature of PIR technology is that identification of each peptide in a cross-linked complex proceeds independently. Peptide mass determination and fragmentation spectral acquisition events and subsequent database searches allow each peptide to be identified independent of the other linked peptide. Furthermore, each identification event is also evaluated against a reverse sequence database so that every peptide sequence can be selected above a chosen FDR threshold. Application of these techniques to human cells resulted in 368 identified cross-linked peptide pairs at 5% FDR. The 5% FDR threshold refers to setting an E-value threshold on the peptide assignments from a SEQUEST search of the $MS^3$ spectra against the UniProt human database containing forward and reverse protein sequences such that 5% of the identified peptides passing the E-value threshold result from a match to a reverse sequence. (A table of these 368 cross-linked peptide pairs including observed peptide masses, peptide sequences, and protein descriptions, as well as annotated fragment ion spectra for each of the peptides in these 368 cross-linked peptide pairs, is shown in Chavez et al., 2013, *Mol. Cell Proteomics* 12(5):1451-67.) In addition to the 368 cross-linked peptide pairs for which both peptides were identified at 5% FDR, the data set presented here also included 532 additional cross-linked peptide pairs for which only one peptide was identified at less than 5% FDR but the second peptide was identified greater than 5% FDR. The peptides with less confident identifications (>5% FDR) were assigned to the top scoring peptide sequence identified from a SEQUEST search matching both in accurate precursor mass and greatest number of fragment ions. It is important to note that although high quality fragmentation information was not obtained for one of the released peptides from these cross-linked peptide pairs their masses were still measured with high mass accuracy and contain a BDP modified internal lysine residue. These data (not shown; see Chavez et al., 2013, *Mol. Cell Proteomics* 12(5):1451-67) highlight a persistent challenge for all cross-linking studies in that high quality fragment spectra are required for both peptides to yield confident cross-linked peptide pair identification. This is one area in particular where future improvements to mass spectrometry methods and informatics will help overcome the challenges faced with cross-linking experiments. Additionally improvements to cross-linker chemical design that would produce released peptides of primarily charge state 2+ and 3+, along with application of different digestion enzymes could contribute to overcoming challenges in this area. By combining these 532 cross-linked peptide pairs with higher confidence set of 368 cross-linked peptide pairs and filtering for redundancy yields a total of 783 unique cross-linked peptide pairs. The mean mass error for the PIR relationships for these 783 cross-linked peptide pairs was 2.9 ppm with over 84% (664) measured at less than 5 ppm mass error as can be seen in the histogram included in FIG. 8.

Figure 9A:
FIG. 9A: Protein interaction network generated exclusively from cross-linking results. Network consists of 307 nodes representing proteins connected by 446 edges representing observed intraprotein and interprotein cross-links. Nodes are shaded according to subcellular localization with major hubs indicated by larger node size. Bold black edges indicate cross-links for which both peptides were identified at less than 5% FDR whereas thin dashed edges are cross-links for which only one peptide passed the FDR threshold.

The data were further analyzed using a recently developed online software tool and database for cross-linking results named XLink-DB. XLink-DB automates several important analyses for large scale cross-linking data sets including generating an interaction network view, comparing observed interactions to known protein interaction databases, and mapping of cross-links onto known structural data. FIG. 9A illustrates a protein interaction network generated from the 648 unique cross-linked peptide pairs from human cells. The network consists of 307 nodes representing the identified cross-linked proteins connected by 446 edges representing observed intraprotein and interprotein cross-links. Highly connected hub nodes are highlighted with a larger node size and their UniProt identifier. Major hubs include histone proteins, ribosomal proteins, and heterogeneous ribonucleoproteins. Importantly, such a protein interaction network generated using chemical cross-linking contains a depth of information beyond what similar protein interaction networks generated by affinity pull-down methods contain. In addition to the identities of the interacting proteins, topological information about the interacting regions of these proteins is contained in the cross-linked residues. It is worth noting that for cross-linked peptides to be observed by the approach described in this paper must have existed in relatively close proximity and orientation to one another billions to trillions of times (assuming femtomole to picomole sensitivity levels for peptides using modern mass spectrometers) during the reactive lifetime of the cross-linker (λ~8 min in neutral pH aqueous buffer). Thus what could be viewed as limitations of current cross-linking technology actually provide a valuable benefit in that non-specific protein-protein interactions, which are a commonly an Achilles' heel for affinity purification-mass spectrometry (AP-MS) approaches, are likely to be less frequently detected because the linkage takes place on proteins within their native environment. Additionally, linkage of only two or a few specific lysine residues in two protein sequences indicates that the two proteins are close to one another in cells with a specific relative orientation so as to allow only specific cross-links to be formed. These two features: 1) high frequency of being close to one another and 2) high frequency of being close to one another with a specific orientation, are hallmarks of specific protein interactions. Therefore, chemical cross-linking technologies can provide this level of detail and will eventually be exploited more effectively to help better understand specific protein interactions in cells.

Figure 9B:
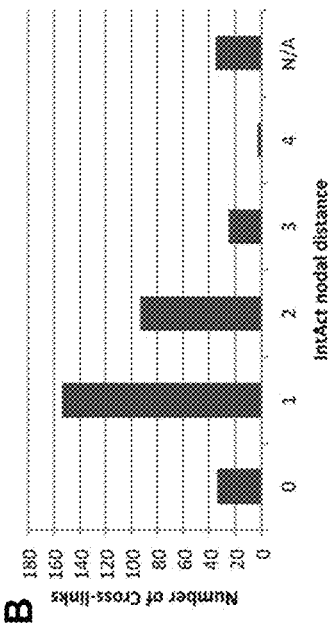
FIG. 9B: Distribution of nodal distance generated using xlink:DB to compare protein interactions from network in A with protein-protein interactions in the IntAct database.

The protein interaction network was processed with XLink-DB to compare the protein interactions discovered by cross-linking with previously known interactions present in the IntAct database (Kerrien et al., 2012, *Nucleic Acids Res.* 40:D841-46). A histogram of nodal distances between discovered and known interactions is displayed in FIG. 9B. The majority interprotein cross-links have a distance of either one or two, meaning that the two cross-linked proteins are not known to directly interact in the IntAct database but they either share a common interacting partner, which connects them, or their interacting partners are known to directly interact. Although there are only 34 cross-links that have an IntAct nodal distance of zero, it should be noted that there are several examples of well-known interacting proteins that do not exist as direct interacting partners in the IntAct database. For example the interaction between histones H31 (UniProt accession P68431) and H4 (UniProt accession P62805) are well established interacting partners in the nucleosome complex however have a nodal distance of one according to IntAct. Such cases are inevitable reflections of incomplete knowledge and annotations in protein interaction databases. Despite these instances, protein interactions with nodal distances of 1 or greater potentially represent newly discovered protein interactions. For example, the E3 ubiquitin-protein ligase CBL-B where lysine 468 was cross-linked with lysine 29 of the high mobility group protein B1. These two proteins have a nodal distance of one in IntAct, however are observed as direct interacting partners in this study. As described below, cross-links identify the endoplasmic reticulum membrane protein dolichyl-diphosphooligosaccharide-protein glycosyltransferase subunit 1 (aka ribophorin-1) and the outer membrane glycoprotein stabilin-1 as direct interacting partners although they are separated by two nodes in IntAct.

Figure 9C:
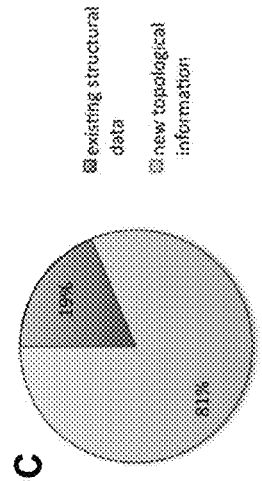
FIG. 9C: Pie chart indicating cross-links that can be mapped to existing structures in the PDB and those providing new topological information.
Figure 9D:
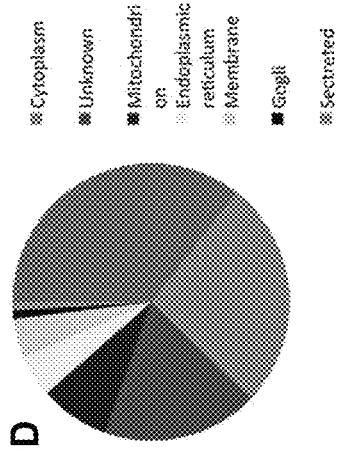
FIG. 9D: Pie chart indicating subcellular localization of cross-linked proteins.

Nodes in the network are shaded according to their top subcellular location obtained from the UniProt database. As expected for many of the nodes, interactions are discovered between proteins from the same subcellular compartment. However, there are also interactions between proteins from different subcellular compartments, which are readily explainable. For example interactions between nuclear and cytoplasmic proteins are to be expected, with many reports of proteins moving between these compartments through the nuclear pore 20 (Schwikowski et al., 2000, Nat. Biotechnol. 18:1257-61). It is also worth noting that the majority of proteins have multiple entries in UniProt for subcellular location so although the top entries for two cross-linked proteins may not match, subsequent entries may overlap. For example, the cross-link between alpha actinin 4, which has a top subcellular annotation as nuclear and a secondary annotation of cytoplasmic, and beta actin, which has a top subcellular annotation of cytoplasmic. In addition it is unreasonable to expect that the UniProt annotation for the subcellular localization of proteins is both complete and comprehensive, therefore it is quite possible that two proteins of seemingly different subcellular locations are identified as cross-linked. FIG. 9C illustrates the percentage of proteins from the various subcellular locations in a pie diagram. Importantly all major subcellular locations are represented and the large percentage of cytosolic and nuclear proteins indicates adequate penetration of the PIR cross-linker into cells, a conclusion supported by the fluorescence microscopy data in FIGS. 10A-10C.

By attempting to map the 691 unique cross-linked sites from 783 cross-linked peptides to available x-ray crystal structures in the Protein Data Bank, Euclidean distances between the linked alpha carbon atoms were obtained for 130 cross-links. The measured distances spanned a range from 5.1 to 54.3 Å with a median distance of 14.9 Å as can be seen in a histogram in supplemental Fig. S4. The distances on average are about 20 Å less than the maximum spacer arm length for BDP-PIR (~35 Å) with ~95% of the total measured distances less than 35 Å. The seven cases where measured distances exceeded 35 Å can be rationalized by considering factors such as the flexibility of protein structures in solution. For example the largest distance mapped (54.3 Å) corresponds to a cross-link between K37 of H3 and K91 of H4. Being that H3K37 is located on the very flexible N-terminal tail of H3 it is possible the actual distance between the cross-linked sites is shorter than that measured from the crystal structure. It is also possible that this cross-link results from the linkage between H3 and H4 from stacked nucleosome particles, rather than within a single nucleosome complex. As an example of another explainable case; the cross-link between K488 and K797 of DNA topoisomerase 2-alpha was mapped as an intraprotein cross-link with a distance of 42.2 Å, however it is possible this cross-link may span a shorter distance existing between two identical subunits of DNA topoisomerase 2-alpha being that it is known to form a homodimer (33). The PDB structure (1LWZ) used to map the distance of the cross-linked site for this protein only contains a monomeric structure so we were only able to map this distance as an intralink. The observed distances match well with other studies in our laboratory applying PIR cross-linking in *E. coli* (17-19). These distances also appear consistent with those observed and/or predicted in other studies that employed cross-linkers with much smaller linker arms such as DSS or BS3 (spacer arm length ~11.4 Å) (5, 11, 16, 34). For example Herzog et al. measured the median Euclidean distances between alpha carbons for 70 interprotein and 287 intraprotein DSS cross-linked peptide pairs from protein phosphatase 2A complexes to be 19.6 Å and 15.4 Å respectively (11). These measurements suggest that factors other than cross-linker length play a role in the determination of which sites are observed from large-scale cross-linking studies. The cross-links, which we were not able to map onto crystal structures, provide valuable new information on interaction topologies for many proteins that have no existing and/or partially resolved crystal structures. As can be seen by the pie chart in FIG. 8C no structural information exists in the Protein Data Bank for most (over 80%) of the total cross-linked sites from both the high and low confidence data sets identified in this study. For example cross-links observed in the highly disordered N-terminal tails of the core histone proteins, which are absent from nucleosome crystal structures. Additionally cross-links membrane proteins prohibitin 1 (PHB) and prohibitin-2 (PHB2) can provide new insights into the topology of interaction for these proteins. These and other examples are discussed in more detail below.

Of the 368 high confidence cross-linked pairs, 284 consisted of two peptides from within the same protein sequence, meaning they are either intraprotein linkages or interprotein linkages from homo-multimers. These two types are not easily distinguished except for cases where the two peptides are exactly the same sequence (peptide homodimer) or share some overlapping sequence, which only occurs once per protein molecule. There are 12 such unambiguous homodimers in the present data set.

The high number of observed intraprotein and homodimer cross-links is to be expected for several reasons. First, intraprotein cross-links are formed in greater abundance because of the fact that once one reactive group of the cross-linker reacts with a protein molecule the second functional group becomes tethered and is constrained to react with a free amine site nearby, often times within the same molecule. Furthermore, self-interacting proteins are anticipated to be a predominant type of specific protein-protein interaction because of colocalization and a relatively high local concentration of binding partners (Ispolatov et al., 2005, *Nucleic Acids Res.* 33:3629-35; Kuriyan et al., 2007, *Nature* 450:983-90). Select examples of unambiguous homodimer cross-links are discussed in more detail below.

In addition to enabling identification of traditional cross-linked peptides, the data presented in this Example also demonstrate the ability to identify cross-linked peptides containing additional post-translational modifications including methylation, and dimethylation on lysine and arginine, trimethylation lysine, and acetylation on lysine. It has been previously noted that cross-linked sites observed in *E. coli* were also sites of lysine acetylation (Bruce, 2012, *Proteomics* 12:1565-75). This raises interesting questions about the relative reactivity of these particular lysine residues as well as the influence of these and nearby lysine sites in defining protein topology and regulation of protein interactions. It seems plausible that lysine residues, which are targets of post-translational modification, reside on the surface of the protein to increase accessibility. These specific residues also appear to represent local "hot spots" of reactivity for modifying enzymes as well as cross-linker molecules. The application of chemical cross-linking to understand the impact of post-translational modifications on protein topology and interactions is currently uncharted territory, but could greatly accelerate understanding of the relevance of post-translational modifications in biological systems. A primary factor that has inhibited this advance is the large increase in database search space when allowing for the possibility of post-translational modifications that is further exacerbated by the $N^2$ increase in search space encountered when attempting to assign two peptide sequences from a single precursor mass (Maiolica et al., 2007, *Mol. Cell. Proteomics* 6:2200-11). Therefore, confident identification of variable post-translational modifications from complex samples becomes impractical, if not intractable, when working with traditional, non-cleavable cross-linkers. The cleavable feature of PIR cross-linkers allows for individual accurate mass measurements to be made on the released peptides, eliminating the $N^2$ increase in search space, and allowing for the confident identification of variable post-translational modifications. The possibility of identifying post-translational modifications in the cross-linked peptide data set from HeLa cells was investigated. Excitingly, confident identification was achieved on 93 unique cross-linked peptide pairs, which contained additional post-translational modifications including mono-, di-, and tri-methylation on Lys as well as acetylation on Lys residues (data not shown; see Chavez et al., 2013, *Mol. Cell Proteomics* 12(5):1451-67). These 93 cross-linked peptides contain 21 unique sites of modification on 13 different proteins. Importantly, these data are the first reported cross-linked peptides containing in vivo post-translational modifications known to be important for regulating protein topology and interactions and having a direct impact on protein function. To date, identification of modified cross-linked peptides from genome scale databases has not been demonstrated by any other approach.

Eighty-two cross-linked peptide pairs were identified from histones, which also contained additional post-translational modifications. All of the observed histone cross-linked sites and modifications observed are included in Table 1.

TABLE 1

Histone cross-links with modifications.

| peptide 1* (SEQ ID NO) | peptide 2* (SEQ ID NO) | Prot. 1 (UniProt) | Prot. 2 (UniProt) | peptide 1 mod. verification‡ | peptide 2 mod. verification‡ | pep1 xlink site^ | pep2 xlink site^ |
|---|---|---|---|---|---|---|---|
| K[142.11]STGG K[325.13]APR (18) | TK[325.13]QTA R (28) | sp P68431 H31_HUMAN +3 | sp P68431 H31_HUMAN +3 | H3K9me, Uniprot | | 14 | 4 |
| K[156.13]STGG K[325.130APR (18) | TK[325.13]QTA R (28) | sp P68431 H31_HUMAN +3 | sp P68431 H31_HUMAN +3 | H3K9me2, Uniprot | | 14 | 4 |
| K[142.11]STGG K[325.13]APR (18) | K[325.13]QLAT K (19) | sp P68431 H31_HUMAN +3 | sp P68431 H31_HUMAN +3 | H3K9me, Uniprot | | 14 | 18 |
| K[156.13]STGG K[325.13]APR (18) | K[325.13]QLAT K (19) | sp P68431 H31_HUMAN +3 | sp P68431 H31_HUMAN +3 | H3K9me2, Uniprot | | 14 | 18 |
| K[156.13]STGG K[325.13]APR (18) | K[325.13]QLAT K[170.110AAR (29) | sp P68431 H31_HUMAN +3 | sp P68431 H31_HUMAN +2 | H3K9me2, Uniprot | H3K23ac, Uniprot | 14 | 18 |
| K[156.13]SAPA TGGVK[325.13] KPHR (30) | YQK[325.13]ST ELLIR (31) | sp P68431 H31_HUMAN +2 | sp P68431 H31_HUMAN +3 | H3K27me2, Uniprot | | 36 | 56 |
| K[156.13]SAPA TGGVK[156.13] K[325.13]PHR (30) | YQK[325.13]ST ELLIR (31) | sp P68431 H31_HUMAN +2 | sp P68431 H31_HUMAN +3 | H3K27me2, H3K36me2, Uniprot | | 37 | 56 |
| K[156.13]SAPA TGGVK[325.13] KPHR (30) | K[325.13]QLAT K (19) | sp P68431 H31_HUMAN +2 | sp P68431 H31_HUMAN +3 | H3K27me2, Uniprot | | 36 | 18 |
| K[142.11]STGG K[325.13]APR (18) | K[325.13]QLAT K[170.11]AAR (29) | sp P68431 H31_HUMAN +3 | sp P68431 H31_HUMAN +2 | H3K9me2, Uniprot | H3K23ac, Uniprot | 14 | 18 |
| K[156.13]SAPA TGGVK[142.11] K[325.13]PHR (30) | YQK[325.13]ST ELLIR (31) | sp P68431 H31_HUMAN +2 | sp P68431 H31_HUMAN +3 | H3K27me2, H3K36me, Uniprot | | 37 | 56 |

TABLE 1-continued

Histone cross-links with modifications.

| peptide 1* (SEQ ID NO) | peptide 2* (SEQ ID NO) | Prot. 1 (UniProt) | Prot. 2 (UniProt) | peptide 1 mod. verification‡ | peptide 2 mod. verification‡ | pep1 xlink site^ | pep2 xlink site^ |
|---|---|---|---|---|---|---|---|
| K[156.13]SAPATGGVK[325.13]K[142.11]PHR (30) | YQK[325.13]STELLIR (31) | sp P68431 H31_HUMAN +2 | sp P68431 H31_HUMAN +3 | H3K27me2, H3K36me, Uniprot | | 36 | 56 |
| K[156.13]SAPATGGVK[325.13]KPHR (30) | K[325.13]QLATK[170.11]AAR (29) | sp P68431 H31_HUMAN +2 | sp P68431 H31_HUMAN +2 | H3K27me2, Uniprot | H3K23ac, Uniprot | 36 | 18 |
| K[156.13]STGGK[325.13]APR (18) | YQK[325.13]STELLIR (31) | sp P68431 H31_HUMAN +3 | sp P68431 H31_HUMAN +3 | H3K9me2, Uniprot | | 14 | 56 |
| K[156.13]SAPATGGVK[325.13]KPHR (30) | TK[325.13]QTAr (33) | sp P68431 H31_HUMAN +2 | sp P68431 H31_HUMAN +3 | H3K27me2, Uniprot | | 36 | 4 |
| K[156.13]STGGK[325.13]APR (18) | RGGVK[325.13]R (34) | sp P68431 H31_HUMAN +3 | sp P62805 H4_HUMAN | H3K9me2, Uniprot | | 14 | 44 |
| K[156.13]SAPATGGVK[156.13]K[325.13]PHR (30) | TK[325.13]QTAR (33) | sp P68431 H31_HUMAN +2 | sp P68431 H31_HUMAN +3 | H3K27me2, H3K36me2, Uniprot | | 37 | 4 |
| K[156.13]SAPATGGVK[325.13]K[156.13]PHR (30) | K[325.13]QLATK (19) | sp P68431 H31_HUMAN +2 | sp P68431 H31_HUMAN +3 | H3K27me2, H3K37me2, Uniprot | | 36 | 18 |
| K[156.13]SAPATGGVK[142.11]K[325.13]PHR (30) | K[325.13]QLATK[170.11]AAR (29) | sp P68431 H31_HUMAN +2 | sp P68431 H31_HUMAN +2 | H3K27me2, H3K36me, Uniprot | H3K23ac, Uniprot | 37 | 18 |
| K[156.13]SAPATGGVK[156.13]K[325.13]PHR (30) | K[325.13]QLATK[170.11]AAR (29) | sp P68431 H31_HUMAN +2 | sp P68431 H31_HUMAN +2 | H3K27me2, H3K36me2, Uniprot | H3K23ac, Uniprot | 37 | 18 |
| K[156.13]SAPATGGVK[325.13]K[156.13]PHR (30) | YQK[325.13]STELLIR (31) | sp P68431 H31_HUMAN +2 | sp P68431 H31_HUMAN +3 | H3K27me2, H3K37me2, Uniprot | | 36 | 56 |
| K[156.13]SAPATGGVK[325.13]KPHR (30) | K[325.13]TESHK (35) | sp P68431 H31_HUMAN +2 | sp P04908 H2A1B_HUMAN +1 | H3K27me2, Uniprot | | 36 | 119 |
| K[156.13]SAPATGGVK[156.13]K[325.13]PHR (30) | K[325.13]TESHK (35) | sp P68431 H31_HUMAN +2 | sp P04908 H2A1B_HUMAN +1 | H3K27me2, H3K36me2, Uniprot | | 37 | 119 |
| K[156.13]SAPATGGVK[142.11]K[325.13]PHR (30) | K[325.13]TESHK (35) | sp P68431 H31_HUMAN +2 | sp P04908 H2A1B_HUMAN +1 | H3K27me2, H3K36me, Uniprot | | 37 | 119 |
| K[156.13]SAPATGGVK[325.13]KPHR (30) | K[156.13]STGGK[325.13]APR (18) | sp P68431 H31_HUMAN +2 | sp P68431 H31_HUMAN +3 | Uniprot | H3K9me2, Uniprot | 36 | 14 |
| K[142.11]STGGK[325.13]APR (18) | K[170.14]SAPATGGVK[325.13]KPHR (30) | sp P68431 H31_HUMAN +3 | sp P68431 H31_HUMAN +2 | H3K9me, Uniprot | H3K27me3, Uniprot | 14 | 36 |
| K[142.11]STGGK[325.13]APR (18) | K[156.13]SAPATGGVK[325.13]KPHR (30) | sp P68431 H31_HUMAN +3 | sp P68431 H31_HUMAN +2 | H3K9me, Uniprot | H3K27me2, Uniprot | 14 | 36 |

TABLE 1-continued

Histone cross-links with modifications.

| peptide 1* (SEQ ID NO) | peptide 2* (SEQ ID NO) | Prot. 1 (UniProt) | Prot. 2 (UniProt) | peptide 1 mod. veri- fication‡ | peptide 2 mod. veri- fication‡ | pep1 xlink site^ | pep2 xlink site^ |
|---|---|---|---|---|---|---|---|
| K[156.13]SAPA TGGVK[142.11] K[325.13]PHR (30) | K[156.13]STGG K[325.13]APR (18) | sp P68431 H31_HUMAN +2 | sp P68431 H31_HUMAN +3 | H3K27me2, H3K36me, Uniprot | H3K9me2, Uniprot | 37 | 14 |
| K[156.13]SAPA TGGVK[156.13] K[325.13]PHR (30) | K[156.13]STGG K[325.13]APR (18) | sp P68431 H31_HUMAN +2 | sp P68431 H31_HUMAN +3 | H3K27me2, H3K36me2, Uniprot | H3K9me2, Uniprot | 37 | 14 |
| K[156.13]SAPA TGGVK[156.13] K[325.13]PHR (30) | K[170.14]STGG K[325.13]APR (18) | sp P68431 H31_HUMAN +2 | sp P68431 H31_HUMAN +3 | H3K27me2, H3K36me2, Uniprot | H3K9me3, Uniprot | 37 | 14 |
| K[156.13]SAPA TGGVK[156.13] K[325.13]PHR (30) | RGGVK[325.13] R (34) | sp P68431 H31_HUMAN +2 | sp P62805 H4_HUMAN | H3K27me2, H3K36me2, Uniprot | | 37 | 44 |
| K[156.13]SAPA TGGVK[156.13] K[325.13]PHR (30) | LAHYNK[325.13] R (36) | sp P68431 H31_HUMAN +2 | sp P33778 H2B1B_ HUMAN +2 | H3K27me2, H3K36me2, Uniprot | | 37 | 85 |
| K[156.13]SAPA TGGVK[325.13] K[156.13]PHR (30) | TK[325.13]QTA R (19) | sp P68431 H31_HUMAN +2 | sp P68431 H31_HUMAN +3 | H3K27me2, H3K37me2, Uniprot | | 36 | 4 |
| K[156.13]SAPA TGGVK[156.13] K[325.13]PHR (30) | K[325.13]QLAT K (19) | sp P68431 H31_HUMAN +2 | sp P68431 H31_HUMAN +3 | H3K27me2, H3K36me2, Uniprot | | 37 | 18 |
| K[156.13]SAPA TGGVK[325.13] KPHR (30) | K[325.13]STGG K (37) | sp P68431 H31_HUMAN +2 | sp P68431 H31_HUMAN +3 | H3K27me2, Uniprot | | 36 | 9 |
| K[142.11]SAPA TGGVK[325.13] KPHR (30) | K[156.13]STGG K[325.13]APR (18) | sp P68431 H31_HUMAN +2 | sp P68431 H31_HUMAN +3 | H3K27me, Uniprot | | 36 | 14 |
| K[156.13]SAPA TGGVK[325.13] KPHR (30) | RGGVK[325.13] R (34) | sp P68431 H31_HUMAN +2 | sp P62805 H4_HUMAN | H3K27me2, Uniprot | | 36 | 44 |
| K[156.13]SAPA TGGVK[142.11] K[325.13]PHR (30) | RGGVK[325.13] R (34) | sp P68431 H31_HUMAN +2 | sp P62805 H4_HUMAN | H3K27me2, H3K36me, Uniprot | | 37 | 44 |
| K[156.13]SAPA TGGVK[325.13] K[142.11]PHR (30) | RGGVK[325.13] R (34) | sp P68431 H31_HUMAN +2 | sp P62805 H4_HUMAN | H3K27me2, H3K36me, Uniprot | | 36 | 44 |
| K[156.13]STGG K[325.23]APR (18) | K[156.13]STGG K[325.13]APR (18) | sp P68431 H31_HUMAN +3 | sp P68431 H31_HUMAN +3 | H3K9me2, Uniprot | H3K9me2, Uniprot | 14 | 14 |
| K[156.13]SAPA TGGVK[142.11] K[325.13]PHR (30) | TK[325.13]QTA R (33) | sp P68431 H31_HUMAN +2 | sp P68431 H31_HUMAN +3 | H3K27me2, H3K36me, Uniprot | | 37 | 4 |
| K[156.13]SAPA TGGVK[142.11] K[325.13]PHR (30) | K[325.13]QLAT L (19) | sp P68431 H31_HUMAN +2 | sp P68431 H31_HUMAN +3 | H3K27me2, H3K36me, Uniprot | | 37 | 18 |

TABLE 1-continued

Histone cross-links with modifications.

| peptide 1* (SEQ ID NO) | peptide 2* (SEQ ID NO) | Prot. 1 (UniProt) | Prot. 2 (UniProt) | peptide 1 mod. verification‡ | peptide 2 mod. verification‡ | pep1 xlink site^ | pep2 xlink site^ |
|---|---|---|---|---|---|---|---|
| K[156.13]SAPS TGGVK[156.13] K[325.13]PHR (32) | YQK[325.13]ST ELLIR (31) | sp P84243 H33_HUMAN +3 | sp P84243 H33_HUMAN +3 | H3K27me2, H3K36me2, Uniprot | | 37 | 56 |
| K[325.13]STGG K[170.11]APR (18) | TK[325.13]QTA R (28) | sp P68431 H31_HUMAN +3 | sp P68431 H31_HUMAN +3 | H3K14ac, Uniprot | | 9 | 4 |
| K[325.13]QLAT K[170.11]AAR (29) | TK[325.13]QTA R (28) | sp P68431 H31_HUMAN +2 | sp P68431 H31_HUMAN +3 | H3K14ac, Uniprot | | 18 | 4 |
| K[170.14]STGG K[325.13]APR (18) | TK[325.13]QTA R (28) | sp P68431 H31_HUMAN +3 | sp P68431 H31_HUMAN +3 | H3K9me3, Uniprot | | 14 | 4 |
| K[170.14]STGG K[325.13]APR (18) | K[325.13]QLAT K (19) | sp P68431 H31_HUMAN +3 | sp P68431 H31_HUMAN +3 | H3K9me3, Uniprot | | 14 | 18 |
| K[170.14]SAPA TGGVKK[325.13] PHR (30) | YQK[325.13]ST ELLIR (31) | sp P68431 H31_HUMAN +3 | sp P68431 H31_HUMAN +3 | H3K27me3, Uniprot | | 37 | 56 |
| GLGK[325.13]G GAK[170.11]R (38) | LLLPGELAK [325.13]HAVSE GTK (39) | sp P62805 H4_HUMAN | sp P62807 H2B1C_ HUMAN +3 | H4K16ac, Uniprot | | 12 | 108 |
| K[170.14]STGG K[325.13]APR (18) | K[325.13]QLAT K[170.11]AAR (29) | sp P68431 H31_HUMAN +3 | sp P68431 H31_HUMAN +2 | H3K9me3, Uniprot | H3K23ac, Uniprot | 14 | 18 |
| K[170.11]SAPA TGGVK[325.13] KPHR (30) | YQK[325.13]ST ELLIR (31) | sp P68431 H31_HUMAN +2 | sp P68431 H31_HUMAN +3 | H3K27ac, Uniprot | | 36 | 56 |
| K[170.14]SAPA TGGVK[325.13] KPHR (30) | YQK[325.13]ST ELLIR (31) | sp P68431 H31_HUMAN +2 | sp P68431 H31_HUMAN +3 | H3K27me3, Uniprot | | 36 | 56 |
| K[170.14]SAPA TGGVK[325.13] KPHR (30) | K[325.13]QLAT K (19) | sp P68431 H31_HUMAN +2 | sp P68431 H31_HUMAN +3 | H3K27me3, Uniprot | | 36 | 18 |
| K[325.13]QLAT K[170.11]AAR (29) | K[325.13]STGG K[170.11]APR | sp P68431 H31_HUMAN +2 | sp P68431 H31_HUMAN +3 | H3K14ac, Uniprot | H3K14ac, Uniprot | 18 | 9 |
| K[170.14]SAPA TGGVK[325.13] KPHR (30) | TK[325.13]QTA R (28) | sp P68431 H31_HUMAN +2 | sp P68431 H31_HUMAN +3 | H3K27me3, Uniprot | | 36 | 4 |
| K[170.14]SAPA TGGVK[325.13] KPHR (30) | K[325.13]QLAT K[170.11]AAR (29) | sp P68431 H31_HUMAN +2 | sp P68431 H31_HUMAN +2 | H3K27me3, Uniprot | H3K23ac, Uniprot | 36 | 18 |
| K[325.13]QLAT K[170.11]AAR (29) | K[325.13]SAPA TGGVK[142.11] KPHR (30) | sp P68431 H31_HUMAN +2 | sp P68431 H31_HUMAN +2 | H3K14ac, Uniprot | H3K36me, Uniprot | 18 | 27 |
| K[170.14]SAPA TGGVK[325.13] KPHR (30) | K[325.13]TESH HK (40) | sp P68431 H31_HUMAN +2 | sp P04908 H2A1B_ HUMAN +1 | H3K27me3, Uniprot | | 36 | 119 |
| K[170.14]SAPA TGGVK[325.13] KPHR (30) | K[170.14]STGG K[325.13]APR (18) | sp P68431 H31_HUMAN +2 | sp P68431 H31_HUMAN +3 | H3K27me3, Uniprot | H3K9me3, Uniprot | 36 | 14 |
| K[170.11]SAPA TGGVKK[325.13] PHR (30) | K[325.13]QLAT K (19) | sp P68431 H31_HUMAN +2 | sp P68431 H31_HUMAN +3 | H3K27ac, Uniprot | | 37 | 18 |

TABLE 1-continued

Histone cross-links with modifications.

| peptide 1* (SEQ ID NO) | peptide 2* (SEQ ID NO) | Prot. 1 (UniProt) | Prot. 2 (UniProt) | peptide 1 mod. verification‡ | peptide 2 mod. verification‡ | pep1 xlink site^ | pep2 xlink site^ |
|---|---|---|---|---|---|---|---|
| K[325.13]QLATK[170.11]AAR (29) | K[325.13]SAPATGGVK[156.13]KPHR (30) | sp P68431 H31_HUMAN +2 | sp P68431 H31_HUMAN +2 | H3K14ac, Uniprot | H3K36me2, Uniprot | 18 | 27 |
| KQLATK[325.13]AAR (29) | K[156.13]SAPATGGVK[325.13]KPHR (30) | sp P68431 H31_HUMAN +2 | sp P68431 H31_HUMAN +2 | | H3K27me2, Uniprot | 23 | 36 |
| KQLATK[325.13]AAR (29) | K[142.11]STGGK[325.13]APR (18) | sp P68431 H31_HUMAN +2 | sp P68431 H31_HUMAN +3 | | H3K9me, Uniprot | 23 | 14 |
| KQLATK[325.13]AAR (29) | K[156.13]STGGK[325.13]APR (18) | sp P68431 H31_HUMAN +2 | sp P68431 H31_HUMAN +3 | | H3K9me2, Uniprot | 23 | 14 |
| GGK[325.13]GLGK (41) | K[156.13]STGGK[325.13]APR (18) | sp P62805 H4_HUMAN | sp P68431 H31_HUMAN +3 | | H3K9me2, Uniprot | 8 | 14 |
| KTESHHK[325.13]AK (42) | K[156.13]STGGK[325.13]APR (18) | sp P04908 H2A1B_HUMAN | sp P68431 H31_HUMAN +3 | | H3K9me2, Uniprot | 125 | 14 |
| GK[325.13]GGK (43) | K[156.13]SAPATGGVK[325.13]KPHR (30) | sp P68431 H31_HUMAN +2 | sp P68431 H31_HUMAN +2 | | H3K27me2, Uniprot | 5 | 36 |
| KQLATK[325.13]AAR (29) | K[142.11]SAPATGGVK[325.13]KPHR (30) | sp P68431 H31_HUMAN +2 | sp P68431 H31_HUMAN +2 | | H3K27me, Uniprot | 23 | 36 |
| KQLATK[325.13]AAR (29) | K[325.13]SAPATGGVK[142.11]KPHR (30) | sp P68431 H31_HUMAN +2 | sp P68431 H31_HUMAN +2 | | H3K36me, Uniprot | 23 | 27 |
| KQLATK[325.13]AAR (29) | K[156.13]SAPATGGVK[156.13]K[325.13]PHR (30) | sp P68431 H31_HUMAN +2 | sp P68431 H31_HUMAN +2 | | H3K27me2, H3K36me2, Uniprot | 23 | 37 |
| KQLATK[325.13]AAR (29) | K[156.13]SAPATGGVK[142.11]K[325.13]PHR (30) | sp P68431 H31_HUMAN +2 | sp P68431 H31_HUMAN +2 | | H3K27me2, H3K36me, Uniprot | 23 | 37 |
| KQLATK[325.13]AAR (29) | K[156.13]SAPATGGVK[325.13]K[142.11]PHR (30) | sp P68431 H31_HUMAN +2 | sp P68431 H31_HUMAN +2 | | H3K27me2, H3K37me, Uniprot | 23 | 36 |
| KTESHHK[325.13]AK (42) | K[156.13]SAPATGGVK[325.13]KPHR (30) | sp P04908 H2A1B_HUMAN | sp P68431 H31_HUMAN +2 | | H3K27me2, Uniprot | 125 | 36 |
| KQLATK[325.13]AAR (29) | K[156.13]SAPATGGVK[325.13]K[156.13] (30) | sp P68431 H31_HUMAN +2 | sp P68431 H31_HUMAN +2 | | H3K27me2, H3K37me2, Uniprot | 23 | 36 |
| GK[325.13]GGK (43) | GLGK[325.13]GGAK[170.11]R (38) | sp P68431 H31_HUMAN +2 | sp P62805 H4_HUMAN | | H4K16ac, Uniprot | 5 | 12 |
| KQLATK[325.13]AAR (29) | K[170.14]STGGK[325.13]APR (18) | sp P68431 H31_HUMAN +2 | sp P68431 H31_HUMAN +3 | | H3K9me3, Uniprot | 23 | 14 |
| KQLATK[325.13]AAR (29) | K[325.13]STGGK[170.11]APR (18) | sp P68431 H31_HUMAN +2 | sp P68431 H31_HUMAN +3 | | H3K14ac, Uniprot | 23 | 9 |

TABLE 1-continued

Histone cross-links with modifications.

| peptide 1* (SEQ ID NO) | peptide 2* (SEQ ID NO) | Prot. 1 (UniProt) | Prot. 2 (UniProt) | peptide 1 mod. verification‡ | peptide 2 mod. verification‡ | pep1 xlink site^ | pep2 xlink site^ |
|---|---|---|---|---|---|---|---|
| K[325.13]QLAT K (19) | K[325.13]STGG K[170.11]APR (18) | sp P68431 H31_HUMAN +3 | sp P68431 H31_HUMAN +3 | | H3K14ac, Uniprot | 18 | 9 |
| KQLATK[325.13] AAR (29) | K[325.13]SAPA TGGCK[170.14] KPHR (30) | sp P68431 H31_HUMAN +2 | sp P68431 H31_HUMAN +2 | | H3K36me3, Uniprot | 23 | 27 |
| KQLATL[325.13] AAR (29) | K[325.13]SAPS TGGVK[170.14] KPHR (32) | sp P68431 H31_HUMAN +2 | sp P84243 H33_HUMAN +2 | | H3K36me3, Uniprot | 23 | 27 |
| KQLATK[325.13] AAR (29) | K[170.14]SAPA TGGVK[325.13] KPHR (30) | sp P68431 H31_HUMAN +2 | sp P68431 H31_HUMAN +2 | | H3K27me3, Uniprot | 23 | 36 |
| KTESHHK [325.13]AK (42) | K[170.14]STGG K[325.13]APR | sp P04908 H2A1B_ HUMAN | sp P68431 H31_HUMAN +3 | | H3K9me3, Uniprot | 125 | 14 |

*identified cross-linked peptide sequence with mass of modifications indicated in brackets following the modified residue. Modifications are: 142.11-mono-methylation, 156.13-di-methylation, 170.11-acetylation, 170.14-tri-methylation, 325.13-BDP stump mass indicating cross-linked residue.
‡Modification checked against data contained in UniProt for known modification sites.
^amino acid residue number for cross-linked site starting with initial Met = 1.

These data, discussed in further detail below, provide unique insight into the structure of histone proteins and how their topology changes with various modification states. It is important to note that the lysine side chains linked by our cross-linker must be unmodified because the activated ester reactive groups will not react with acetylated or methylated amines. Furthermore, it is worth noting that six peptides were assigned to have modified Lys or Arg residues as their C-terminal residue. Although there are reports of trypsin cleaving at methylated Lys, there is a possibility these represent incorrect assignments because of the lack of specificity of trypsin to cleave at modified Lys or Arg. However six peptides out of 736 total peptides in the high-confidence set of cross-links corresponds to ~0.8% of peptide identifications, well below the 5% FDR threshold.

Unambiguous Cross-Linked Homodimers.

If one accepts the theory that protein colocalization lies at the origin of all protein-protein interactions and that most interactions between paralogs evolved from ancestral homodimer interactions, then understanding topologies of interaction between homodimers is at the heart of understanding how and why protein molecules interact with one another. Because of their importance, homo-oligomeric interactions are of intense interest for drug development effort for the treatment of a myriad of human diseases including cancer and HIV. HSP90 is one such homodimer that has significant clinical significance in cancer. One example of an unambiguous homodimer cross-link is the peptide FYEAFSK434NLK spanning residues 428-437 (bold underline indicates cross-linked residue) from heat shock protein 90-beta (HS90B). The mass spectra identifying the HS90B homodimer cross-link are shown in FIGS. 11A-11C. HSP90 proteins are highly conserved, essential molecular chaperones that assist in the proper folding and stabilization of proteins as well as regulation of cellular signaling pathways. The location of the homodimer cross-link was mapped onto the homologous structure for HS90 homodimer from yeast. The identified cross-linked site lies near the transition between the catalytic protein binding domain of HS90 that serves to bind substrates and contains the catalytic loop, and the C-terminal dimerization domain FIG. 11D. Prediction of protein disorder with the VSL2 disorder predictor using the sequence from HS90B indicates that K434 is located near a transition from ordered to disordered structure, which appear to be more susceptible to cross-linker reaction in large scale studies. Five additional cross-links were observed in HS90B including two with K434 (K434-K606, and K346-K434) linking this site with sites in the C-terminal dimerization domain and in the disordered amphiphilic loop implicated in client protein interactions respectively. Of the three additional HS90B cross-links, two are in the N-terminal region (K52-K106, K198-K203) and one is in the C-terminal region K606-K623. Although these additional cross-links do not provide unambiguous information about the multimeric state of HS90B, they are nonetheless structurally informative. Recently HSP90 proteins have become the target of anti-cancer treatments because of their stabilization of several oncogenic factors promoting tumor growth. Two cytosolic isoforms of HSP90 exist in humans, including HS90B (constitutive expression form) and heat shock protein 90-alpha (HS90A) (inducible expression form). These two isoforms share 85% sequence homology and are thought to be the result of a gene duplication event that occurred 500 million years ago. The two isoforms of HSP90 are thought to exist primarily as homodimers however some evidence for alpha-beta homodimers also exists. Interestingly, a hetero-dimer cross-linked peptide pair was identified that included the same site of HS90B (K434), and the peptide FYEQFSK$^{442}$NIK (SEQ ID NO: 1) spanning residues 436-445 of HS90A. The respective mass spectra used to identify this hetero-dimer cross-linked peptide pair are illustrated in FIG. 12. Sequence alignment of HS90A and HS90B from human and HS90 from yeast (not shown) reveals that all of the lysine residues cross-linked in HS90B are conserved in HS90A and in yeast HS90 except for K204 in yeast and K347 in HS90A, which are both substituted to arginine. As mentioned above the cross-linked residues identified here (HS90B-K434, and HS90A-K442) lie near the interface of the C-terminal dimerization domain and the middle domain of HSP90, which is important for client protein binding and also contains the catalytic loop. Interestingly, both K434 and K623 of HS90B, and K442 of HS90A have been identified as acetylation sites. Acetylation has been shown to regulate HS90 activity and can inhibit its dynamic association with other chaperones and cochaperones. Several studies have correlated HSP90 activity with histone deacetylase (HDAC) activity, suggesting that combination cancer therapy with HSP90 inhibitors and HDAC inhibitors may have a synergistic effect. Although acetylation of these particular lysine residues has not yet been detected in cross-linked peptide relationships, the fact that these sites of acetylation are known to be important for stabilization of protein interactions demonstrates that in vivo cross-linking methods can, in some cases, be used to identify interactions topologies in these same critical regions. The relationships between sites of post-translational modifications that were identified in cross-linked peptides from other proteins are discussed in more detail below.

Another example of a cross-linked homodimer is the mitochondrial enzyme glutamate dehydrogenase (GDH). GDH exists as a homo-hexamer and catalyzes the conversion of glutamate into α-ketoglutarate and ammonia. PIR data allowed identification of the peptide FGK$^{479}$HGGTIPIVPTAEFQDR (SEQ ID NO: 44) as an unambiguous cross-linked homodimer. In a similar situation to the cases discussed above, the cross-linked lysine residue (K479) is also known to be a site of acetylation. GDH has been identified as an in vivo target of the sirtuin SIRT3, although the functional significance of GDH acetylation remains unclear. The cross-linked site exists near a tri-molecular interface at the tip of the antenna domain FIG. 13. The antenna domain is not found in bacterial, plant or fungal GDH and is thought to play an important role in allosteric regulation of GDH.

Extensive Cross-Linking of Histones.

From the high confidence set of 368 cross-linked pairs, 162 (44%) were intra- or interprotein links between histone proteins. Histones are the chief protein components of chromatin, forming a bead like nucleosome core complex around which DNA is coiled. There are five major classes of histones including the core histones H2A, H2B, H3, and H4, and the linker histones H1/H5. Experiments reported here resulted in identification of cross-links in and between each of these classes of histones. A nucleosome particle is comprised of an octameric complex containing two copies of each of the four core histone proteins around which 147 base pairs of DNA is wrapped. The structure of the core histones is highly conserved consisting of a helix-turn-helix-turn-helix motif from which long tails extend. The histone tails are highly disordered in structure and enriched in Lys and Arg residues making them particularly basic. The tails play a particularly important role in epigenetic regulation of chromatin serving as a scaffold for a host of post-translational modifications including methylation, acetylation, phosphorylation, and others. It has been suggested that combinations of these modifications may alter histone topology and interactions serving to regulate chromatin function in a complex chemical language known as the "histone code." The alkaline property of histones may in part explain why such a large number of cross-links in and among these proteins is present in these data.

Figure 13:
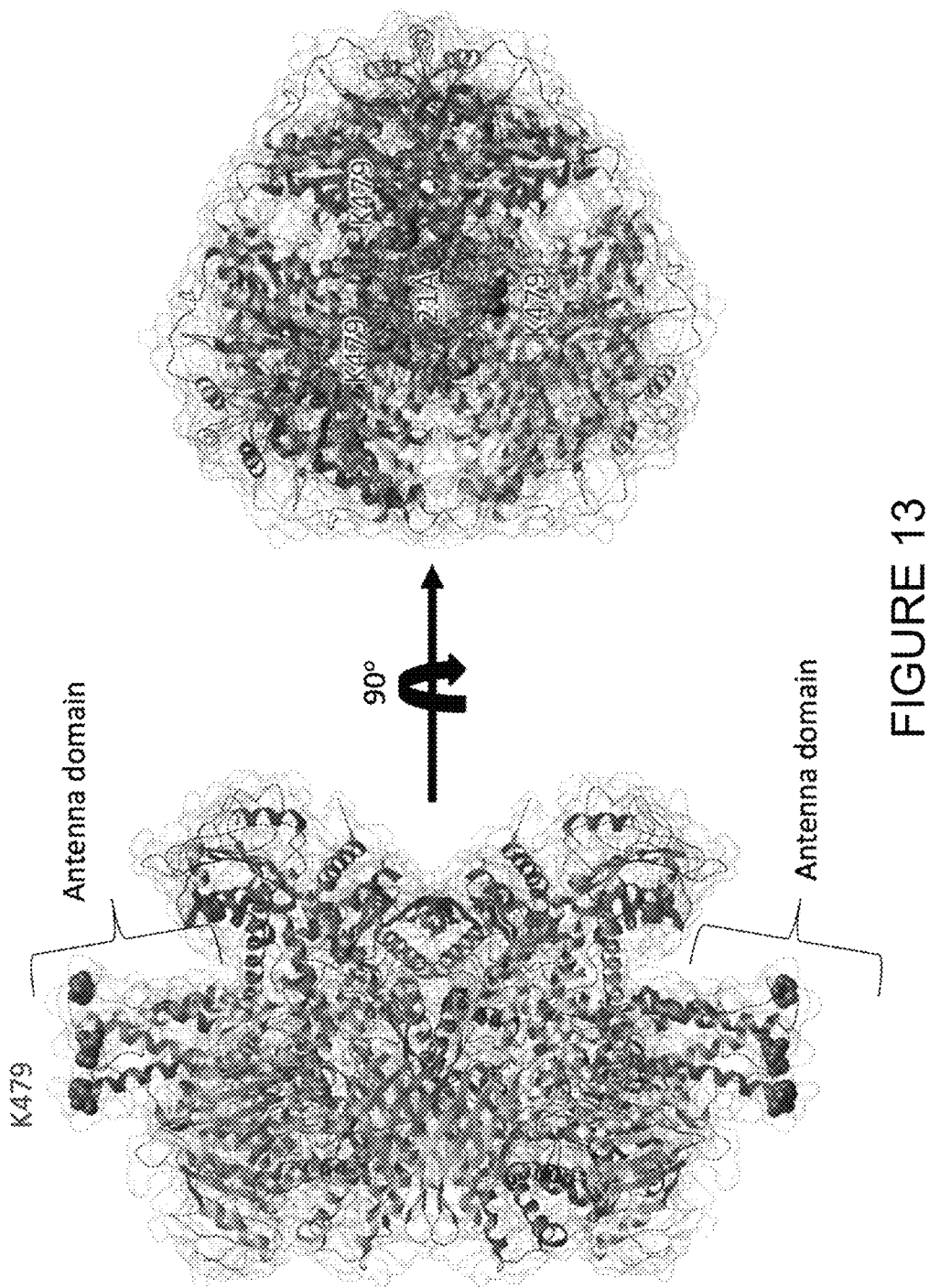
FIG. 13. Crystal structure of glutamate dehydrogenase (PDB: 1L1F) illustrating cross-linked site at lysine 480 at the tip of the antenna domain. (Note that K480 is labeled as K479 in the figure due to absence of N-terminal Met residue from the start codon in the crystal structure.)

Mapping the observed histone cross-links onto the human chromatin x-ray crystal structure (PDB: 3AFA) (Tachiwana et al., 2010, Proc. Natl. Acad. Sci. U.S.A. 107: 10454-59), enabled reconstruction of the assembly of the octamer complex from information contained in the cross-linked sites at multiple levels (intraprotein, homodimer, and interprotein) (FIG. 13). Importantly the information provided by these cross-links sheds light on the structure and orientation of the nucleosome complexes as present in vivo. FIG. 14A illustrates the cross-linker reactive residues observed for each of the four types of core histone proteins. Disordered N-terminal and C-terminal regions not included in the crystal structure were drawn in manually to illustrate the multiple cross-linked sites observed on the histone tails. Interprotein cross-links including unambiguous homodimer cross-links between H3 and H4, and H2A and H2B are displayed on the tetramer structures in FIG. 14B; however, the N-terminal tails are excluded here for clarity. Finally cross-links between the H3-H4 subunits and the H2A-H2B subunits are displayed with the full chromatin structure in FIG. 14C.

Cross-Links Containing Post-Translational Modifications.

Figure 15:
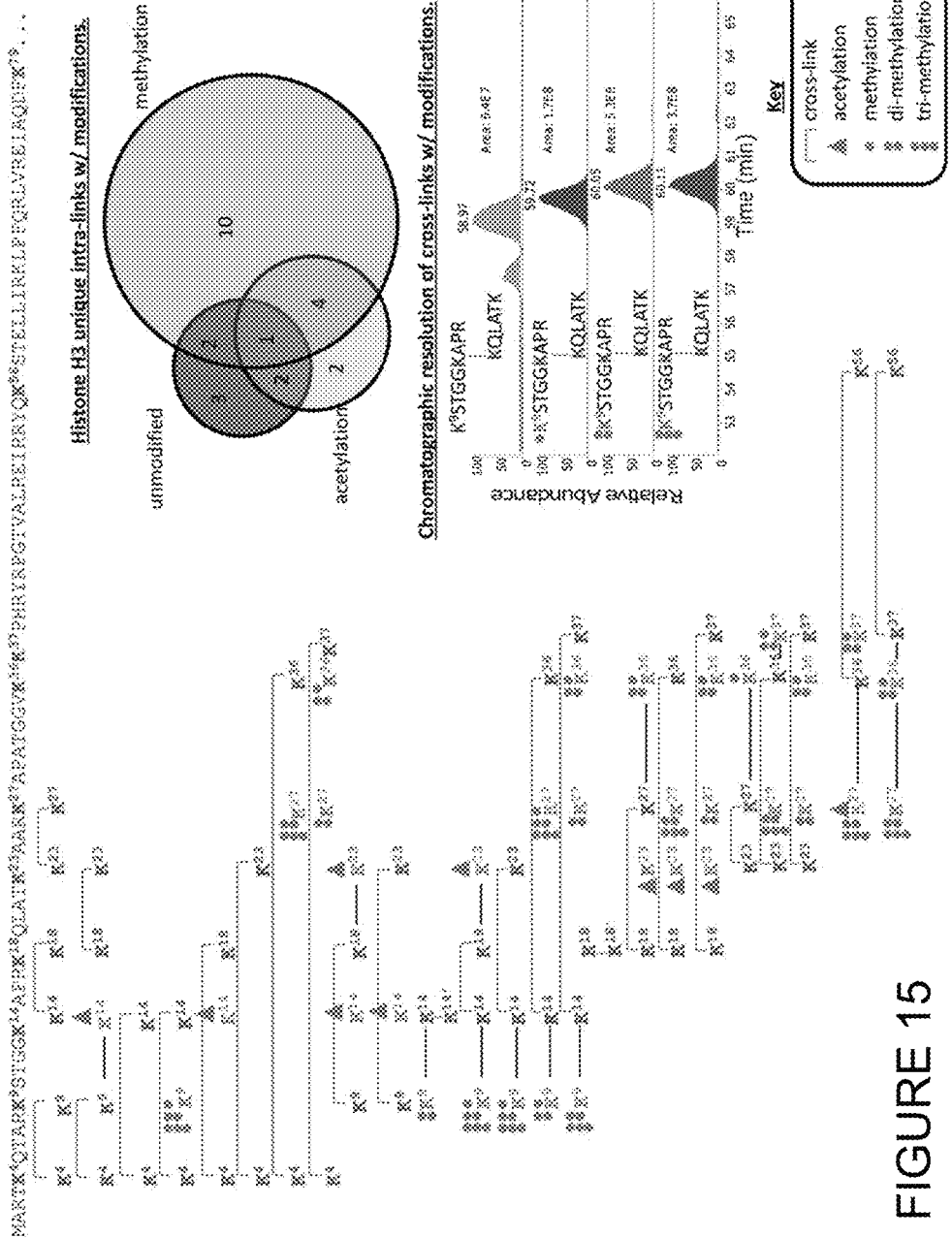
FIG. 15. Cross-link map of histone H3 including post-translational modifications. Sequence of histone H3 from residues 0-79 (SEQ ID NO: 17) with cross-linked sites highlighted in bold with residue numbers in superscript. Mapped cross-links are shown below and include post-translational modifications as indicated in the key. Venn diagram illustrates overlap of cross-links observed between unmodified, acetylated, or methylated (mono-, di-, tri-methylation grouped together). Extracted ion chromatographs are included for cross-linked peptides (KSTGGKAPR (SEQ ID NO: 18); KQLATK (SEQ ID NO: 19)) linking K14-K18 illustrating chromatographic resolution of various modified forms of this cross-linked peptide pair.

Histone H31 was the most heavily post-translationally modified protein detected in this study. In total, 13 unique post-translational modification sites on histone H31 were identified in cross-linked peptide pairs from human cells. These included the acetylation sites H3K14ac, H3K23ac, and H3K27ac, the mono-methylation sides at H3K9me, H3K27me, H3K36me and H3K37me, di-methylation sites H3K9me2, H3K27me2, H3K36me2, and H3K37me2, and tri-methylation sites H3K9me3, and H3K27me3. We have mapped the modifications observed at each site along with the observed cross-links onto the sequence for histone H3 in FIG. 15. It should be noted that except for the cases of unambiguous homodimer cross-links, these data are not able to conclusively distinguish intramolecular from intermolecular linkages in histone tails. Regardless, these results provide interesting insight into the topology of histone H3 and how it is altered with varying post-translational modification. For instance, cross-links between residues K4-K23, K18-K18, and K18-K23 are only observed with unmodified peptides. In contrast cross-links between residues K4-K36, K4-K37, K14-K14, K14-K23, K14-K36, K14-K37, K14-K56, K23-K36, K23-K37, and K37-K56 of histone H3 are only observed with mono-, di-, or tri-methylation present on a site on one of the cross-linked peptides. Linkages unique to acetylation modifications include K4-K18 and K9-K18. Overlap of the histone H3 intralinks with the presence of post-translational modifications is illustrated by the Venn diagram in FIG. 15. Interestingly, linkages between the end of the N-terminal tail (K4) and the base of the tail (K36 and K37) are only observed when there is a di- or tri-methylation at K27. Similarly cross-links between K14 and K23, K36, K37, and K53 are only observed with mono-, di-, or tri-methylation at H3K9. Various degrees of methylation at H3K9 are known to each have distinct effects over chromatin structure and activation or repression of specific genes. Cross-links were observed between H3K14 and K60 of N-actetyltransferase 10 (NAT10), a protein known to acetylate histones and stimulate telomerase activity, when either H3K9me2 or H3K9me3 were present suggesting these modifications could be important for this interaction. The interconversion between the different states of methylation at H3K9 is regulated by a diverse set of methyltransferases and demethylases. Partial chromatographic resolution of cross-linked peptides between residues 14 and 18 containing various degrees of methylation at H3K9 is shown in FIG. 15. As expected, with increasing degrees of methylation the retention time is lengthened on average. In addition, the integrated chromatographic peak areas of each of the modified forms is different, with di-methylation at H3K9 having the largest area and the unmodified form having the smallest area, though it should be noted peak areas may not be directly comparable across modification states because of differing ionization efficiencies. However the ability to chromatographically separate cross-linked peptides with differing modification states opens the possibility to quantify changes to various forms across different biological states employing stable isotope labeling techniques. The information obtained by such measurements would be distinct from global levels of modification at a specific site because of the topological information contained in the cross-linked peptide pair.

For the case of histone H4, acetylation modification was observed at H4K16ac. The intraprotein cross-link between K5-K12 was observed in the presence and absence of H4K16ac. Similarly a cross-link between H4K12 and H2BK108 was observed in the presence and absence of H4K16ac. Acetylation at H4K16ac has been shown to inhibit formation higher order chromatin structure contributing to de-condensation of chromatin fibers. Furthermore the acetylation state of H4K16 has been shown to regulate interactions between various forms of chromatin and interacting proteins including Sir3, ISWI, and Bdf1. We also identified two post-translationally modified sites of elongation factor 1-alpha (EF1A1) in cross-linked relationships including trimethylation on K35 and dimethylation on K54. Both of these modifications have been previously observed in EF1A1 isolated from rabbit reticulocytes. Although the biological roles of methylation on these two sites of EF1A1 have not be characterized, Lamberti et al. propose that these modifications increase the enzymatic activity of EF1A1 (Lamberti et al., 2004, Amino Acids 26:443-48). EF1A1 is a core component of the protein synthesis machinery promoting the GTP-dependent binding of aminoacyl-tRNA to the A-site of ribosomes during protein biosynthesis however has additional roles in cell signaling and apoptosis pathways.

As demonstrated by these results, it is now possible to directly monitor the topological effects of post-translational modifications at discrete sites in proteins using in vivo cross-linking with mass spectrometry. This opens the door to many future proteomics experiments in which the effects of varying levels and types of post-translational modifications across differing biological states can be directly linked to changes in protein topology and interactions.

New insights into interaction topologies. These cross-linking results provide new insight into protein interactions as they exist in the cell. This can be in the form of novel interacting partners or new topological information on known protein-protein interactions for which no previous structural information exists. One such example is the known interacting partners prohibitin (PHB) and prohibitin-2 (PHB2). Prohibitins are highly conserved, ubiquitous, and pleiotropic proteins implicated in a diversity of biological processes including proliferation, regulation of transcription, apoptosis, and cellular senescence. Evidence from yeast suggests prohibitins primarily localize to the inner mitochondrial membrane where PHB and PHB2 (a.k.a. BAP32 and BAP37) assemble into a ring shaped complex of approximately 1.2-1.4 MDa consisting of approximately 14 PHB-PHB2 dimers. The stabilities of PHB and PHB2 are also linked as they are readily degraded in the absence of their respective partner. In addition to their role in mitochondrial function, evidence also indicates prohibitins localize to the nuclear and the plasma membranes where they function in transcriptional regulation and signal transduction. Prohibitins are also emerging as potential therapeutic targets due to evidence implicating them in human health disorders including HIV, cancer, inflammatory disorders, diabetes, and obesity. Therefore there is much interest in understanding the molecular mechanisms by which prohibitins are able to carry out their diverse functions. Membrane proteins such as the prohibitins are notoriously difficult to study with structural techniques such as NMR and x-ray crystallography and unfortunately, structural details on prohibitins are scarce.

Figure 16:
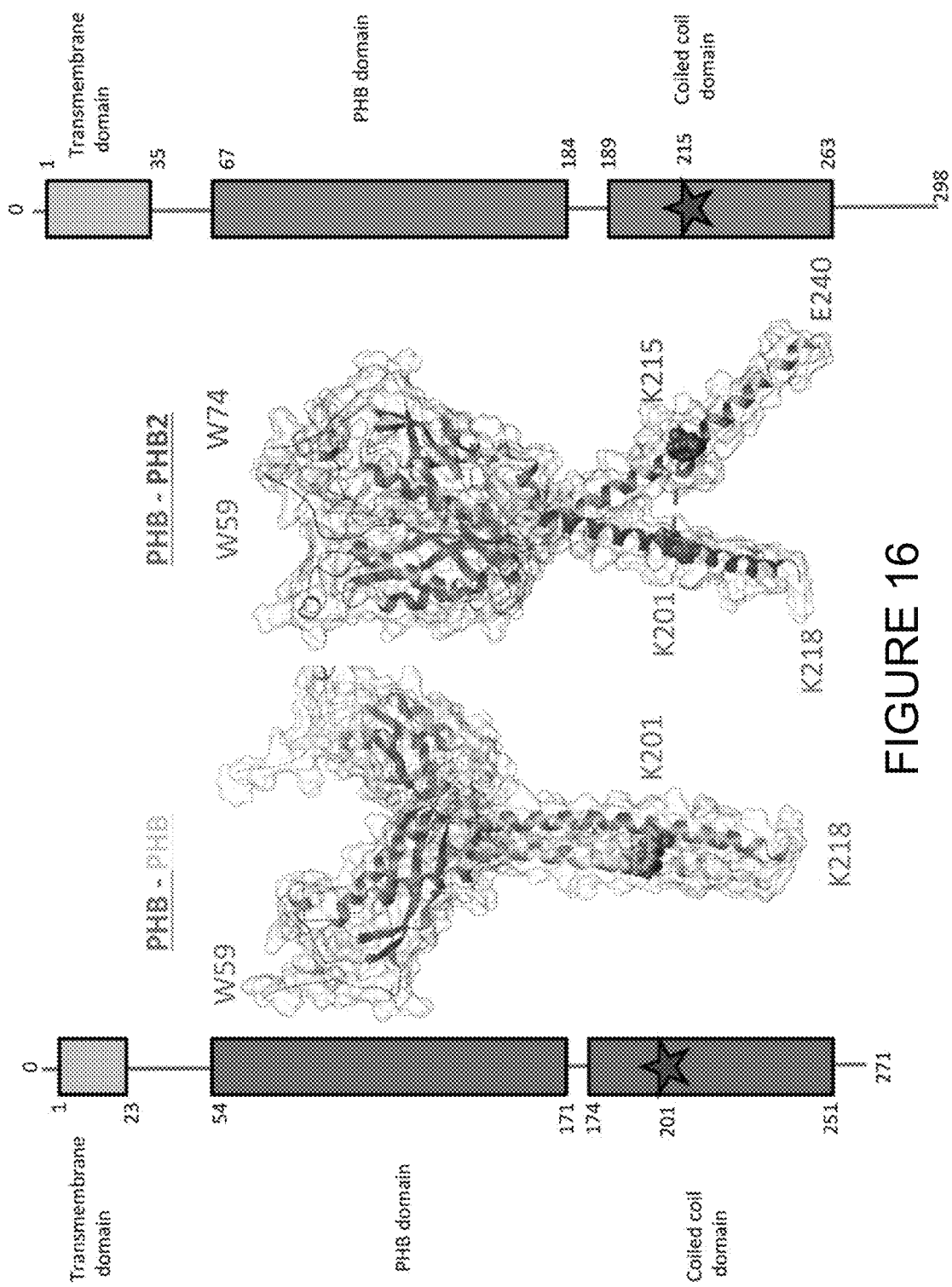
FIG. 16. Model structures for PHB-PHB homodimer and PHB-PHB2 dimer generated through homology modeling and molecular docking using distance constraints from cross-linked residues. The cross-linked sites PHB K201 and PHB2 K215 are located in the C-terminal domain thought to be important for stabilizing this interaction.

Using PIR cross-linking and ReACT in HeLa cells, a cross-link was identified between K201 of PHB and K215 of PHB2. Importantly these sites exist within predicted coiled-coil domains of PHB and PHB2 thought to be important for interaction between prohibitin subunits. Interestingly, the site of in vivo cross-linking between PHB and PHB2 in human cells reported here is conserved in vitro in purified yeast complexes where K204 was identified as cross-linked to K233 of PHB2. To construct a molecular model for the PHB-PHB2 dimer we first obtained homology models for PHB (residues 59-218, with 99.9% confidence) and PHB2 (residues 73 to 239, with 100% confidence) monomers using the protein structure prediction software Phyre2. Both models were constructed using the crystal structure of a core domain of stomatin from *Pyrococcus horikoshii*(PDB: 3BK6). The monomers were docked using PatchDock using distance constraints derived from the cross-linked residues identified here. The top scoring PHB-PHB2 dimer and PHB-PHB homodimer models from PatchDock are shown in FIG. 16. Although slight differences exist between the homodimer and heterodimer models, the alpha helical C-terminal domains in both of these models are interacting when cross-linking restraints are applied. For comparison, dimer models for these two complexes were generated without cross-linking distance constraint information and are shown in FIGS. 17A-17D. It can be seen that without applying the information from the cross-linked sites the resulting dimer models are quite different with the C-terminal domains on opposite sides of the complex. Despite the previous lack of evidence for any PHB homo-oligomers, these results also provide the first direct evidence for a prohibitin homodimer with an unambiguous peptide homodimer cross-link observed between K201 of PHB. Taken together, these results suggest these lysine sites to be important for homo- and hetero-interactions in human prohibitin. Knowledge of this interaction topology could be of potential use in future development of therapeutics targeting PHB.

Serving as another example of new protein interaction topology revealed in these data is the cross-link between K591 of stabilin-1 (STAB1) and K563 of ribophorin-1 (RPN1). There are no existing structures for either of these proteins in the PDB. RPN1 is an essential component of the N-oligosaccharyl transferase (OST) complex responsible for the transfer of oligosaccharides from dolichol to N-X-(S/T) motifs on nascent membrane proteins. RPN1 has been shown to transiently associate with a subset of newly synthesized membrane proteins immediately upon leaving the Sec61 translocon. Results from in vitro cross-linking experiments have suggested RPN1 serves to bind and deliver substrate proteins to the catalytic core of the OST. However, there is no existing evidence for interaction between RPN1 and STAB1 and these proteins are separated by two nodes in the IntAct database. STAB1 is a transmembrane receptor glycoprotein protein with ascribed functions in endocytosis, angiogenesis, inflammation, cell adhesion, and cell-cell interactions among others. STAB1 contains 7 fasciclin (FAS), 16 epidermal growth factor (EGF)-like, and 2 laminin-type EGF-like domains as well as a C-type lectin-like hyaluronan-binding Link module. The site of cross-linking (K591 of RPN1, K563 of STAB1) links a predicted cytoplasmic domain on RPN1 (residues 457-606) to the second extracellular FAS domain in STAB1 (residues 505-640). This FAS domain also contains a single N-glycosylation motif (NIS, residues 605-607). These results identify STAB1 as a potential novel substrate of RPN1.

Example 7

Cell Penetration of PIR Crosslinkers

For in vivo cross-linking and study of proteins other than membrane surface proteins, cell penetration of the cross-linker is important. The biotin group on PIR molecules provides a useful handle to perform assays and determine molecular penetration into cells. Using gold-coupled nanoparticle antibodies and electron microscopy, previous Rink-based PIR molecules were shown to penetrate and react with proteins in the cytosol of Gram-negative bacteria. To obtain complimentary verification of the membrane permeability of PIR molecules used with HeLa cells in the present study, we used fluorescent confocal microscopy.

For confocal microscopy samples, HeLa cells were cultured as described above in 35-mm Petri dishes with number 1.5 coverglass bottom (Mat Tek, Ashland, Mass.). When the cells reached 80% confluence they were washed five times with PBS buffer and reacted with 1 mm PIR cross-linker for 1 h. at room temperature. After the cross-linking reaction, cells were again washed 5 times with 2 ml PBS and fixed by addition of 10% formalin for 10 min at room temperature. Following fixation, cells were incubated with 0.1% triton X-100 in 1 ml PBS for 10 min. The cells were then incubated with 1 µg/ml NeutrAvidin OR green 488 (Invitrogen, Grand Island, N.Y.) in 1 ml PBS containing 0.1% triton X-100 for 1 h. in the dark with constant shaking. Cells were then washed three times with 2 ml PBS followed by incubation with 1 µg/ml propidium iodide for 10 min in PBS. Confocal fluorescent imaging was performed in the red and green fluorescent channels using a Nikon A1R confocal microscope using a 60× water immersion objective.

Confocal images of fluorophore-coupled avidin on PIR-reacted HeLa cells illustrated PIR penetration into cytoplasm and nuclear regions and labeled sites on intracellular proteins including nuclear proteins (FIG. 9).

Example 8

In Vitro Crosslinking of Protein Kinase A (PKA) Subunits

The ReACT platform can also identify protein interfaces in systems where a complete structure of the complex is not available. To illustrate this, we investigated intermolecular PPIs in between the subunits of the type 1 cAMP-dependent protein kinase (protein kinase A, PKA) holoenzyme.

Although most of the PKA protein structure has been resolved by X-ray crystallography, regions of the protein interface between the R and C subunits remain refractory to conventional structural biology approaches. In the in active state, PKA holoenzyme is composed of two regulatory subunits and two catalytic subunits (R2C2). The regulatory subunit RIα is a 43 kDa protein which consists of an ordered N-terminal region an ordered C-terminal region, and a disordered flexible linker region between the two ordered regions. This flexible region encompasses an inhibitor site that binds to an active site cleft in the C subunit in the inactive holoenzyme. The RIα N-terminal region has been shown to be critical for docking and dimerization with A-Kinase Anchoring Proteins (AKAPs), whereas, the C-terminal region is responsible for substrate binding. Both, the C-terminal and N-terminal ordered domains have been crystallized; however, the flexible, disordered linker region in RIα has not been successfully probed via crystallography. In our in vitro experiment, samples containing RIα alone and RIα together with the catalytic subunit (C) were each cross-linked using the BDP PIR compound.

The catalytic subunit of PKA was expressed from pET15b as an N-terminal 6×His-tag fusion protein in BL21(DE3) pLysS cells (Invitrogen). Expression was induced with 1 mM IPTG when cells reached an OD600≈0.6. Cells were grown at 37° C. for 4 hours and then pelleted by centrifugation at 5000×g for 10 minutes. Cells were lysed by resuspension in 50 mL nickel lysis buffer (20 mM NaPhosphate pH 7.5, 0.5 M NaCl, 20 mM imidazole, 5 mM TCEP, 1 mM benzamidine, one EDTA-free protease inhibitor tablet (Roche), 0.1 µg/mL lysozyme, 2.5 U/mL benzonase (EMD) and 2 mM $MgCl_2$). Triton X-100 was added to 0.5% and lysates were incubated for 30 minutes at 4° C., followed by centrifugation at 40,000×g for 30 minutes. Cleared lysates were incubated with 2 mL Ni Sepharose 6 FF (GE Healthcare) for 1 h prior to washing in 20 mM NaPhosphate pH 7.5, 0.5 M NaCl, 20 mM imidazole, 5 mM TCEP and elution in 20 mM NaPhosphate pH 7.5, 0.5 M NaCl, 300 mM imidazole, 1 mM dithiothreitol (DTT). Eluate was further polished by gel filtation using a HiLoad 16/600 Superdex 200 column (GE Healthcare) with 25 mM Tris pH 7.5, 200 mM NaCl, 1 mM DTT, 1 mM EDTA as the column buffer. Peak fractions were collected, dialyzed overnight against GF buffer containing 20% glycerol and flash frozen in liquid $N_2$.

The RIα subunit of human PKA in pGEX6P1 was expressed as a GST-fusion protein in E. coli as above. Cells were lysed in 50 mM Tris HCl, pH 7.5, 500 mM NaCl, 1 mM DTT, 1 mM EDTA, 2 mM $MgCl_2$, 1 mM benzamidine, one EDTAfree protease inhibitor tablet (Roche), 0.1 µg/mL lysozyme and 2.5 U/ml benzonase (EMD). Triton X-100 was added to 0.5% and lysates were incubated for 30 minutes at 4° C. The protein was purified from cleared lysates using glutathione Sepharose-4B (Amersham Biosciences) followed by extensive washing in lysis buffer. Bound protein was cleaved from the beads overnight with PreScission protease (Amersham Biosciences) and finally purified by size-exclusion chromatography as above. Peak fractions were collected, dialyzed overnight against 20 mM HEPES, 150 mM NaCl, 1 mM EDTA and 1 mM DTT, and flash frozen in liquid $N_2$.

RIα was cross-linked at a concentration of 1.2 mg/mL with 1 mM BDP-NHS reagent to generate the RI only sample. RIα and pkaC (the PKA catalytic subunit) were incubated in a 1:2 molar ratio with a final concentration of 1.2 mg/mL for 2 hrs at room temperature prior to cross-linking. BDP-NHS cross-linking reagent was added to the R:C sample to 1 mM final concentration.

Figure 19:
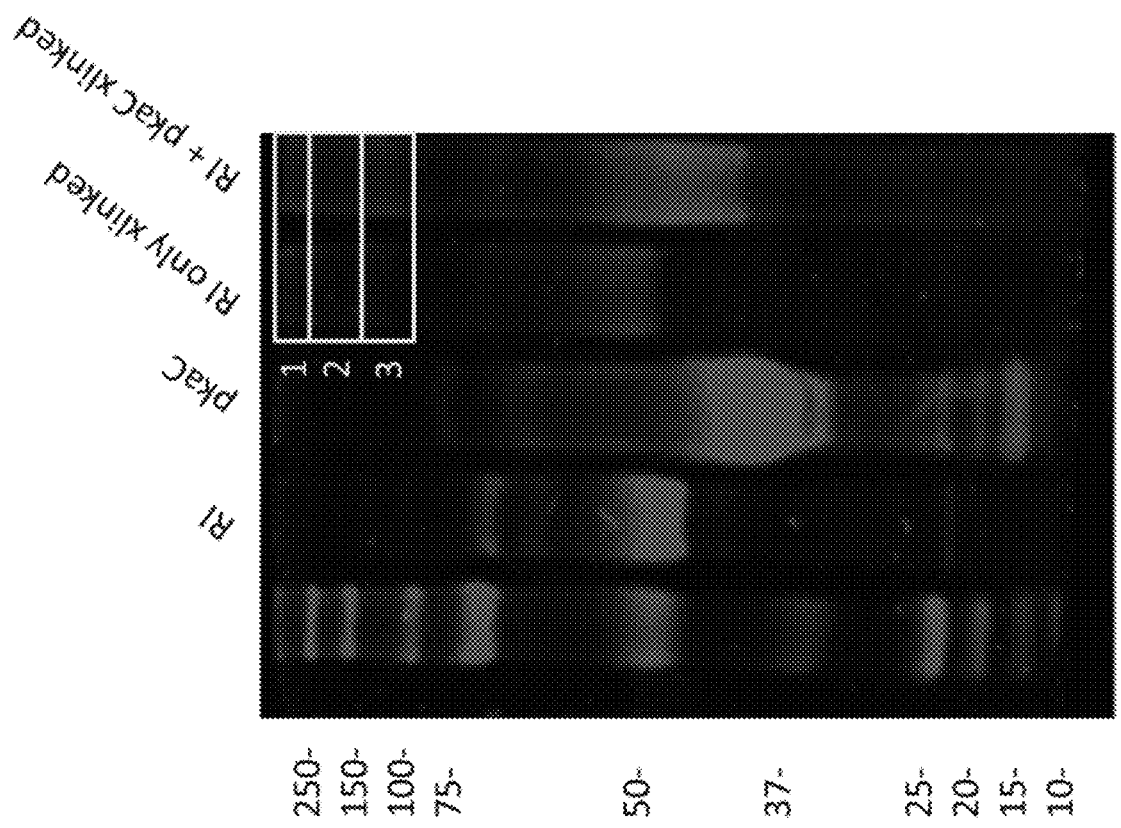
FIG. 19. SDS-PAGE separation of in vitro PKA experiments. Lanes are labeled accordingly along the top of the gel. Boxes indicate sections excised for in-gel digest ReACT analysis.

Cross-linking reactions were allowed to proceed for 1 hr at room temperature and then quenched with 100 mM ammonium bicarbonate. 50 uL aliquots from each sample were set aside for SDS-PAGE analysis (FIG. 19), while the remainder was trypsinized in the solution phase. After cross-linking, disulfide bonds were reduced using 5 mM Tris(2-carboxyethyl)phosphine (TCEP) and the resulting free thiols were alkylated using 10 mM iodoacetamide (IAA). Digestion was carried out at using a 1:200 w/w ratio of sequencing grade modified trypsin (Promega, Madison, Wis.) to protein and incubating at 37° C. overnight with constant mixing. The samples were desalted using C18 Sep-Pak (Waters Corporation, United Kingdom) and dried in a centrifugal concentrator (Genevac, Gardiner, N.Y.). Unreacted and dead-end cross-links were removed using Macro SCX Spin Columns (Nest Group Inc., Southborough, Mass.). The fractions were biotin affinity enriched for BDP cross-linked peptide products using Ultralink Monomeric Avidin (Pierce, Rockford, Ill.). Samples were centrifugally concentrated and re-solubilized using Solvent A in preparation for LC-MS analysis.

ReACT analysis of RIα-only samples enabled identification of three unambiguous RIα homodimer cross-linked peptides indicating proximal sites within the RIα dimer in solution, two of which appeared within the disordered linker region. From the RIα, C mixed samples, one heterodimeric linkage between R:C protomers was identified. In addition, homodimer RIα cross-linked peptides identified within the disordered linker region in RIα-only samples, K59-K59 and K92-K92 were still observed from cross-linking experiments that contained the catalytic subunit. However, the homodimeric cross-linked peptide pair K214-K216 identified in RIα-only samples was not observed from these mixed samples. The loss of K214-K216 cross-linked peptides and the appearance of inter-protein cross-linked pairs between RIα and C demonstrate topological features of the RIα dimer are altered upon binding the catalytic domain, consistent with the recognized importance of allostery in this complex.

Figure 18A:
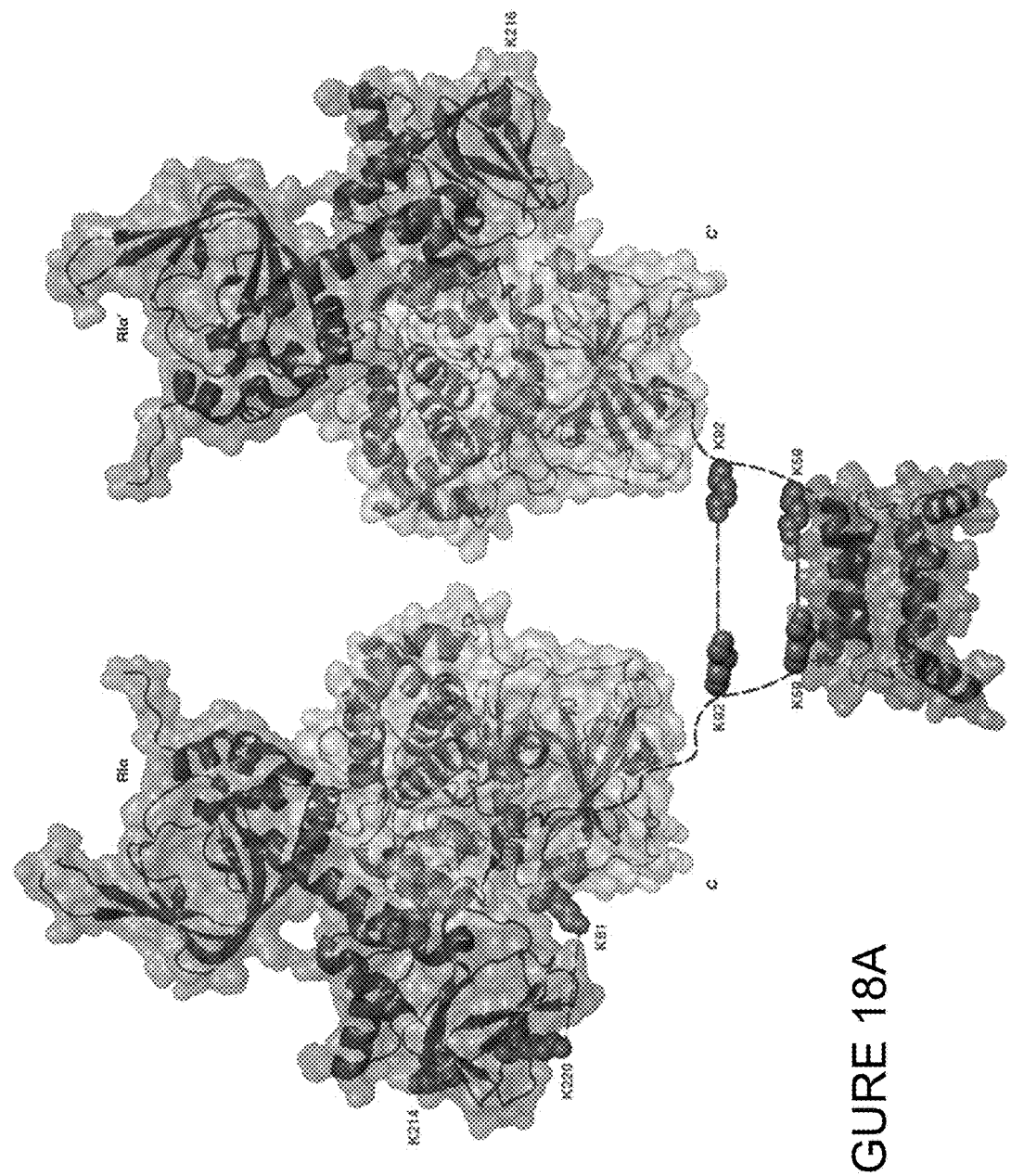
FIGS. 18A-18B.
Figure 18B:
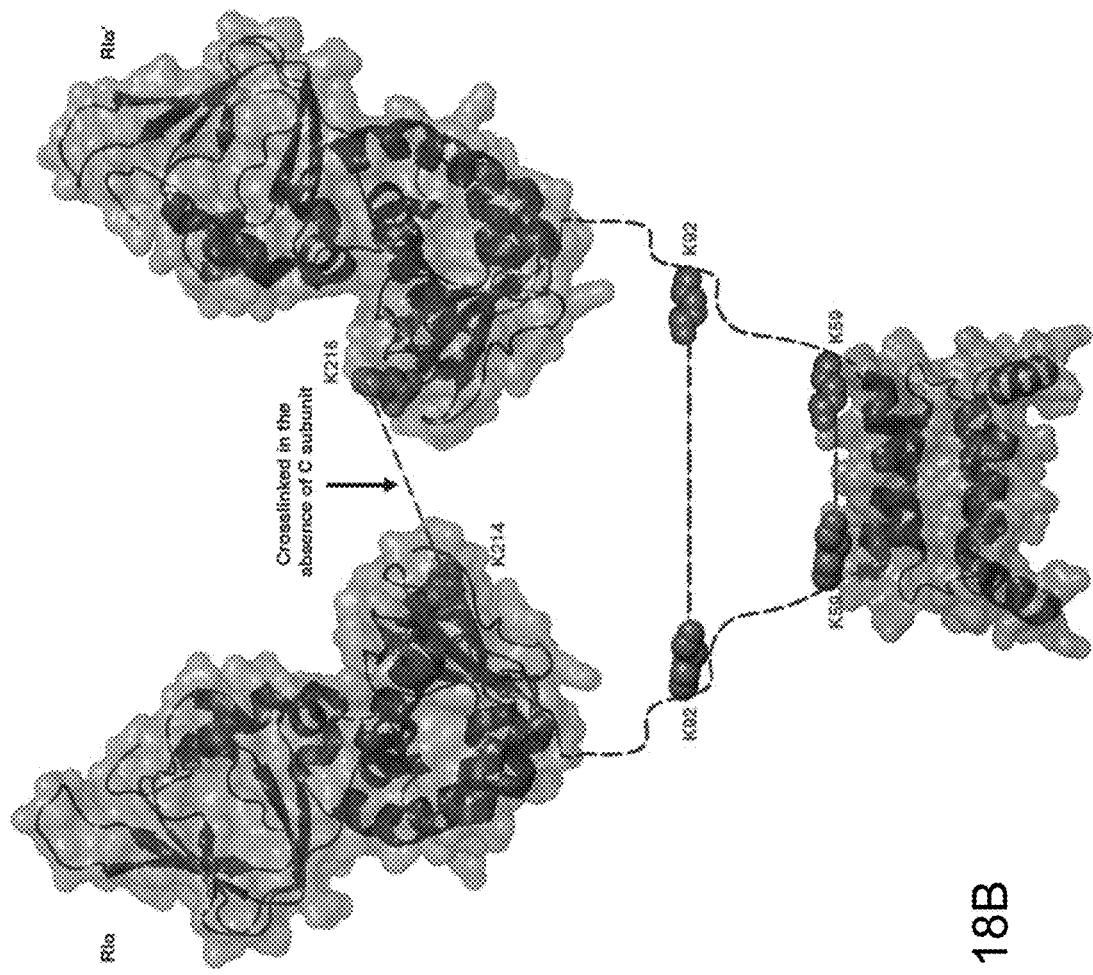

To better illustrate cross-linked sites on PKA identified with ReACT, the observed cross-linked sites were mapped on the measured structures (PDB: 2QCS, 1RGS, 3IM3) and flexible linker region as shown in FIG. 18. PKA undergoes a conformational change in which the two cAMP binding cassettes are brought together by a rearrangement of a central alpha helix. Our cross-linking data indicate that this change in conformation allows formation of an additional homodimeric cross-link between K216 and K214. Since it is unknown how the tetrameric PKA holoenzyme is arranged, there are multiple structural models that can explain our cross-linking data. One such model (FIG. 18A) arranges the heterodimer such that the catalytic subunits are placed between the RIα subunits, and upon release of the C subunit, cAMP binding cassette swings towards the dimeric interface (FIG. 18B), allowing the observation of the additional cross-link (K214-K216). Other structural models based on low-resolution SAXS data, and observations from crystal packing of the partial complex place the catalytic subunit on the outside of the tetrameric complex. However, our cross-linking data identifies a new homodimeric interface upon release of the catalytic subunit that is best explained by the model in FIG. 18B.

Example 9

Potential Drug Targets Elucidated Using ReACT

Many of the protein-protein interactions elucidated by the methods disclosed herein are potential drug targets. Three such potential drug targets are described below.

Potential Drug Targets for Cancer.

Heat shock protein 90 (HSP90) is a molecular chaperone that is commonly observed being overexpressed in cancerous cells where it functions to stabilize hundreds of client proteins many of which are known oncoproteins required for cancer cell survival. It therefore is recognized as a potential therapeutic target and many HSP90 inhibitors have been developed and are currently undergoing clinical trials. The disclosed methods were used to identify cross-linked peptides identifying homo-dimer interactions for both the alpha and beta isoforms of HSP90 as well as heterodimer interactions between the alpha (HS90A) and beta (HS90B) isoforms. These are shown in Table 2. Furthermore cross-linked peptide pairs identify interactions between HSP90 and it known co-chaperone Stress-induced-phosphoprotein 1 (STIP1). Drugs that inhibit interactions with HSP90 are thus potentially useful as cancer therapeutics.

TABLE 2

Selected cross-linked peptides identifying HSP90 interactions.

| Peptide1 (SEQ ID NO) | Peptide2 (SEQ ID NO) | Protein1 (GenBank No.; SEQ ID NO) | Protein2 (GenBank No.; SEQ ID NO) |
|---|---|---|---|
| FYEQFSK$^{443}$NIK (1) | FYEQFSK$^{443}$NIK (1) | HS90A (CAI64495.1; 20) | HS90A (CAI64495.1; 20) |
| FYEAFSK$^{435}$NLK (2) | FYEAFSK$^{435}$NLK (2) | HS90B (AAH68474.1; 21) | HS90B (AAH68474.1; 21) |
| FYEQFSK$^{443}$NIK (1) | FYEAFSK$^{435}$NLK (2) | HS90A (CAI64495.1; 20) | HS90B (AAH68474.1; 21) |
| FYEQFSK$^{443}$NIK (1) | K$^{624}$HLEINPDHPIVETLR (3) | HS90A (CAI64495.1; 20) | HS90B (AAH68474.1; 21) |
| APFDLFENK$^{347}$K (4) | FYEQFSK$^{443}$NIK (1) | HS90B (AAH68474.1; 21) | HS90A (CAI64495.1; 20) |

TABLE 2-continued

Selected cross-linked peptides identifying HSP90 interactions.

| Peptide1 (SEQ ID NO) | Peptide2 (SEQ ID NO) | Protein1 (GenBank No.; SEQ ID NO) | Protein2 (GenBank No.; SEQ ID NO) |
|---|---|---|---|
| FYEQFSK$^{443}$NIK (1) | K$^{434}$AAALEAMK (5) | HS90A (CAI64495.1; 20) | STIP1 (AAH39299.1; 22) |
| FYEAFSK$^{435}$NLK (2) | K$^{434}$AAALEAMK (5) | HS90B (AAH68474.1; 21) | STIP1 (AAH39299.1; 22) |

Cross-linked Lys residues indicated in bold with amino acid residue number in superscript Potential Drug Targets for Antibiotic Resistance in *A. baumannii*.

The protein Oxa-23 exhibits carbapenemase activity and is the key resistance function found in the clinically most problematic carbapenem resistant *A. baumannii* strains. CarO is a carbapenem-associated resistance outer membrane porin, not previously known to interact directly with Oxa-23. CarO is thought to be required for L-ornithine uptake since CarO deficient strains were specifically impaired for growth on L-ornithine. However, resistance to both imipenem and meropenem in multidrug-resistant clinical strains of *A. baumannii* has been found to be associated with the loss of CarO. These observations suggest that CarO serves a beneficial role in amino acid and possibly other nutrient uptake but this porin is also associated with carbapenem entry into the cell. These findings suggest that one strategy employed by bacteria like *A. baumannii* to increase antibiotic resistance yet maintain active porin function may be to evolve porin interactions with β-lactamase enzymes. Beneficial maximum β-lactam hydrolysis could be achieved by localizing the β-lactamase in the cell where β-lactam concentration is maximal. This is likely to be the point of entry into the cell and, therefore, it may be anticipated that Oxa-23 and CarO form a close interactions. The PIR data acquired using the methods disclosed herein are the first to demonstrate this interaction and provide topological data on this complex. These results, some of which are shown in Table 3, together with the known crystal structures of Oxa-23 and CarO demonstrate that, in cells, Oxa-23 is cross-linked on a periplasmic loop of the CarO structure.

capture underlying signaling pathways and host cell functions to establish persistent infections. In the gut, lung, skin and other organs, the human epithelial barrier serves as an infectious foothold for many bacterial pathogens and as an entry port for pathogens to disseminate into deeper tissues. Several host and pathogen proteins are known to be required for host cell attachment, such as type 1 pili, P-pili, type IV pili, curli and non-pilus proteins or OmpA. However, how exactly type IV pili mediate attachment remains unknown.

Mutant bacteria that lack one or more of the determinants above often fail to infect cells, as highlighted below. In *A. baumannii*, three outer membrane proteins (Omps) have been identified as fibronectin-binding proteins: OmpA, TonB-dependent copper receptor, and 34 kDa Omp. It has also been shown that either fibronectin inhibition and neutralization by specific antibodies or AbOmpA neutralization by specific antibodies significantly decreased adhesion of *A. baumannii* to human lung epithelial cells. Importantly, their data also support the notion that if known, protein-protein interaction binding interfacial regions between *A. baumannii* outer membrane proteins and host epithelial cellular proteins would be useful targets for disruption and enable novel infection control strategies of MDR *A. baumannii*.

PIR and ReACT experiments with *A. baumannii* cells that were incubated with human bronchial epithelial cells resulted in identification of more than 1766 non-redundant cross-linked peptide pairs from 661 proteins. Selected date is shown in Table 4. These include three non-redundant linkages between the known *A. baumannii* virulence factor, OmpA, and the human protein desmoplakin, which is an

TABLE 3

Selected cross-linked peptides identifying Oxa-23 and CarO interactions

| Peptide1 (SEQ ID NO) | Peptide2 (SEQ ID NO) | Protein1 (GenBank No.; SEQ ID NO) | Protein2 (GenBank No.; SEQ ID NO) |
|---|---|---|---|
| K$^{60}$INLYGN ALSR (6) | NDIAPYLGFG FAPK$^{178}$INK (7) | Oxa-23 (ACJ39972.1; 23) | CarO (ACN32317.1; 24) |

Cross-linked Lys residues indicated in bold with amino acid residue number in superscript Potential Drug Targets for *A. baumannii* Infection of Human Bronchial Cells.

Host cell adhesion constitutes a primary virulence factor. Most bacteria exist in their natural environment attached to surfaces and the majority of bacterial pathogens exploit specific adhesion to host cells as primary virulence factors. In most infectious diseases, adherence of pathogenic organisms to the host through host receptors is the initial event that serves to target the pathogen to a particular location to obligate component of functional desmosomes that serve as intercellular junctions to tightly link adjacent cells. The desmoplakin site K2714 that observed to be cross-linked to OmpA is within plakin repeat 3 in the subdomain C that binds intermediate filament proteins such as vimentin and epithelial keratins. Thus, interaction of *A. baumannii* OmpA with desmoplakin could serve to promote pathogen infiltration by disrupting interactions between host cells and providing an anchoring site for pathogen cells. Furthermore, the A. baumannii protein AB57_2521 that was identified linked to OmpA was also observed cross-linked at this site K2714 on desmoplakin, illustrating that OmpA and its binding partner AB57_2521 interact with human desmoplakin within the same region. These data indicate this interaction occurs when OmpA is present in native complexes which are important for host-pathogen interactions. This knowledge of protein interactions as well as regions within proteins that are involved in interspecies binding could lead to novel therapies that disrupt this interaction, prevent or impede bacterial invasion in human lung epithelial cells, decreasing the ability of A. baumannii to infect humans.

TABLE 4

Selected cross-linked peptides identifying OmpA-desmoplakin interactions.

| Peptide1 (SEQ ID NO) | Peptide2 (SEQ ID NO) | Protein1 (GenBank No.; SEQ ID NO) | Protein2 (GenBank No.; SEQ ID NO) |
|---|---|---|---|
| VFFDTNK$^{235}$SNIK DQYKPEIAK (8) | MSAAEAVK$^{2714}$EK (9) | OmpA (AAR83911.1; 25) | Desmoplakin (AAA85135.1; 26) |
| TK$^{319}$EGR (10) | MSAAEAVK$^{2714}$EK (9) | OmpA (AAR83911.1; 25) | Desmoplakin (AAA85135.1; 26) |
| LSTQGFAWDQPIA DNK$^{317}$TK (11) | MSAAEAVK$^{2714}$EK (9) | OmpA (AAR83911.1; 25) | Desmoplakin (AAA85135.1; 26) |

Cross-linked Lys residues indicated in bold with amino acid residue number in superscript

BIBLIOGRAPHY

Ali M. M., Roe S. M., Vaughan C. K., Meyer P., Panaretou B., Piper P. W., Prodromou C., Pearl L. H. (2006) Crystal structure of an Hsp90-nucleotide-p23/Sba1 closed chaperone complex. Nature 440, 1013-1017.

Anderson G A, Tolic N, Tang X, Zheng C, Bruce J E. Informatics strategies for large-scale novel cross-linking analysis. J Proteome Res. 2007; 6(9):3412-21.

Andres Leon E, Ezkurdia I, Garcia B, Valencia A, Juan D. EcID. A database for the inference of functional interactions in E. coli. Nucleic Acids Res. 2009; 37(Database issue):D629-35.

Apweiler R, Bairoch A, Wu C H, Barker W C, Boeckmann B, Ferro S, Gasteiger E, Huang H, Lopez R, Magrane M, Martin M J, Natale D A, O'Donovan C, Redaschi N, Yeh L S. UniProt: the Universal Protein knowledgebase. Nucleic Acids Res. 2004; 32(Database issue):D115-9.

Back J W, de Jong L, Muijsers A O, de Koster C G. Chemical cross-linking and mass spectrometry for protein structural modeling. Journal of molecular biology. 2003; 331 (2): 303-13.

Ban N, Nissen P, Hansen J, Moore P B, Steitz T A. The complete atomic structure of the large ribosomal subunit at 2.4 A resolution. Science. 2000; 289(5481):905-20.

Bauer A., Kuster B. (2003) Affinity purification-mass spectrometry. Powerful tools for the characterization of protein complexes. Eur. J. Biochem. FEBS 270, 570-578.

Bernstein F C, Koetzle T F, Williams G J, Meyer E F, Jr, Brice M D, Rodgers J R, Kennard O, Shimanouchi T, Tasumi M. The Protein Data Bank: a computer-based archival file for macromolecular structures. J Mol Biol. 1977; 112 (3):535-42.

Bich C., Maedler S., Chiesa K., DeGiacomo F., Bogliotti N., Zenobi R. (2010) Reactivity and applications of new amine reactive cross-linkers for mass spectrometric detection of protein-protein complexes. Anal. Chem. 82, 172-179.

Black J. C., Whetstine J. R. (2010) Chromatin landscape: methylation beyond transcription. Epigenetics 6, 9-15.

Bruce J. E. (2012) In vivo protein complex topologies: sights through a cross-linking lens. Proteomics 12, 1565-1575.

Chavez J D, Cilia M, Weisbrod C R, Ju H J, Eng J K, Gray S M, Bruce J E. Cross-linking measurements of the Potato leafroll virus reveal protein interaction topologies required for virion stability, aphid transmission, and virus-plant interactions. J Proteome Res. 2012; 11:2968-81.

Chavez J D, Liu N L, Bruce J E. Quantification of protein-protein interactions with chemical cross-linking and mass spectrometry. J Proteome Res. 2011; 10(4):1528-37.

Chen B., Piel W. H., Gui L., Bruford E., Monteiro A. (2005) The HSP90 family of genes in the human genome: insights into their divergence and evolution. Genomics 86, 627-637.

Chen Z A, Jawhari A, Fischer L, Buchen C, Tahir S, Kamenski T, Rasmussen M, Lariviere L, Bukowski-Wills J C, Nilges M, Cramer P, Rappsilber J. Architecture of the RNA polymerase II-TFIIF complex revealed by cross-linking and mass spectrometry. EMBO J. 2010; 29(4): 717-26.

Chen T, Jaffe J D, Church G M. Algorithms for identifying protein cross-links via tandem mass spectrometry. J Comput Biol. 2001; 8 (6):571-83.

Choudhary C., Kumar C., Gnad F., Nielsen M. L., Rehman M., Walther T. C., Olsen J. V., Mann M. (2009) Lysine acetylation targets protein complexes and co-regulates major cellular functions. Science 325, 834-840.

Chu F, Mahrus S, Craik C S, Burlingame A L. Isotope-coded and affinity-tagged cross-linking (ICATXL): an efficient strategy to probe protein interaction surfaces. J Am Chem Soc. 2006; 128 (32):10362-3.

Chu F., Shan S. O., Moustakas D. T., Alber F., Egea P. F., Stroud R. M., Walter P., Burlingame A. L. (2004) Unraveling the interface of signal recognition particle and its receptor by using chemical cross-linking and tandem mass spectrometry. Proc. Natl. Acad. Sci. U.S.A. 101, 16454-16459.

Dedmon M M, Patel C N, Young G B, Pielak G J. FlgM gains structure in living cells. Proc Natl Acad Sci USA. 2002; 99(20):12681-4.

Dever T. E., Costello C. E., Owens C. L., Rosenberry T. L., Merrick W. C. (1989) Location of seven post-translational modifications in rabbit elongation factor 1 alpha including dimethyllysine, trimethyllysine, and glycerylphosphorylethanolamine. J. Biol. Chem. 264, 20518-20525.

Dutton A., Adams M., Singer S. J. (1966) Bifunctional imidoesters as cross-linking reagents. Biochem. Biophys. Res. Commun. 23, 730-739.

Elias J E, Gygi S P. Target-decoy search strategy for increased confidence in large-scale protein identifications by mass spectrometry. Nat Methods. 2007; 4(3):207-14.

Ellis R J. Macromolecular crowding: obvious but underappreciated. Trends Biochem Sci. 2001; 26(10):597-604.

Emerson V., Holtkotte D., Pfeiffer T., Wang I. H., Schnölzer M., Kempf T., Bosch V. (2010) Identification of the cellular prohibitin 1/prohibitin 2 heterodimer as an interaction partner of the C-terminal cytoplasmic domain of the HIV-1 glycoprotein. J. Virol. 84, 1355-1365.

Fields S., Song O. (1989) A novel genetic system to detect protein-protein interactions. Nature 340, 245-246.

Gingras A C, Gstaiger M, Raught B, Aebersold R. Analysis of protein complexes using mass spectrometry. Nature reviews Molecular cell biology. 2007; 8 (8):645-54.

Gomes A F, Gozzo F C. Chemical cross-linking with a diazirine photoactivatable cross-linker investigated by MALDI- and ESI-MS/MS. J Mass Spectrom. 2010; 45 (8):892-9.

Graumann J, Scheltema R A, Zhang Y, Cox J, Mann M. A framework for intelligent data acquisition and real-time database searching for shotgun proteomics. Mol Cell Proteomics. 2012; 11(3):M111 013185.

Herraez A. Biomolecules in the computer: Jmol to the rescue. Biochem Mol Biol Educ. 2006; 34 (4):255-61.

Herzog F, Kahraman A, Boehringer D, Mak R, Bracher A, Walzthoeni T, Leitner A, Beck M, Hartl F U, Ban N, Malmstrom L, Aebersold R. Structural probing of a protein phosphatase 2A network by chemical cross-linking and mass spectrometry. Science. 2012; 337(6100): 1348-52.

Hoopmann M R, Weisbrod C R, Bruce J E. Improved strategies for rapid identification of chemically crosslinked peptides using protein interaction reporter technology. J Proteome Res. 2010; 9(12):6323-33.

Hopwood D. (1969) Fixatives and fixation: a review. Histochem. J. 1, 323-360.

Huang B X, Kim H Y, Dass C. Probing three-dimensional structure of bovine serum albumin by chemical crosslinking and mass spectrometry. Journal of the American Society for Mass Spectrometry. 2004; 15 (8):1237-47.

Ikeya T, Sasaki A, Sakakibara D, Shigemitsu Y, Hamatsu J, Hanashima T, Mishima M, Yoshimasu M, Hayashi N, Mikawa T, Nietlispach D, Walchli M, Smith B O, Shirakawa M, Guntert P, Ito Y. NMR protein structure determination in living *E. coli* cells using nonlinear sampling. Nat Protoc. 2010; 5(6):1051-60.

Ispolatov I., Yuryev A., Mazo I., Maslov S. (2005) Binding properties and evolution of homodimers in protein-protein interaction networks. Nucleic Acids Res. 33, 3629-3635.

Jenuwein T., Allis C. D. (2001) Translating the histone code. Science 293, 1074-1080.

Kahraman A., Malmstrom L., Aebersold R. (2011) Xwalk: computing and visualizing distances in cross-linking experiments. Bioinformatics 27, 2163-2164.

Kalkhof S, Ihling C, Mechtler K, Sinz A. Chemical crosslinking and high-performance Fourier transform ion cyclotron resonance mass spectrometry for protein interaction analysis: application to a calmodulin/target peptide complex. Anal Chem. 2005; 77 (2):495-503.

Karadzic I, Maupin-Furlow J, Humbard M, Prunetti L, Singh P, Goodlett D R. Chemical cross-linking, mass spectrometry, and in silico modeling of proteasomal 20S core particles of the haloarchaeon *Haloferax volcanii*. Proteomics. 2012; 12(11):1806-14.

Katritzky A R, Yang B, Qiu G, Zhang Z. ChemInform abstract: A convenient trifluoroacetylation reagent: N-(Trifluoroacetyl)succinimide. ChemInform. 1999; 30(19):no-no.

Kelley L. A., Sternberg M. J. (2009) Protein structure prediction on the Web: a case study using the Phyre server. Nat. Protocols 4, 363-371.

Kerrien S, Aranda B, Breuza L, Bridge A, Broackes-Carter F, Chen C, Duesbury M, Dumousseau M, Feuermann M, Hinz U, Jandrasits C, Jimenez R C, Khadake J, Mahadevan U, Masson P, Pedruzzi I, Pfeiffenberger E, Porras P, Raghunath A, Roechert B, Orchard S, Hermjakob H. The IntAct molecular interaction database in 2012. Nucleic acids research. 40(Database issue):D841-6.

Kim S. C., Sprung R., Chen Y., Xu Y., Ball H., Pei J., Cheng T., Kho Y., Xiao H., Xiao L., Grishin N. V., White M., Yang X. J., Zhao Y. (2006) Substrate and functional diversity of lysine acetylation revealed by a proteomics survey. Mol. Cell 23, 607-618.

Kluger R., Alagic A. (2004) Chemical cross-linking and protein-protein interactions-a review with illustrative protocols. Bioorg. Chem. 32, 451-472.

Kurdistani S. K., Tavazoie S., Grunstein M. (2004) Mapping global histone acetylation patterns to gene expression. Cell 117, 721-733.

Kuriyan J., Eisenberg D. (2007) The origin of protein interactions and allostery in colocalization. Nature 450, 983-990.

Kzhyshkowska J. (2010) Multifunctional receptor stabilin-1 in homeostasis and disease. TheScientificWorldJournal 10, 2039-2053.

Lamberti A., Caraglia M., Longo O., Marra M., Abbruzzese A., Arcari P. (2004) The translation elongation factor 1A in tumorigenesis, signal transduction and apoptosis: review article. Amino Acids 26, 443-448.

Lauber M. A., Reilly J. P. (2011) Structural analysis of a prokaryotic ribosome using a novel amidinating crosslinker and mass spectrometry. J. Prteome Res. 10, 3604-3616.

Leitner A, Reischl R, Walzthoeni T, Herzog F, Bohn S, Forster F, Aebersold R. Expanding the chemical cross-linking toolbox by the use of multiple proteases and enrichment by size exclusion chromatography. Mol Cell Proteomics. 2012; 11(3):M111.014126.

Leitner A, Walzthoeni T, Kahraman A, Herzog F, Rinner O, Beck M, Aebersold R. Probing native protein structures by chemical cross-linking, mass spectrometry, and bioinformatics. Mol Cell Proteomics. 2010; 9(8):1634-49.

Li Y., Zhang T., Schwartz S. J., Sun D. (2009) New developments in Hsp90 inhibitors as anti-cancer therapeutics: mechanisms, clinical perspective and more potential. Drug Resistance Updates 12, 17-27.

Liu F, Wu C, Sweedler J V, Goshe M B. An enhanced protein crosslink identification strategy using CID-cleavable chemical crosslinkers and LC/MS(n) analysis. Proteomics. 2012; 12(3):401-5.

Lombard D. B., Alt F. W., Cheng H. L., Bunkenborg J., Streeper R. S., Mostoslavsky R., Kim J., Yancopoulos G., Valenzuela D., Murphy A., Yang Y., Chen Y., Hirschey M. D., Bronson R. T., Haigis M., Guarente L. P., Farese R. V., Jr., Weissman S., Verdin E., Schwer B. (2007) Mammalian Sir2 homolog SIRT3 regulates global mitochondrial lysine acetylation. Mol. Cell. Biol. 27, 8807-8814.

Lopes C T, Franz M, Kazi F, Donaldson S L, Morris Q, Bader G D. Cytoscape Web: an interactive web-based network browser. Bioinformatics. 2010; 26 (18):2347-8.

Lv J., Liu H., Wang Q., Tang Z., Hou L., Zhang B. (2003) Molecular cloning of a novel human gene encoding histone acetyltransferase-like protein involved in transcriptional activation of hTERT. Biochem. Biophys. Res. Commun. 311, 506-513.

Maiolica A, Cittaro D, Borsotti D, Sennels L, Ciferri C, Tarricone C, Musacchio A, Rappsilber J. Structural analysis of multiprotein complexes by cross-linking, mass spectrometry, and database searching. Mol Cell Proteomics. 2007; 6(12):2200-11.

Merrifield R B. Solid-phase peptide synthesis. 3. An improved synthesis of bradykinin. Biochemistry. 1964; 3:1385-90.

Minami Y., Kawasaki H., Miyata Y., Suzuki K., Yahara I. (1991) Analysis of native forms and isoform compositions of the mouse 90-kDa heat shock protein, HSP90. J. Biol. Chem. 266, 10099-10103.

Muller M Q, Zeiser J J, Dreiocker F, Pich A, Schafer M, Sinz A. A universal matrix-assisted laser desorption/ionization cleavable cross-linker for protein structure analysis. Rapid Commun Mass Spectrom. 2011; 25 (1):155-61.

Muller D R, Schindler P, Towbin H, Wirth U, Voshol H, Hoving S, Steinmetz M O. Isotope-tagged cross-linking reagents. A new tool in mass spectrometric protein interaction analysis. Analytical chemistry. 2001; 73 (9):1927-34.

Nemoto T., Sato N. (1998) Oligomeric forms of the 90-kDa heat shock protein. Biochem. J. 330 (Pt 2), 989-995.

Nesvizhskii A I, Keller A, Kolker E, Aebersold R. A statistical model for identifying proteins by tandem mass spectrometry. Anal Chem. 2003; 75(17):4646-58.

Oeffinger M. (2012) Two steps forward—one step back: advances in affinity purification mass spectrometry of macromolecular complexes. Proteomics 12, 1591-1608.

Osman C., Merkwirth C., Langer T. (2009) Prohibitins and the functional compartmentalization of mitochondrial membranes. J. Cell Sci. 122, 3823-3830.

Paramelle D, Miralles G, Subra G, Martinez J. Chemical cross-linkers for protein structure studies by mass spectrometry. Proteomics. 2012; 13:438-56.

Pearl L. H., Prodromou C. (2006) Structure and mechanism of the Hsp90 molecular chaperone machinery. Annu. Rev. Biochem. 75, 271-294.

Peng K., Radivojac P., Vucetic S., Dunker A. K., Obradovic Z. (2006) Length-dependent prediction of protein intrinsic disorder. BMC Bioinformatics 7, 208.

Perdew G. H., Hord N., Hollenback C. E., Welsh M. J. (1993) Localization and characterization of the 86- and 84-kDa heat shock proteins in Hepa 1c1c7 cells. Exp. Cell Res. 209, 350-356.

Petrotchenko E V, Xiao K, Cable J, Chen Y, Dokholyan N V, Borchers C H. BiPS, a photocleavable, isotopically coded, fluorescent cross-linker for structural proteomics. Mol Cell Proteomics. 2009; 8 (2):273-86.

Politz O., Gratchev A., McCourt P. A., Schledzewski K., Guillot P., Johansson S., Svineng G., Franke P., Kannicht C., Kzhyshkowska J., Longati P., Velten F. W., Goerdt S. (2002) Stabilin-1 and -2 constitute a novel family of fasciclin-like hyaluronan receptor homologues. Biochem. J. 362, 155-164.

Rappsilber J, Siniossoglou S, Hurt E C, Mann M. A generic strategy to analyze the spatial organization of multiprotein complexes by cross-linking and mass spectrometry. Anal Chem. 2000; 72(2):267-75.

Rinner O, Seebacher J, Walzthoeni T, Mueller L N, Beck M, Schmidt A, Mueller M, Aebersold R. Identification of cross-linked peptides from large sequence databases. Nat Methods. 2008; 5 (4):315-8.

Robinson K E, Reardon P N, Spicer L D. In-cell NMR spectroscopy in *Escherichia coli*. Methods Mol Biol. 2012; 831:261-77.

Roca J., Wang J. C. (1994) DNA transport by a type II DNA topoisomerase: evidence in favor of a two-gate mechanism. Cell 77, 609-616.

Schneidman-Duhovny D., Inbar Y., Nussinov R., Wolfson H. J. (2005) PatchDock and SymmDock: servers for rigid and symmetric docking. Nucleic Acids Res. 33, W363-367.

Schwikowski B., Uetz P., Fields S. (2000) A network of protein-protein interactions in yeast. Nat. Biotechnol. 18, 1257-1261.

Scroggins B. T., Robzyk K., Wang D., Marcu M. G., Tsutsumi S., Beebe K., Cotter R. J., Felts S., Toft D., Karnitz L., Rosen N., Neckers L. (2007) An acetylation site in the middle domain of Hsp90 regulates chaperone function. Mol. Cell 25, 151-159.

Serpa J. J., Parker C. E., Petrotchenko E. V., Han J., Pan J., Borchers C. H. (2012) Mass spectrometry-based structural proteomics. Eur. J. Mass Spectr. 18, 251-267.

Shogren-Knaak M., Ishii H., Sun J. M., Pazin M. J., Davie J. R., Peterson C. L. (2006) Histone H4-K16 acetylation controls chromatin structure and protein interactions. Science 311, 844-847.

Sieber P. A new acid-labile anchor group for the solid-phase synthesis of C-terminal peptide amides by the Fmoc method. Tetrahedron Lett. 1987; 28(19):2107-2110.

Silva R A, Hilliard G M, Fang J, Macha S, Davidson W S. A three-dimensional molecular model of lipid-free apolipoprotein A-I determined by cross-linking/mass spectrometry and sequence threading. Biochemistry. 2005; 44 (8):2759-69.

Sinz A, Wang K. Mapping spatial proximities of sulfhydryl groups in proteins using a fluorogenic cross-linker and mass spectrometry. Anal Biochem. 2004; 331 (1):27-32.

Singh P, Shaffer S A, Scherl A, Holman C, Pfuetzner R A, Larson Freeman T J, Miller S I, Hernandez P, Appel R D, Goodlett D R. Characterization of protein cross-links via mass spectrometry and an open-modification search strategy. Anal Chem. 2008; 80(22):8799-806.

Smith T. J., Schmidt T., Fang J., Wu J., Siuzdak G., Stanley C. A. (2002) The structure of apo human glutamate dehydrogenase details subunit communication and allostery. J. Mol. Biol. 318, 765-777.

Snowden A. W., Gregory P. D., Case C. C., Pabo C. O. (2002) Gene-specific targeting of H3K9 methylation is sufficient for initiating repression in vivo. Current Biol. 12, 2159-2166.

Sugase K, Dyson H J, Wright P E. Mechanism of coupled folding and binding of an intrinsically disordered protein. Nature. 2007; 447(7147):1021-5.

Swaney D L, McAlister G C, Coon J J. Decision tree-driven tandem mass spectrometry for shotgun proteomics. Nat Methods. 2008; 5(11):959-64.

Tabb D L, Vega-Montoto L, Rudnick P A, Variyath A M, Ham A J, Bunk D M, Kilpatrick L E, Billheimer D D, Blackman R K, Cardasis H L, Carr S A, Clauser K R, Jaffe J D, Kowalski K A, Neubert T A, Regnier F E, Schilling B, Tegeler T J, Wang M, Wang P, Whiteaker J R, Zimmerman L J, Fisher S J, Gibson B W, Kinsinger C R, Mesri M, Rodriguez H, Stein S E, Tempst P, Paulovich A G, Liebler D C, Spiegelman C. Repeatability and reproducibility in proteomic identifications by liquid chromatography-tandem mass spectrometry. J Proteome Res. 2010; 9(2):761-76.

Tachiwana H., Kagawa W., Osakabe A., Kawaguchi K., Shiga T., Hayashi-Takanaka Y., Kimura H., Kurumizaka H. (2010) Structural basis of instability of the nucleosome containing a testis-specific histone variant, human H3T. Proc. Natl. Acad. Sci. U.S.A. 107, 10454-10459.

Tang X, Bruce J E. Chemical cross-linking for protein-protein interaction studies. Methods Mol Biol. 2009; 492:283-93.

Tang X, Bruce J E. A new cross-linking strategy: protein interaction reporter (PIR) technology for protein-protein interaction studies. Mol Biosyst. 2011; 6(6):939-47.

Tang X, Munske G R, Siems W F, Bruce J E. Mass spectrometry identifiable cross-linking strategy for studying protein-protein interactions. Anal Chem. 2005; 77(1): 311-8.

Tang X., Yi W., Munske G. R., Adhikari D. P., Zakharova N. L., Bruce J. E. (2007) Profiling the membrane proteome of Shewanella oneidensis MR-1 with new affinity labeling probes. J. Proteome Res. 6, 724-734.

Tatsuta T., Model K., Langer T. (2005) Formation of membrane-bound ring complexes by prohibitins in mitochondria. Mol. Biol. Cell 16, 248-259.

Theiss A. L., Sitaraman S. V. (2011) The role and therapeutic potential of prohibitin in disease. Biochim. Biophys. Acta 1813, 1137-1143.

Tompa P, Fuxreiter M. Fuzzy complexes: polymorphism and structural disorder in protein-protein interactions. Trends Biochem Sci. 2008; 33(1):2-8.

Vidal M., Cusick M. E., Barabasi A. L. Interactome networks and human disease. Cell 144, 986-998.

Voorhees R M, Weixlbaumer A, Loakes D, Kelley A C, Ramakrishnan V. Insights into substrate stabilization from snapshots of the peptidyl transferase center of the intact 70S ribosome. Nat Struct Mol Biol. 2009; 16(5):528-33.

Walzthoeni T, Claassen M, Leitner A, Herzog F, Bohn S, Forster F, Beck M, Aebersold R. False discovery rate estimation for cross-linked peptides identified by mass spectrometry. Nat Methods. 2012; 9:901-3.

Weisbrod C. R., Chavez J. D., Eng J. K., Yang L., Zheng C., Bruce J. E. (2012) In vivo protein interaction network identified with novel chemical cross-linking technology. J. Proteome Res. Available at: 10.1021/pr3011638.

Whitesell L., Lindquist S. L. (2005) HSP90 and the chaperoning of cancer. Nat. Rev. Cancer 5, 761-772.

Wilson C. M., Kraft C., Duggan C., Ismail N., Crawshaw S. G., High S. (2005) Ribophorin I associates with a subset of membrane proteins after their integration at the sec61 translocon. chemistry. Biol. Chem. 280, 4195-4206.

Wilson C. M., Roebuck Q., High S. (2008) Ribophorin I regulates substrate delivery to the oligosaccharyltransferase core. Proc. Natl. Acad. Sci. U.S.A. 105, 9534-9539.

Winter A., Kämäräinen O., Hofmann A. (2007) Molecular modeling of prohibitin domains. Proteins 68, 353-362.

Wold F. (1961) The reaction of bovine serum albumin with the bifunctional reagent p,p'-difluoro-m,m'-dinitro-diphenyl-sulfone. J. Biol. Chem. 236, 106-111.

Yang T, Horejsh D R, Mahan K J, Zaluzec E J, Watson T J, Gage D A. Mapping cross-linking sites in modified proteins with mass spectrometry: an application to cross-linked hemoglobins. Anal Biochem. 1996; 242 (1):55-63.

Yang B, Wu Y J, Zhu M, Fan S B, Lin J, Zhang K, Li S, Chi H, Li Y X, Chen H F, Luo S K, Ding Y H, Wang L H, Hao Z, Xiu L Y, Chen S, Ye K, He S M, Dong M Q. Identification of cross-linked peptides from complex samples. Nat Methods. 2012; 9:904-6.

Yang L, Zheng C, Weisbrod C R, Tang X, Munske G R, Hoopmann M R, Eng J K, Bruce J E. In vivo application of photocleavable protein interaction reporter technology. J Proteome Res. 2012; 11(2):1027-41.

Young M M, Tang N, Hempel J C, Oshiro C M, Taylor E W, Kuntz I D, Gibson B W, Dollinger G. High throughput protein fold identification by using experimental constraints derived from intramolecular cross-links and mass spectrometry. Proceedings of the National Academy of Sciences of the United States of America. 2000; 97 (11):5802-6.

Yu N Y, Wagner J R, Laird M R, Melli G, Rey S, Lo R, Dao P, Sahinalp S C, Ester M, Foster L J, Brinkman F S. PSORTb 3.0: improved protein subcellular localization prediction with refined localization subcategories and predictive capabilities for all prokaryotes. Bioinformatics. 2010; 26(13):1608-15.

Zhang H, Tang X, Munske G R, Tolic N, Anderson G A, Bruce J E. Identification of protein-protein interactions and topologies in living cells with chemical cross-linking and mass spectrometry. Mol Cell Proteomics. 2009; 8(3): 409-20.

Zhang H., Tang X., Munske G. R., Zakharova N., Yang L., Zheng C., Wolff M. A., Tolic N., Anderson G. A., Shi L., Marshall M. J., Fredrickson J. K., Bruce J. E. (2008) In vivo identification of the outer membrane protein OmcA-MtrC interaction network in Shewanella oneidensis MR-1 cells using novel hydrophobic chemical cross-linkers. J. Proteome Res. 7, 1712-1720.

Zheng C, Yang L, Hoopmann M R, Eng J K, Tang X, Weisbrod C R, Bruce J E. Cross-linking measurements of in vivo protein complex topologies. Mol Cell Proteomics. 2011; 10(10):M110.006841.

Zheng C, Weisbrod C. R., Chavez J. D., Eng J. K., Sharma V., Wu X., Bruce J. E. (2012) CrossLink-DB: database and software tools for storing and visualizing protein interaction topology data. J. Proteome Res. Available at: 10.1021/pr301162j.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method for identifying at least two different interacting peptide pairs within a biological system comprising:
   (a) obtaining a sample comprising a population of cross-linked precursor peptides produced by digestion of a population of proteins cross-linked with a cleavable protein interaction reporter (PIR) cross-linker;
   (b) subjecting the sample to mass spectrometry (MS) to:
      (i) produce a population of precursor ions, and
      (ii) generate a 1° mass spectrum used to determine the charge states and masses of precursor ions within the population of precursor ions;
   (c) selecting, from within the 1° mass spectrum, a precursor ion with a charge state equal to or greater than a cutoff charge state; subjecting the selected precursor ion-to conditions under which the cleavable PIR cross-linker, if present in the selected precursor ion, is cleaved, thereby producing a population of released peptides and, if present in the selected precursor ion, cleaved reporter ions; and determining the masses of the released peptides and, if present in the selected precursor ion, cleaved reporter ions by tandem mass spectrometry ($MS^2$);
   (d) analyzing the population of released peptides to identify one or more pairs of interacting peptides, where a pair of released peptides is identified as an interacting peptide pair if the combined mass of the pair of released peptides and cleaved reporter ion, as determined by $MS^2$ in step (c), is equal to the mass of the selected precursor ion, as determined by MS in step (b)(ii); and
   (e) repeating steps (b)-(d) at least once, and until at least two different interacting peptide pairs are identified within the biological system, wherein the same cutoff charge state is used for each repetition.

2. The method of claim 1, wherein the sample comprising a population of cross-linked precursor peptides is obtained by contacting the biological system with a cleavable protein interaction reporter (PIR) cross-linker to produce cross-linked proteins, and obtaining the population of cross-linked precursor peptides therefrom.

3. The method of claim 2, further comprising purifying and digesting the cross-linked proteins to obtain the sample comprising a population of cross-linked precursor peptides.

4. The method of claim 2, wherein the biological system comprises a cell, tissue, cell lysate, blood, serum, sputum, or urine.

5. The method of claim 1, wherein the conditions under which the cleavable PIR cross-linker is cleaved comprise collision-induced dissociation (CID).

6. The method of claim 1, wherein step (d) further comprises first identifying released peptides with masses lower than partial cleavage products to create a subset of complete cleavage products, and identifying one or more pairs of interacting peptides from released peptides within the subset of complete cleavage products.

7. The method of claim 6, wherein identifying released peptides with masses lower than partial cleavage products comprises identifying released peptides with masses that are less than the mass of the corresponding precursor ion minus the mass of the reporter ion minus the mass of lysine stumps, wherein lysine stumps are residual modifications that remain on lysine residues after cleavage.

8. The method of claim 1, further comprising determining the amino acid sequences of the released peptides within the one or more pairs of interacting peptides by subjecting the released peptides within the one or more pairs of interacting peptides to conditions that cause peptide fragmentation to yield spectra that can be identified from genomic, proteomic, or other large protein sequence databases.

9. The method of claim 8, wherein the amino acid sequences of the released peptides within the one or more pairs of interacting peptides are determined by triple mass spectrometry ($MS^3$).

10. The method of claim 1, wherein the cutoff charge state is at least +3.

11. The method of claim 1, wherein the cutoff charge state is at least +4.

12. The method of claim 1, wherein the cleavable PIR cross-linker comprises formula (I):

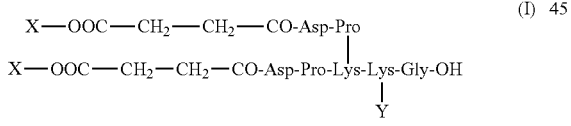

(SEQ ID NO: 27) wherein X is H, succinimid-N-yl, or phthalimid-N-yl; and Y is H or a capture moiety.

13. The method of claim 12, wherein the capture moiety is biotin, a hemagglutinin (HA) tag, or a polyhistidine tag.

14. The method of claim 12, wherein the cleavage condition is collision-induced dissociation (CID).

15. A method of identifying a candidate compound for treating cancer comprising:
(a) contacting a peptide pair from the group consisting of:

(i)
                                  (SEQ ID NO: 1)
FYEQFSKNIK, (SEQ ID NO: 1)
FYEQFSKNIK;

(ii)
                                  (SEQ ID NO: 2)
FYEAFSKNLK, (SEQ ID NO: 2)
FYEAFSKNLK;

(iii)
                                  (SEQ ID NO: 1)
FYEQFSKNIK), (SEQ ID NO: 2)
FYEAFSKNLK;

(iv)
                                  (SEQ ID NO: 1)
FYEQFSKNIK, (SEQ ID NO: 3)
KHLEINPDHPIVETLR;

(v)
                                  (SEQ ID NO: 4)
APFDLFENKK, (SEQ ID NO: 1)
FYEQFSKNIK;

(vi)
                                  (SEQ ID NO: 1)
FYEQFSKNIK, (SEQ ID NO: 5)
KAAALEAMK;
and (vii)
                                  (SEQ ID NO: 2)
FYEAFSKNLK, (SEQ ID NO: 5)
KAAALEAMK;

with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating cancer.

16. A method of identifying a candidate compound for treating an antibiotic-resistant infection comprising:
(a) contacting a peptide pair comprising KINLYGNALSR (SEQ ID NO: 6) and NDIAPYLGFGFAPKINK (SEQ ID NO: 7) with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating an antibiotic-resistant infection.

17. A method of identifying a candidate compound for treating *A. baumannii* infection comprising:

(a) contacting a peptide pair from the group consisting of:

(i)
VFFDTNKSNIKDQYKPEIAK, (SEQ ID NO: 8)

MSAAEAVKEK; (SEQ ID NO: 9)

(ii)
TKEGR, (SEQ ID NO: 10)

MSAAEAVKEK; (SEQ ID NO: 9)
and (iii)
LSTQGFAWDQPIADNKTK, (SEQ ID NO: 11)

MSAAEAVKEK; (SEQ ID NO: 9)

with a plurality of test compounds under conditions suitable for binding of one member of the peptide pair to the other member of the peptide pair; and (b) identifying a test compound that reduces binding of one member of the peptide pair to the other member of the peptide pair relative to a control, wherein the identified test compound is a candidate compound for treating *A. baumannii* infection.

18. The method of claim 1, wherein the MS of step (b) is performed on the sample as it elutes from a liquid chromatography (LC) column.

19. The method of claim 1, wherein steps (b)-(d) are repeated at least 10 times.

20. The method of claim 1, wherein steps (b)-(d) are repeated at least 50 times.

21. The method of claim 1, wherein the same precursor ion is selected in no more than two repetitions of steps (b)-(d).

22. The method of claim 1, wherein a different precursor ion is selected each time steps (b)-(d) are repeated.

* * * * *

SEQUENCE LISTING

```
<160> NUMBER OF SEQ ID NOS: 44

<210> SEQ ID NO 1
<211> LENGTH: 10
<212> TYPE: PRT
```

```
<213> ORGANISM: Artificial Sequence
<220> FEATURE:
<223> OTHER INFORMATION: Synthetic

<400> SEQUENCE: 1

Phe Tyr Glu Gln Phe Ser Lys Asn Ile Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Phe Tyr Glu Ala Phe Ser Lys Asn Leu Lys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic

<400> SEQUENCE: 3

Lys His Leu Glu Ile Asn Pro Asp His Pro Ile Val Glu Thr Leu Arg
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Ala Pro Phe Asp Leu Phe Glu Asn Lys Lys
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Lys Ala Ala Ala Leu Glu Ala Met Lys
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Lys Ile Asn Leu Tyr Gly Asn Ala Leu Ser Arg
1               5                   10

<210> SEQ ID NO 7
<211> LENGTH: 17
<212> TYPE: PRT
<213> ORGANISM: Artificial Sequence
```

```
<220> FEATURE:
<223> OTHER INFORMATION: Synthetic

<400> SEQUENCE: 7

Asn Asp Ile Ala Pro Tyr Leu Gly Phe Gly Phe Ala Pro Lys Ile Asn
1               5                   10                  15

Lys

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Val Phe Phe Asp Thr Asn Lys Ser Asn Ile Lys Asp Gln Tyr Lys Pro
1               5                   10                  15

Glu Ile Ala Lys
            20

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Met Ser Ala Ala Glu Ala Val Lys Glu Lys
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Thr Lys Glu Gly Arg
1               5

<210> SEQ ID NO 11
<211> LENGTH: 18
<212> TYPE: PRT
<213> ORGANISM: Artificial Sequence
<220> FEATURE:
<223> OTHER INFORMATION: Synthetic

<400> SEQUENCE: 11

Leu Ser Thr Gln Gly Phe Ala Trp Asp Gln Pro Ile Ala Asp Asn Lys
1               5                   10                  15

Thr Lys

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Lys Gly Asn Gly Lys Ser Ser Asp Pro Ala Gly Ser Phe Arg Val
1               5                   10                  15
```

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Glu Thr Ala Ala Ala Lys Phe Glu Arg
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Asn Leu Thr Lys Asp Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

His Phe Thr Ala Lys Leu Lys
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic

<400> SEQUENCE: 16

Gly Leu Thr Phe Thr Tyr Glu Pro Lys Val Leu Arg
1               5                   10

<210> SEQ ID NO 17
<211> LENGTH: 79
<212> TYPE: PRT
<213> ORGANISM: Artificial Sequence
<220> FEATURE:
<223> OTHER INFORMATION: Synthetic

<400> SEQUENCE: 17

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ala Pro Ala Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys
65                  70                  75

```
<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Lys Ser Thr Gly Gly Lys Ala Pro Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Lys Gln Leu Ala Thr Lys
1               5

<210> SEQ ID NO 20
<211> LENGTH: 854
<212> TYPE: PRT
<213> ORGANISM: Homo sapiens

<400> SEQUENCE: 20

Met Pro Pro Cys Ser Gly Gly Asp Gly Ser Thr Pro Pro Gly Pro Ser
1               5                   10                  15

Leu Arg Asp Arg Asp Cys Pro Ala Gln Ser Ala Glu Tyr Pro Arg Asp
                20                  25                  30

Arg Leu Asp Pro Arg Pro Gly Ser Pro Ser Glu Ala Ser Ser Pro Pro
            35                  40                  45

Phe Leu Arg Ser Arg Ala Pro Val Asn Trp Tyr Gln Glu Lys Ala Gln
    50                  55                  60

Val Phe Leu Trp His Leu Leu Val Ser Gly Ser Thr Thr Leu Leu Cys
65                  70                  75                  80

Leu Trp Lys Gln Pro Phe His Val Ser Ala Phe Pro Val Thr Ala Ser
                85                  90                  95

Leu Ala Phe Arg Gln Ser Gln Gly Ala Gly Gln His Leu Tyr Lys Asp
                100                 105                 110

Leu Gln Pro Phe Ile Leu Leu Arg Leu Leu Met Pro Glu Glu Thr Gln
            115                 120                 125

Thr Gln Asp Gln Pro Met Glu Glu Glu Val Glu Thr Phe Ala Phe
            130                 135                 140

Gln Ala Glu Ile Ala Gln Leu Met Ser Leu Ile Ile Asn Thr Phe Tyr
145                 150                 155                 160

Ser Asn Lys Glu Ile Phe Leu Arg Glu Leu Ile Ser Asn Ser Ser Asp
                165                 170                 175

Ala Leu Asp Lys Ile Arg Tyr Glu Ser Leu Thr Asp Pro Ser Lys Leu
                180                 185                 190

Asp Ser Gly Arg Glu Leu His Ile Asn Leu Ile Pro Asn Lys Gln Gly
            195                 200                 205

Arg Thr Leu Thr Ile Val Asp Thr Gly Ile Gly Met Thr Lys Ala Asp
            210                 215                 220

Leu Ile Asn Asn Leu Gly Thr Ile Ala Lys Ser Gly Thr Lys Ala Phe
225                 230                 235                 240

Met Glu Ala Leu Gln Ala Gly Ala Asp Ile Ser Met Ile Gly Gln Phe
```

```
            245                 250                 255
Gly Val Gly Phe Tyr Ser Ala Tyr Leu Val Ala Glu Lys Val Thr Val
            260                 265                 270
Ile Thr Lys His Asn Asp Asp Glu Gln Tyr Ala Trp Glu Ser Ser Ala
            275                 280                 285
Gly Gly Ser Phe Thr Val Arg Thr Asp Thr Gly Glu Pro Met Gly Arg
            290                 295                 300
Gly Thr Lys Val Ile Leu His Leu Lys Glu Asp Gln Thr Glu Tyr Leu
305                 310                 315                 320
Glu Glu Arg Arg Ile Lys Glu Ile Val Lys Lys His Ser Gln Phe Ile
            325                 330                 335
Gly Tyr Pro Ile Thr Leu Phe Val Glu Lys Glu Arg Asp Lys Glu Val
            340                 345                 350
Ser Asp Asp Glu Ala Glu Glu Lys Glu Asp Lys Glu Glu Glu Lys Glu
            355                 360                 365
Lys Glu Glu Lys Glu Ser Glu Asp Lys Pro Glu Ile Glu Asp Val Gly
            370                 375                 380
Ser Asp Glu Glu Glu Glu Lys Lys Asp Gly Asp Lys Lys Lys Lys Lys
385                 390                 395                 400
Lys Ile Lys Glu Lys Tyr Ile Asp Gln Glu Glu Leu Asn Lys Thr Lys
            405                 410                 415
Pro Ile Trp Thr Arg Asn Pro Asp Asp Ile Thr Asn Glu Glu Tyr Gly
            420                 425                 430
Glu Phe Tyr Lys Ser Leu Thr Asn Asp Trp Glu Asp His Leu Ala Val
            435                 440                 445
Lys His Phe Ser Val Glu Gly Gln Leu Glu Phe Arg Ala Leu Leu Phe
            450                 455                 460
Val Pro Arg Arg Ala Pro Phe Asp Leu Phe Glu Asn Arg Lys Lys Lys
465                 470                 475                 480
Asn Asn Ile Lys Leu Tyr Val Arg Arg Val Phe Ile Met Asp Asn Cys
            485                 490                 495
Glu Glu Leu Ile Pro Glu Tyr Leu Asn Phe Ile Arg Gly Val Val Asp
            500                 505                 510
Ser Glu Asp Leu Pro Leu Asn Ile Ser Arg Glu Met Leu Gln Gln Ser
            515                 520                 525
Lys Ile Leu Lys Val Ile Arg Lys Asn Leu Val Lys Lys Cys Leu Glu
            530                 535                 540
Leu Phe Thr Glu Leu Ala Glu Asp Lys Glu Asn Tyr Lys Lys Phe Tyr
545                 550                 555                 560
Glu Gln Phe Ser Lys Asn Ile Lys Leu Gly Ile His Glu Asp Ser Gln
            565                 570                 575
Asn Arg Lys Lys Leu Ser Glu Leu Leu Arg Tyr Tyr Thr Ser Ala Ser
            580                 585                 590
Gly Asp Glu Met Val Ser Leu Lys Asp Tyr Cys Thr Arg Met Lys Glu
            595                 600                 605
Asn Gln Lys His Ile Tyr Tyr Ile Thr Gly Glu Thr Lys Asp Gln Val
            610                 615                 620
Ala Asn Ser Ala Phe Val Glu Arg Leu Arg Lys His Gly Leu Glu Val
625                 630                 635                 640
Ile Tyr Met Ile Glu Pro Ile Asp Glu Tyr Cys Val Gln Gln Leu Lys
            645                 650                 655
Glu Phe Glu Gly Lys Thr Leu Val Ser Val Thr Lys Glu Gly Leu Glu
            660                 665                 670
```

```
Leu Pro Glu Asp Glu Glu Lys Lys Gln Glu Lys Lys Thr
        675                 680                 685

Lys Phe Glu Asn Leu Cys Lys Ile Met Lys Asp Ile Leu Glu Lys Lys
            690                 695                 700

Val Glu Lys Val Val Ser Asn Arg Leu Val Thr Ser Pro Cys Cys
705                 710                 715                 720

Ile Val Thr Ser Thr Tyr Gly Trp Thr Ala Asn Met Glu Arg Ile Met
                725                 730                 735

Lys Ala Gln Ala Leu Arg Asp Asn Ser Thr Met Gly Tyr Met Ala Ala
            740                 745                 750

Lys Lys His Leu Glu Ile Asn Pro Asp His Ser Ile Ile Glu Thr Leu
            755                 760                 765

Arg Gln Lys Ala Glu Ala Asp Lys Asn Asp Lys Ser Val Lys Asp Leu
            770                 775                 780

Val Ile Leu Leu Tyr Glu Thr Ala Leu Leu Ser Ser Gly Phe Ser Leu
785                 790                 795                 800

Glu Asp Pro Gln Thr His Ala Asn Arg Ile Tyr Arg Met Ile Lys Leu
                805                 810                 815

Gly Leu Gly Ile Asp Glu Asp Pro Thr Ala Asp Asp Thr Ser Ala
            820                 825                 830

Ala Val Thr Glu Glu Met Pro Pro Leu Glu Gly Asp Asp Thr Ser
            835                 840                 845

Arg Met Glu Glu Val Asp
    850

<210> SEQ ID NO 21
<211> LENGTH: 724
<212> TYPE: PRT
<213> ORGANISM: Homo sapiens

<400> SEQUENCE: 21

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
            20                  25                  30

Tyr Ser Asn Lys Glu Ile Phe Leu Arg Glu Leu Ile Ser Asn Ala Ser
        35                  40                  45

Asp Ala Leu Asp Lys Ile Arg Tyr Glu Ser Leu Thr Asp Pro Ser Lys
    50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
```

```
                180             185             190
Leu Glu Glu Arg Arg Val Lys Glu Val Val Lys Lys His Ser Gln Phe
            195                 200                 205
Ile Gly Tyr Pro Ile Thr Leu Tyr Leu Glu Lys Glu Arg Glu Lys Glu
            210                 215                 220
Ile Ser Asp Asp Glu Ala Glu Glu Lys Gly Glu Lys Glu Glu
225                 230                 235                 240
Asp Lys Asp Asp Glu Glu Lys Pro Lys Ile Glu Asp Val Gly Ser Asp
                245                 250                 255
Glu Glu Asp Asp Ser Gly Lys Asp Lys Lys Lys Thr Lys Lys Ile
                260                 265                 270
Lys Glu Lys Tyr Ile Asp Gln Glu Glu Leu Asn Lys Thr Lys Pro Ile
            275                 280                 285
Trp Thr Arg Asn Pro Asp Asp Ile Thr Gln Glu Glu Tyr Gly Glu Phe
            290                 295                 300
Tyr Lys Ser Leu Thr Asn Asp Trp Glu Asp His Leu Ala Val Lys His
305                 310                 315                 320
Phe Ser Val Glu Gly Gln Leu Glu Phe Arg Ala Leu Leu Phe Ile Pro
                325                 330                 335
Arg Arg Ala Pro Phe Asp Leu Phe Glu Asn Lys Lys Lys Lys Asn Asn
                340                 345                 350
Ile Lys Leu Tyr Val Arg Arg Val Phe Ile Met Asp Ser Cys Asp Glu
            355                 360                 365
Leu Ile Pro Glu Tyr Leu Asn Phe Ile Arg Gly Val Val Asp Ser Glu
            370                 375                 380
Asp Leu Pro Leu Asn Ile Ser Arg Glu Met Leu Gln Gln Ser Lys Ile
385                 390                 395                 400
Leu Lys Val Ile Arg Lys Asn Ile Val Lys Lys Cys Leu Glu Leu Phe
                405                 410                 415
Ser Glu Leu Ala Glu Asp Lys Glu Asn Tyr Lys Lys Phe Tyr Glu Ala
                420                 425                 430
Phe Ser Lys Asn Leu Lys Leu Gly Ile His Glu Asp Ser Thr Asn Arg
            435                 440                 445
Arg Arg Leu Ser Glu Leu Leu Arg Tyr His Thr Ser Gln Ser Gly Asp
            450                 455                 460
Glu Met Thr Ser Leu Ser Glu Tyr Val Ser Arg Met Lys Glu Thr Gln
465                 470                 475                 480
Lys Ser Ile Tyr Tyr Ile Thr Gly Glu Ser Lys Glu Gln Val Ala Asn
                485                 490                 495
Ser Ala Phe Val Glu Arg Val Arg Lys Arg Gly Phe Glu Val Val Tyr
            500                 505                 510
Met Thr Glu Pro Ile Asp Glu Tyr Cys Val Gln Gln Leu Lys Glu Phe
            515                 520                 525
Asp Gly Lys Ser Leu Val Ser Val Thr Lys Glu Gly Leu Glu Leu Pro
            530                 535                 540
Glu Asp Glu Glu Glu Lys Lys Lys Met Glu Glu Ser Lys Ala Lys Phe
545                 550                 555                 560
Glu Asn Leu Cys Lys Leu Met Lys Glu Ile Leu Asp Lys Lys Val Glu
                565                 570                 575
Lys Val Thr Ile Ser Asn Arg Leu Val Ser Ser Pro Cys Cys Ile Val
            580                 585                 590
Thr Ser Thr Tyr Gly Trp Thr Ala Asn Met Glu Arg Ile Met Lys Ala
            595                 600                 605
```

```
Gln Ala Leu Arg Asp Asn Ser Thr Met Gly Tyr Met Met Ala Lys Lys
            610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
                675                 680                 685

Gly Ile Asp Glu Asp Glu Val Ala Ala Glu Pro Asn Ala Ala Val
690                 695                 700

Pro Asp Glu Ile Pro Pro Leu Glu Gly Asp Glu Asp Ala Ser Arg Met
705                 710                 715                 720

Glu Glu Val Asp

<210> SEQ ID NO 22
<211> LENGTH: 590
<212> TYPE: PRT
<213> ORGANISM: Homo sapiens

<400> SEQUENCE: 22

Met Glu Ser Gly Ser Pro Met Gly Glu Val Glu Ile Ser Arg Thr Ile
1               5                   10                  15

Arg Thr Asn Gly Arg Gly Gln Arg Gly Tyr Asp Trp Gln Cys Lys Arg
            20                  25                  30

Pro Ile Arg Val Ala Glu Val Arg Ser Ser Leu His Ser Trp Ser Leu
        35                  40                  45

Arg Trp Val Asn Glu Leu Lys Glu Lys Gly Asn Lys Ala Leu Ser Val
    50                  55                  60

Gly Asn Ile Asp Asp Ala Leu Gln Cys Tyr Ser Glu Ala Ile Lys Leu
65                  70                  75                  80

Asp Pro His Asn His Val Leu Tyr Ser Asn Arg Ser Ala Ala Tyr Ala
                85                  90                  95

Lys Lys Gly Asp Tyr Gln Lys Ala Tyr Glu Asp Gly Cys Lys Thr Val
            100                 105                 110

Asp Leu Lys Pro Asp Trp Gly Lys Gly Tyr Ser Arg Lys Ala Ala Ala
        115                 120                 125

Leu Glu Leu Leu Asn Arg Phe Glu Glu Ala Lys Arg Thr Tyr Glu Glu
    130                 135                 140

Gly Leu Lys His Glu Ala Asn Asn Pro Gln Leu Lys Glu Gly Leu Gln
145                 150                 155                 160

Asn Met Glu Ala Arg Leu Ala Glu Arg Lys Phe Met Asn Pro Phe Asn
                165                 170                 175

Met Pro Asn Leu Tyr Gln Lys Leu Glu Ser Asp Pro Arg Thr Arg Thr
            180                 185                 190

Leu Leu Ser Asp Pro Thr Tyr Arg Glu Leu Ile Glu Gln Leu Arg Asn
        195                 200                 205

Lys Pro Ser Asp Leu Gly Thr Lys Leu Gln Asp Pro Arg Ile Met Thr
    210                 215                 220

Thr Leu Ser Val Leu Leu Gly Val Asp Leu Gly Ser Met Asp Glu Glu
225                 230                 235                 240

Glu Glu Ile Ala Thr Pro Pro Pro Pro Pro Lys Lys Glu Thr
                245                 250                 255
```

Lys Pro Glu Pro Met Glu Glu Asp Leu Pro Glu Asn Lys Lys Gln Ala
            260                 265                 270

Leu Lys Glu Lys Glu Leu Gly Asn Asp Ala Tyr Lys Lys Lys Asp Phe
        275                 280                 285

Asp Thr Ala Leu Lys His Tyr Asp Lys Ala Lys Glu Leu Asp Pro Thr
    290                 295                 300

Asn Met Thr Tyr Ile Thr Asn Gln Ala Ala Val Tyr Phe Glu Lys Gly
305                 310                 315                 320

Asp Tyr Asn Lys Cys Arg Glu Leu Cys Glu Lys Ala Ile Glu Val Gly
                325                 330                 335

Arg Glu Asn Arg Glu Asp Tyr Arg Gln Ile Ala Lys Ala Tyr Ala Arg
            340                 345                 350

Ile Gly Asn Ser Tyr Phe Lys Glu Lys Tyr Lys Asp Ala Ile His
        355                 360                 365

Phe Tyr Asn Lys Ser Leu Ala Glu His Arg Thr Pro Asp Val Leu Lys
    370                 375                 380

Lys Cys Gln Gln Ala Glu Lys Ile Leu Lys Glu Gln Glu Arg Leu Ala
385                 390                 395                 400

Tyr Ile Asn Pro Asp Leu Ala Leu Glu Glu Lys Asn Lys Gly Asn Glu
                405                 410                 415

Cys Phe Gln Lys Gly Asp Tyr Pro Gln Ala Met Lys His Tyr Thr Glu
            420                 425                 430

Ala Ile Lys Arg Asn Pro Lys Asp Ala Lys Leu Tyr Ser Asn Arg Ala
        435                 440                 445

Ala Cys Tyr Thr Lys Leu Leu Glu Phe Gln Leu Ala Leu Lys Asp Cys
    450                 455                 460

Glu Glu Cys Ile Gln Leu Glu Pro Thr Phe Ile Lys Gly Tyr Thr Arg
465                 470                 475                 480

Lys Ala Ala Ala Leu Glu Ala Met Lys Asp Tyr Thr Lys Ala Met Asp
                485                 490                 495

Val Tyr Gln Lys Ala Leu Asp Leu Asp Ser Ser Cys Lys Glu Ala Ala
            500                 505                 510

Asp Gly Tyr Gln Arg Cys Met Met Ala Gln Tyr Asn Arg His Asp Ser
        515                 520                 525

Pro Glu Asp Val Lys Arg Arg Ala Met Ala Asp Pro Glu Val Gln Gln
    530                 535                 540

Ile Met Ser Asp Pro Ala Met Arg Leu Ile Leu Glu Gln Met Gln Lys
545                 550                 555                 560

Asp Pro Gln Ala Leu Ser Glu His Leu Lys Asn Pro Val Ile Ala Gln
                565                 570                 575

Lys Ile Gln Lys Leu Met Asp Val Gly Leu Ile Ala Ile Arg
            580                 585                 590

<210> SEQ ID NO 23
<211> LENGTH: 273
<212> TYPE: PRT
<213> ORGANISM: Acinetobacter baumannii

<400> SEQUENCE: 23

Met Asn Lys Tyr Phe Thr Cys Tyr Val Val Ala Ser Leu Phe Leu Ser
1               5                   10                  15

Gly Cys Thr Val Gln His Asn Leu Ile Asn Glu Thr Pro Ser Gln Ile
            20                  25                  30

Val Gln Gly His Asn Gln Val Ile His Gln Tyr Phe Asp Glu Lys Asn

```
                35                  40                  45
Thr Ser Gly Val Leu Val Ile Gln Thr Asp Lys Lys Ile Asn Leu Tyr
 50                  55                  60

Gly Asn Ala Leu Ser Arg Ala Asn Thr Glu Tyr Val Pro Ala Ser Thr
 65                  70                  75                  80

Phe Lys Met Leu Asn Ala Leu Ile Gly Leu Glu Asn Gln Lys Thr Asp
                 85                  90                  95

Ile Asn Glu Ile Phe Lys Trp Lys Gly Glu Lys Arg Ser Phe Thr Ala
                100                 105                 110

Trp Glu Lys Asp Met Thr Leu Gly Glu Ala Met Lys Leu Ser Ala Val
                115                 120                 125

Pro Val Tyr Gln Glu Leu Ala Arg Arg Ile Gly Leu Asp Leu Met Gln
130                 135                 140

Lys Glu Val Lys Arg Ile Gly Phe Gly Asn Ala Glu Ile Gly Gln Gln
145                 150                 155                 160

Val Asp Asn Phe Trp Leu Val Gly Pro Leu Lys Val Thr Pro Ile Gln
                165                 170                 175

Glu Val Glu Phe Val Ser Gln Leu Ala His Thr Gln Leu Pro Phe Ser
                180                 185                 190

Glu Lys Val Gln Ala Asn Val Lys Asn Met Leu Leu Leu Glu Glu Ser
                195                 200                 205

Asn Gly Tyr Lys Ile Phe Gly Lys Thr Gly Trp Ala Met Asp Ile Lys
210                 215                 220

Pro Gln Val Gly Trp Leu Thr Gly Trp Val Glu Gln Pro Asp Gly Lys
225                 230                 235                 240

Ile Val Ala Phe Ala Leu Asn Met Glu Met Arg Ser Glu Met Pro Ala
                245                 250                 255

Ser Ile Arg Asn Glu Leu Leu Met Lys Ser Leu Lys Gln Leu Asn Ile
                260                 265                 270

Ile
```

<210> SEQ ID NO 24
<211> LENGTH: 246
<212> TYPE: PRT
<213> ORGANISM: Acinetobacter baumannii

<400> SEQUENCE: 24

```
Met Lys Val Leu Arg Val Leu Val Thr Thr Thr Ala Leu Leu Ala Ala
 1               5                  10                  15

Gly Ala Ala Met Ala Asp Glu Val Val His Asp Ser Tyr Ala Phe
                 20                  25                  30

Asp Lys Asn Gln Leu Ile Pro Val Gly Ala Arg Ala Glu Val Gly Thr
                 35                  40                  45

Thr Gly Tyr Gly Gly Ala Leu Leu Trp Gln Ala Asn Pro Tyr Val Gly
 50                  55                  60

Leu Ala Leu Gly Tyr Asn Gly Gly Asp Ile Ser Trp Ser Asp Asp Val
 65                  70                  75                  80

Lys Val Asn Gly Ser Thr Tyr Asp Leu Asp Met Asp Asn Asn Asn Val
                 85                  90                  95

Tyr Leu Asn Ala Glu Ile Arg Pro Trp Gly Ala Ser Thr Asn Arg Trp
                100                 105                 110

Ala Gln Gly Leu Tyr Val Ala Ala Gly Ala Ala Tyr Leu Asp Asn Asp
                115                 120                 125

Tyr Asp Leu Thr Arg Asn Val Asp Ala Thr Arg Ser Phe Arg Val Asn
```

```
                130             135             140
Asn Gln Asp Phe Ile Ala Gly Ala Asp Gly Val Lys Ile Asn Gly Gln
145                 150                 155                 160

Met Ser Tyr Lys Asn Asp Ile Ala Pro Tyr Leu Gly Phe Gly Phe Ala
                165                 170                 175

Pro Lys Ile Asn Lys Asn Trp Gly Val Phe Gly Glu Val Gly Ala Tyr
                180                 185                 190

Tyr Thr Gly Asn Pro Thr Val Lys Leu Val Ser Ser Gly Ser Ala Val
                195                 200                 205

Thr Thr Gly Asp Gln Ser Leu Glu Glu Ala Val Asn Ala Glu Ala Arg
                210                 215                 220

Lys Ile Ala Asn Asp Asp Lys Tyr Lys Trp Leu Pro Val Gly Lys Val
225                 230                 235                 240

Gly Val Asn Phe Phe Trp
                245

<210> SEQ ID NO 25
<211> LENGTH: 356
<212> TYPE: PRT
<213> ORGANISM: Acinetobacter baumannii

<400> SEQUENCE: 25

Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Ser Gln His Asn Asn Gly Gly Lys Asp Gly Asn
                35                  40                  45

Leu Thr Asn Gly Pro Glu Leu Gln Asp Asp Leu Phe Val Gly Ala Ala
                50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Ala Ser Ala Gly Ala Glu Tyr Lys
                85                  90                  95

Gln Lys Gln Ile Asn Gly Asn Phe Tyr Val Thr Ser Asp Leu Ile Thr
                100                 105                 110

Lys Asn Tyr Asp Ser Lys Ile Lys Pro Tyr Val Leu Leu Gly Ala Gly
                115                 120                 125

His Tyr Lys Tyr Asp Phe Asp Gly Val Asn Arg Gly Thr Arg Gly Thr
                130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
                180                 185                 190

Val Leu Gly Gly His Leu Lys Pro Ala Ala Pro Val Val Glu Val Ala
                195                 200                 205

Pro Val Glu Pro Thr Pro Val Ala Pro Gln Pro Gln Glu Leu Thr Glu
                210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255
```

-continued

```
Ser Glu Tyr Pro Asn Ala Thr Ala Arg Ile Glu Gly His Thr Asp Asn
            260                 265                 270

Thr Gly Pro Arg Lys Leu Asn Glu Arg Leu Ser Leu Ala Arg Ala Asn
        275                 280                 285

Ser Val Lys Ser Ala Leu Val Asn Glu Tyr Asn Val Asp Ala Ser Arg
    290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr Val Val Gln Pro Gly Gln Glu Ala Ala Ala Pro
            340                 345                 350

Ala Ala Ala Gln
        355

<210> SEQ ID NO 26
<211> LENGTH: 2871
<212> TYPE: PRT
<213> ORGANISM: Homo sapiens

<400> SEQUENCE: 26

Met Ser Cys Asn Gly Gly Ser His Pro Arg Ile Asn Thr Leu Gly Arg
1               5                   10                  15

Met Ile Arg Ala Glu Ser Gly Pro Asp Leu Arg Tyr Glu Val Thr Ser
            20                  25                  30

Gly Gly Gly Gly Thr Ser Arg Met Tyr Tyr Ser Arg Arg Gly Val Ile
        35                  40                  45

Thr Asp Gln Asn Ser Asp Gly Tyr Cys Gln Thr Gly Thr Met Ser Arg
    50                  55                  60

His Gln Asn Gln Asn Thr Ile Gln Glu Leu Leu Gln Asn Cys Ser Asp
65                  70                  75                  80

Cys Leu Met Arg Ala Glu Leu Ile Val Gln Pro Glu Leu Lys Tyr Gly
                85                  90                  95

Asp Gly Ile Gln Leu Thr Arg Ser Arg Glu Leu Asp Glu Cys Phe Ala
            100                 105                 110

Gln Ala Asn Asp Gln Met Glu Ile Leu Asp Ser Leu Ile Arg Glu Met
        115                 120                 125

Arg Gln Met Gly Gln Pro Cys Asp Ala Tyr Gln Lys Arg Leu Leu Gln
    130                 135                 140

Leu Gln Glu Gln Met Arg Ala Leu Tyr Lys Ala Ile Ser Val Pro Arg
145                 150                 155                 160

Val Arg Arg Ala Ser Ser Lys Gly Gly Gly Tyr Thr Cys Gln Ser
                165                 170                 175

Gly Ser Gly Trp Asp Glu Phe Thr Lys His Val Thr Ser Glu Cys Leu
            180                 185                 190

Gly Trp Met Arg Gln Gln Arg Ala Glu Met Asp Met Val Ala Trp Gly
        195                 200                 205

Val Asp Leu Ala Ser Val Glu Gln His Ile Asn Ser His Arg Gly Ile
    210                 215                 220

His Asn Ser Ile Gly Asp Tyr Arg Trp Gln Leu Asp Lys Ile Lys Ala
225                 230                 235                 240

Asp Leu Arg Glu Lys Ser Ala Ile Tyr Gln Leu Glu Glu Glu Tyr Glu
                245                 250                 255

Asn Leu Leu Lys Ala Ser Phe Glu Arg Met Asp His Leu Arg Gln Leu
            260                 265                 270
```

```
Gln Asn Ile Ile Gln Ala Thr Ser Arg Glu Ile Met Trp Ile Asn Asp
        275                 280                 285

Cys Glu Glu Glu Leu Leu Tyr Asp Trp Ser Asp Lys Asn Thr Asn
    290                 295                 300

Ile Ala Gln Lys Gln Glu Ala Phe Ser Ile Arg Met Ser Gln Leu Glu
305                 310                 315                 320

Val Lys Glu Lys Glu Leu Asn Lys Leu Lys Gln Glu Ser Asp Gln Leu
                325                 330                 335

Val Leu Asn Gln His Pro Ala Ser Asp Lys Ile Glu Ala Tyr Met Asp
        340                 345                 350

Thr Leu Gln Thr Gln Trp Ser Trp Ile Leu Gln Ile Thr Lys Cys Ile
        355                 360                 365

Asp Val His Leu Lys Glu Asn Ala Ala Tyr Phe Gln Phe Phe Glu Glu
        370                 375                 380

Ala Gln Ser Thr Glu Ala Tyr Leu Lys Gly Leu Gln Asp Ser Ile Arg
385                 390                 395                 400

Lys Lys Tyr Pro Cys Asp Lys Asn Met Pro Leu Gln His Leu Leu Glu
                405                 410                 415

Gln Ile Lys Glu Leu Glu Lys Glu Arg Glu Lys Ile Leu Glu Tyr Lys
        420                 425                 430

Arg Gln Val Gln Asn Leu Val Asn Lys Ser Lys Lys Ile Val Gln Leu
        435                 440                 445

Lys Pro Arg Asn Pro Asp Tyr Arg Ser Asn Lys Pro Ile Ile Leu Arg
        450                 455                 460

Ala Leu Cys Asp Tyr Lys Gln Asp Gln Lys Ile Val His Lys Gly Asp
465                 470                 475                 480

Glu Cys Ile Leu Lys Asp Asn Asn Glu Arg Ser Lys Trp Tyr Val Thr
                485                 490                 495

Gly Pro Gly Gly Val Asp Met Leu Val Pro Ser Val Gly Leu Ile Ile
                500                 505                 510

Pro Pro Pro Asn Pro Leu Ala Val Asp Leu Ser Cys Lys Ile Glu Gln
        515                 520                 525

Tyr Tyr Glu Ala Ile Leu Ala Leu Trp Asn Gln Leu Tyr Ile Asn Met
        530                 535                 540

Lys Ser Leu Val Ser Trp His Tyr Cys Met Ile Asp Ile Glu Lys Ile
545                 550                 555                 560

Arg Ala Met Thr Ile Ala Lys Leu Lys Thr Met Arg Gln Glu Asp Tyr
                565                 570                 575

Met Lys Thr Ile Ala Asp Leu Glu Leu His Tyr Gln Glu Phe Ile Arg
        580                 585                 590

Asn Ser Gln Gly Ser Glu Met Phe Gly Asp Asp Lys Arg Lys Ile
        595                 600                 605

Gln Ser Gln Phe Thr Asp Ala Gln Lys His Tyr Gln Thr Leu Val Ile
        610                 615                 620

Gln Leu Pro Gly Tyr Pro Gln His Gln Thr Val Thr Thr Thr Glu Ile
625                 630                 635                 640

Thr His His Gly Thr Cys Gln Asp Val Asn His Asn Lys Val Ile Glu
                645                 650                 655

Thr Asn Arg Glu Asn Asp Lys Gln Glu Thr Trp Met Leu Met Glu Leu
                660                 665                 670

Gln Lys Ile Arg Arg Gln Ile Glu His Cys Glu Gly Arg Met Thr Leu
        675                 680                 685
```

```
Lys Asn Leu Pro Leu Ala Asp Gln Gly Ser Ser His His Ile Thr Val
    690             695             700

Lys Ile Asn Glu Leu Lys Ser Val Gln Asn Asp Ser Gln Ala Ile Ala
705             710             715                 720

Glu Val Leu Asn Gln Leu Lys Asp Met Leu Ala Asn Phe Arg Gly Ser
            725             730             735

Glu Lys Tyr Cys Tyr Leu Gln Asn Glu Val Phe Gly Leu Phe Gln Lys
                740             745             750

Leu Glu Asn Ile Asn Gly Val Thr Asp Gly Tyr Leu Asn Ser Leu Cys
            755             760             765

Thr Val Arg Ala Leu Leu Gln Ala Ile Leu Gln Thr Glu Asp Met Leu
770             775             780

Lys Val Tyr Glu Ala Arg Leu Thr Glu Glu Thr Val Cys Leu Asp
785             790             795             800

Leu Asp Lys Val Glu Ala Tyr Arg Cys Gly Leu Lys Lys Ile Lys Asn
            805             810             815

Asp Leu Asn Leu Lys Lys Ser Leu Leu Ala Thr Met Lys Thr Glu Leu
        820             825             830

Gln Lys Ala Gln Gln Ile His Ser Gln Thr Ser Gln Gln Tyr Pro Leu
    835             840             845

Tyr Asp Leu Asp Leu Gly Lys Phe Gly Glu Lys Val Thr Gln Leu Thr
850             855             860

Asp Arg Trp Gln Arg Ile Asp Lys Gln Ile Asp Phe Arg Leu Trp Asp
865             870             875             880

Leu Glu Lys Gln Ile Lys Gln Leu Arg Asn Tyr Arg Asp Asn Tyr Gln
            885             890             895

Ala Phe Cys Lys Trp Leu Tyr Asp Arg Lys Arg Arg Gln Asp Ser Leu
            900             905             910

Glu Ser Met Lys Phe Gly Asp Ser Asn Thr Val Met Arg Phe Leu Asn
        915             920             925

Glu Gln Lys Asn Leu His Ser Glu Ile Ser Gly Lys Arg Asp Lys Ser
    930             935             940

Glu Glu Val Gln Lys Ile Ala Glu Leu Cys Ala Asn Ser Ile Lys Asp
945             950             955             960

Tyr Glu Leu Gln Leu Ala Ser Tyr Thr Ser Gly Leu Glu Thr Leu Leu
            965             970             975

Asn Ile Pro Ile Lys Arg Thr Met Ile Gln Ser Pro Ser Gly Val Ile
        980             985             990

Leu Gln Glu Ala Ala Asp Val His Ala Arg Tyr Ile Glu Leu Leu Thr
    995             1000            1005

Arg Ser Gly Asp Tyr Tyr Arg Phe Leu Ser Glu Met Leu Lys Ser
    1010            1015            1020

Leu Glu Asp Leu Lys Leu Lys Asn Thr Lys Ile Glu Val Leu Glu
    1025            1030            1035

Glu Glu Leu Arg Leu Ala Arg Asp Ala Asn Ser Glu Asn Cys Asn
    1040            1045            1050

Lys Asn Lys Phe Leu Asp Gln Asn Leu Gln Lys Tyr Gln Ala Glu
    1055            1060            1065

Cys Ser Gln Phe Lys Ala Lys Leu Ala Ser Leu Glu Glu Leu Lys
    1070            1075            1080

Arg Gln Ala Glu Leu Asp Gly Lys Ser Ala Lys Gln Asn Leu Asp
    1085            1090            1095

Lys Cys Tyr Gly Gln Ile Lys Glu Leu Asn Glu Lys Ile Thr Arg
```

-continued

```
            1100                1105                1110
Leu Thr Tyr Glu Ile Glu Asp Glu Lys Arg Arg Lys Ser Val
        1115                1120                1125
Glu Asp Arg Phe Asp Gln Gln Lys Asn Asp Tyr Asp Gln Leu Gln
        1130                1135                1140
Lys Ala Arg Gln Cys Glu Lys Glu Asn Leu Gly Trp Gln Lys Leu
        1145                1150                1155
Glu Ser Glu Lys Ala Ile Lys Glu Lys Glu Tyr Glu Ile Glu Arg
        1160                1165                1170
Leu Arg Val Leu Leu Gln Glu Glu Gly Thr Arg Lys Arg Glu Tyr
        1175                1180                1185
Glu Asn Glu Leu Ala Lys Val Arg Asn His Tyr Asn Glu Glu Met
        1190                1195                1200
Ser Asn Leu Arg Asn Lys Tyr Glu Thr Glu Ile Asn Ile Thr Lys
        1205                1210                1215
Thr Thr Ile Lys Glu Ile Ser Met Gln Lys Glu Asp Asp Ser Lys
        1220                1225                1230
Asn Leu Arg Asn Gln Leu Asp Arg Leu Ser Arg Glu Asn Arg Asp
        1235                1240                1245
Leu Lys Asp Glu Ile Val Arg Leu Asn Asp Ser Ile Leu Gln Ala
        1250                1255                1260
Thr Glu Gln Arg Arg Arg Ala Glu Glu Asn Ala Leu Gln Gln Lys
        1265                1270                1275
Ala Cys Gly Ser Glu Ile Met Gln Lys Lys Gln His Leu Glu Ile
        1280                1285                1290
Glu Leu Lys Gln Val Met Gln Gln Arg Ser Glu Asp Asn Ala Arg
        1295                1300                1305
His Lys Gln Ser Leu Glu Glu Ala Ala Lys Thr Ile Gln Asp Lys
        1310                1315                1320
Asn Lys Glu Ile Glu Arg Leu Lys Ala Glu Phe Gln Glu Glu Ala
        1325                1330                1335
Lys Arg Arg Trp Glu Tyr Glu Asn Glu Leu Ser Lys Val Arg Asn
        1340                1345                1350
Asn Tyr Asp Glu Glu Ile Ile Ser Leu Lys Asn Gln Phe Glu Thr
        1355                1360                1365
Glu Ile Asn Ile Thr Lys Thr Thr Ile His Gln Leu Thr Met Gln
        1370                1375                1380
Lys Glu Glu Asp Thr Ser Gly Tyr Arg Ala Gln Ile Asp Asn Leu
        1385                1390                1395
Thr Arg Glu Asn Arg Ser Leu Ser Glu Glu Ile Lys Arg Leu Lys
        1400                1405                1410
Asn Thr Leu Thr Gln Thr Thr Glu Asn Leu Arg Arg Val Glu Glu
        1415                1420                1425
Asp Ile Gln Gln Gln Lys Ala Thr Gly Ser Glu Val Ser Gln Arg
        1430                1435                1440
Lys Gln Gln Leu Glu Val Glu Leu Arg Gln Val Thr Gln Met Arg
        1445                1450                1455
Thr Glu Glu Ser Val Arg Tyr Lys Gln Ser Leu Asp Asp Ala Ala
        1460                1465                1470
Lys Thr Ile Gln Asp Lys Asn Lys Glu Ile Glu Arg Leu Lys Gln
        1475                1480                1485
Leu Ile Asp Lys Glu Thr Asn Asp Arg Lys Cys Leu Glu Asp Glu
        1490                1495                1500
```

```
Asn Ala Arg Leu Gln Arg Val Gln Tyr Asp Leu Gln Lys Ala Asn
    1505                1510                1515

Ser Ser Ala Thr Glu Thr Ile Asn Lys Leu Lys Val Gln Glu Gln
    1520                1525                1530

Glu Leu Thr Arg Leu Arg Ile Asp Tyr Glu Arg Val Ser Gln Glu
    1535                1540                1545

Arg Thr Val Lys Asp Gln Asp Ile Thr Arg Phe Gln Asn Ser Leu
    1550                1555                1560

Lys Glu Leu Gln Leu Gln Lys Gln Lys Val Glu Glu Glu Leu Asn
    1565                1570                1575

Arg Leu Lys Arg Thr Ala Ser Glu Asp Ser Cys Lys Arg Lys Lys
    1580                1585                1590

Leu Glu Glu Glu Leu Glu Gly Met Arg Arg Ser Leu Lys Glu Gln
    1595                1600                1605

Ala Ile Lys Ile Thr Asn Leu Thr Gln Gln Leu Glu Gln Ala Ser
    1610                1615                1620

Ile Val Lys Lys Arg Ser Glu Asp Asp Leu Arg Gln Gln Arg Asp
    1625                1630                1635

Val Leu Asp Gly His Leu Arg Glu Lys Gln Arg Thr Gln Glu Glu
    1640                1645                1650

Leu Arg Arg Leu Ser Ser Glu Val Glu Ala Leu Arg Arg Gln Leu
    1655                1660                1665

Leu Gln Glu Gln Glu Ser Val Lys Gln Ala His Leu Arg Asn Glu
    1670                1675                1680

His Phe Gln Lys Ala Ile Glu Asp Lys Ser Arg Ser Leu Asn Glu
    1685                1690                1695

Ser Lys Ile Glu Ile Glu Arg Leu Gln Ser Leu Thr Glu Asn Leu
    1700                1705                1710

Thr Lys Glu His Leu Met Leu Glu Glu Glu Leu Arg Asn Leu Arg
    1715                1720                1725

Leu Glu Tyr Asp Asp Leu Arg Arg Gly Arg Ser Glu Ala Asp Ser
    1730                1735                1740

Asp Lys Asn Ala Thr Ile Leu Glu Leu Arg Ser Gln Leu Gln Ile
    1745                1750                1755

Ser Asn Asn Arg Thr Leu Glu Leu Gln Gly Leu Ile Asn Asp Leu
    1760                1765                1770

Gln Arg Glu Arg Glu Asn Leu Arg Gln Glu Ile Glu Lys Phe Gln
    1775                1780                1785

Lys Gln Ala Leu Glu Ala Ser Asn Arg Ile Gln Glu Ser Lys Asn
    1790                1795                1800

Gln Cys Thr Gln Val Val Gln Glu Arg Glu Ser Leu Leu Val Lys
    1805                1810                1815

Ile Lys Val Leu Glu Gln Asp Lys Ala Arg Leu Gln Arg Leu Glu
    1820                1825                1830

Asp Glu Leu Asn Arg Ala Lys Ser Thr Leu Glu Ala Glu Thr Arg
    1835                1840                1845

Val Lys Gln Arg Leu Glu Cys Glu Lys Gln Gln Ile Gln Asn Asp
    1850                1855                1860

Leu Asn Gln Trp Lys Thr Gln Tyr Ser Arg Lys Glu Glu Ala Ile
    1865                1870                1875

Arg Lys Ile Glu Ser Glu Arg Glu Lys Ser Glu Arg Glu Lys Asn
    1880                1885                1890
```

-continued

```
Ser Leu Arg Ser Glu Ile Glu Arg Leu Gln Ala Glu Ile Lys Arg
    1895                1900                1905

Ile Glu Glu Arg Cys Arg Arg Lys Leu Glu Asp Ser Thr Arg Glu
    1910                1915                1920

Thr Gln Ser Gln Leu Glu Thr Glu Arg Ser Arg Tyr Gln Arg Glu
    1925                1930                1935

Ile Asp Lys Leu Arg Gln Arg Pro Tyr Gly Ser His Arg Glu Thr
    1940                1945                1950

Gln Thr Glu Cys Glu Trp Thr Val Asp Thr Ser Lys Leu Val Phe
    1955                1960                1965

Asp Gly Leu Arg Lys Lys Val Thr Ala Met Gln Leu Tyr Glu Cys
    1970                1975                1980

Gln Leu Ile Asp Lys Thr Thr Leu Asp Lys Leu Leu Lys Gly Lys
    1985                1990                1995

Lys Ser Val Glu Glu Val Ala Ser Glu Ile Gln Pro Phe Leu Arg
    2000                2005                2010

Gly Ala Gly Ser Ile Ala Gly Ala Ser Ala Ser Pro Lys Glu Lys
    2015                2020                2025

Tyr Ser Leu Val Glu Ala Lys Arg Lys Leu Ile Ser Pro Glu
    2030                2035                2040

Ser Thr Val Met Leu Leu Glu Ala Gln Ala Ala Thr Gly Gly Ile
    2045                2050                2055

Ile Asp Pro His Arg Asn Glu Lys Leu Thr Val Asp Ser Ala Ile
    2060                2065                2070

Ala Arg Asp Leu Ile Asp Phe Asp Asp Arg Gln Gln Ile Tyr Ala
    2075                2080                2085

Ala Glu Lys Ala Ile Thr Gly Phe Asp Asp Pro Phe Ser Gly Lys
    2090                2095                2100

Thr Val Ser Val Ser Glu Ala Ile Lys Lys Asn Leu Ile Asp Arg
    2105                2110                2115

Glu Thr Gly Met Arg Leu Leu Glu Ala Gln Ile Ala Ser Gly Gly
    2120                2125                2130

Val Val Asp Pro Val Asn Ser Val Phe Leu Pro Lys Asp Val Ala
    2135                2140                2145

Leu Ala Arg Gly Leu Ile Asp Arg Asp Leu Tyr Arg Ser Leu Asn
    2150                2155                2160

Asp Pro Arg Asp Ser Gln Lys Asn Phe Val Asp Pro Val Thr Lys
    2165                2170                2175

Lys Lys Val Ser Tyr Val Gln Leu Lys Glu Arg Cys Arg Ile Glu
    2180                2185                2190

Pro His Thr Gly Leu Leu Leu Leu Ser Val Gln Lys Arg Ser Met
    2195                2200                2205

Ser Phe Gln Gly Ile Arg Gln Pro Val Thr Val Thr Glu Leu Val
    2210                2215                2220

Asp Ser Gly Ile Leu Arg Pro Ser Thr Val Asn Glu Leu Glu Ser
    2225                2230                2235

Gly Gln Ile Ser Tyr Asp Glu Val Gly Glu Arg Ile Lys Asp Phe
    2240                2245                2250

Leu Gln Gly Ser Ser Cys Ile Ala Gly Ile Tyr Asn Glu Thr Thr
    2255                2260                2265

Lys Gln Lys Leu Gly Ile Tyr Glu Ala Met Lys Ile Gly Leu Val
    2270                2275                2280

Arg Pro Gly Thr Ala Leu Glu Leu Leu Glu Ala Gln Ala Ala Thr
```

```
                2285                2290                2295

Gly Phe Ile Val Asp Pro Val Ser Asn Leu Arg Leu Pro Val Glu
        2300                2305                2310

Glu Ala Tyr Lys Arg Gly Leu Val Gly Ile Glu Phe Lys Glu Lys
        2315                2320                2325

Leu Leu Ser Ala Glu Arg Ala Val Thr Gly Tyr Asn Asp Pro Glu
        2330                2335                2340

Thr Gly Asn Ile Ile Ser Leu Phe Gln Ala Met Asn Lys Glu Leu
        2345                2350                2355

Ile Glu Lys Gly His Gly Ile Arg Leu Leu Glu Ala Gln Ile Ala
        2360                2365                2370

Thr Gly Gly Ile Ile Asp Pro Lys Glu Ser His Arg Leu Pro Val
        2375                2380                2385

Asp Ile Ala Tyr Lys Arg Gly Tyr Phe Asn Glu Glu Leu Ser Glu
        2390                2395                2400

Ile Leu Ser Asp Pro Ser Asp Asp Thr Lys Gly Phe Phe Asp Pro
        2405                2410                2415

Asn Thr Glu Glu Asn Leu Thr Tyr Leu Gln Leu Lys Glu Arg Cys
        2420                2425                2430

Ile Lys Asp Glu Glu Thr Gly Leu Cys Leu Leu Pro Leu Lys Glu
        2435                2440                2445

Lys Lys Lys Gln Val Gln Thr Ser Gln Lys Asn Thr Leu Arg Lys
        2450                2455                2460

Arg Arg Val Val Ile Val Asp Pro Glu Thr Asn Lys Glu Met Ser
        2465                2470                2475

Val Gln Glu Ala Tyr Lys Lys Gly Leu Ile Asp Tyr Glu Thr Phe
        2480                2485                2490

Lys Glu Leu Cys Glu Gln Cys Glu Trp Glu Glu Ile Thr Ile
        2495                2500                2505

Thr Gly Ser Asp Gly Ser Thr Arg Val Val Leu Val Asp Arg Lys
        2510                2515                2520

Thr Gly Ser Gln Tyr Asp Ile Gln Asp Ala Ile Asp Lys Gly Leu
        2525                2530                2535

Val Asp Arg Lys Phe Phe Asp Gln Tyr Arg Ser Gly Ser Leu Ser
        2540                2545                2550

Leu Thr Gln Phe Ala Asp Met Ile Ser Leu Lys Asn Gly Val Gly
        2555                2560                2565

Thr Ser Ser Ser Met Gly Ser Gly Val Ser Asp Asp Val Phe Ser
        2570                2575                2580

Ser Ser Arg His Glu Ser Val Ser Lys Ile Ser Thr Ile Ser Ser
        2585                2590                2595

Val Arg Asn Leu Thr Ile Arg Ser Ser Ser Phe Ser Asp Thr Leu
        2600                2605                2610

Glu Glu Ser Ser Pro Ile Ala Ala Ile Phe Asp Thr Glu Asn Leu
        2615                2620                2625

Glu Lys Ile Ser Ile Thr Glu Gly Ile Glu Arg Gly Ile Val Asp
        2630                2635                2640

Ser Ile Thr Gly Gln Arg Leu Leu Glu Ala Gln Ala Cys Thr Gly
        2645                2650                2655

Gly Ile Ile His Pro Thr Thr Gly Gln Lys Leu Ser Leu Gln Asp
        2660                2665                2670

Ala Val Ser Gln Gly Val Ile Asp Gln Asp Met Ala Thr Ser Val
        2675                2680                2685
```

```
Lys Pro Ala Gln Lys Ala Phe Ile Gly Phe Glu Gly Val Lys Gly
    2690                2695                2700

Lys Lys Lys Met Ser Ala Ala Glu Ala Val Lys Glu Lys Trp Leu
    2705                2710                2715

Pro Tyr Glu Ala Gly Gln Arg Phe Leu Glu Phe Gln Tyr Leu Thr
    2720                2725                2730

Gly Gly Leu Val Asp Pro Glu Val His Gly Arg Ile Ser Thr Glu
    2735                2740                2745

Glu Ala Ile Arg Lys Gly Phe Ile Asp Gly Arg Ala Ala Gln Arg
    2750                2755                2760

Leu Gln Asp Thr Ser Ser Tyr Ala Lys Ile Leu Thr Cys Pro Lys
    2765                2770                2775

Thr Lys Leu Lys Ile Ser Tyr Lys Asp Ala Ile Asn Arg Ser Met
    2780                2785                2790

Val Glu Asp Ile Thr Gly Leu Arg Leu Leu Glu Ala Ala Ser Val
    2795                2800                2805

Ser Ser Lys Gly Leu Pro Ser Pro Tyr Asn Met Ser Ser Ala Pro
    2810                2815                2820

Gly Ser Arg Ser Gly Ser Arg Ser Gly Ser Arg Ser Gly Ser Arg
    2825                2830                2835

Ser Gly Ser Arg Ser Gly Ser Arg Arg Gly Ser Phe Asp Ala Thr
    2840                2845                2850

Gly Asn Ser Ser Tyr Ser Tyr Ser Tyr Ser Phe Ser Ser Ser Ser
    2855                2860                2865

Ile Gly His
    2870

<210> SEQ ID NO 27
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Modified with succinic anhydride and N-hydroxy
      ester
<220> FEATURE:
<221> NAME/KEY: MISC_FEATURE
<222> LOCATION: (3)..(3)
<223> OTHER INFORMATION: Branched moiety: Pro - Asp - succinic
      anhydride - N-hydroxy ester
<220> FEATURE:
<221> NAME/KEY: MISC_FEATURE
<222> LOCATION: (4)..(4)
<223> OTHER INFORMATION: Optionally modified with a capture moiety

<400> SEQUENCE: 27

Asp Pro Lys Lys Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Thr Lys Gln Thr Ala Arg
1               5
```

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Lys Gln Leu Ala Thr Lys Ala Ala Arg
1               5

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Lys Ser Ala Pro Ala Thr Gly Gly Val Lys Lys Pro His Arg
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Tyr Gln Lys Ser Thr Glu Leu Leu Ile Arg
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic

<400> SEQUENCE: 32

Lys Ser Ala Pro Ser Thr Gly Gly Val Lys Lys Pro His Arg
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Synthetic

<400> SEQUENCE: 33

Thr Lys Gln Thr Ala Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Arg Gly Gly Val Lys Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Lys Thr Glu Ser His His Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Leu Ala His Tyr Asn Lys Arg
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic

<400> SEQUENCE: 37

Lys Ser Thr Gly Gly Lys
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Gly Leu Gly Lys Gly Gly Ala Lys Arg
1               5

<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

Leu Leu Leu Pro Gly Glu Leu Ala Lys His Ala Val Ser Glu Gly Thr
1               5                   10                  15

Lys

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Lys Thr Glu Ser His His Lys
1               5

```
<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Gly Gly Lys Gly Leu Gly Lys
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Lys Thr Glu Ser His His Lys Ala Lys
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic

<400> SEQUENCE: 43

Gly Lys Gly Gly Lys
1               5

<210> SEQ ID NO 44
<211> LENGTH: 19
<212> TYPE: PRT
<213> ORGANISM: Artificial Sequence
<220> FEATURE:
<223> OTHER INFORMATION: Synthetic

<400> SEQUENCE: 44

Phe Gly Lys His Gly Gly Thr Ile Pro Ile Val Pro Thr Ala Glu Phe
1               5                   10                  15

Gln Asp Arg
```